(12) United States Patent
Isalan et al.

(10) Patent No.: US 9,732,129 B2
(45) Date of Patent: Aug. 15, 2017

(54) PEPTIDES AND USES THEREOF

(71) Applicant: FUNDACIO CENTRE DE REGULACIO GENOMICA, Barcelona (ES)

(72) Inventors: Mark Isalan, Barcelona (ES); Mireia Garriga-Canut, Barcelona (ES)

(73) Assignee: Fundacio Centre de Regulacio Genomica, Barcelona (ES)

( * ) Notice: Subject to any disclaimer, the term of this patent is extended or adjusted under 35 U.S.C. 154(b) by 0 days.

(21) Appl. No.: 14/714,948

(22) Filed: May 18, 2015

(65) Prior Publication Data

US 2016/0200781 A1    Jul. 14, 2016

Related U.S. Application Data

(63) Continuation of application No. 13/879,422, filed as application No. PCT/EP2011/068139 on Oct. 17, 2011, now Pat. No. 9,096,682.

(30) Foreign Application Priority Data

Oct. 15, 2010   (EP) .................................... 10187818

(51) Int. Cl.
    C07K 14/47     (2006.01)
    A61K 38/17     (2006.01)
    A61K 48/00     (2006.01)
    A61K 38/00     (2006.01)

(52) U.S. Cl.
    CPC ...... *C07K 14/4703* (2013.01); *A61K 38/1709* (2013.01); *A61K 38/00* (2013.01); *A61K 48/00* (2013.01)

(58) Field of Classification Search
    None
    See application file for complete search history.

(56) References Cited

U.S. PATENT DOCUMENTS

| 2003/0068675 A1 | 4/2003 | Liu |
| 2003/0466141 | 9/2003 | Case et al. |

FOREIGN PATENT DOCUMENTS

| WO | 01/30843 | 5/2001 |
| WO | 03/104414 A2 | 12/2003 |
| WO | 2007/081647 | 7/2007 |
| WO | 2011/016840 | 2/2011 |

OTHER PUBLICATIONS

Garriga-Canuta, et al., "Synthetic zinc finger repressors reduce mutant huntingtin expression in the brain of R6/2 mice.", PNAS, E3136-E3145 (2012).
Isalan et al., "A rapid, generally applicable method to engineer zinc fingers illustrated by targeting the HIV-1 promoter", Nature Biotechnology, 19(7):656-660 (2001).
Liu et al., "Replication-dependent instability at (CTG)center dot(CAG) repeat hairpins in human cells." Nature Chemical Biology, 6(9):652-659 (2010).
Lund, C.V. et al., "Zinc Finger Transcription Factors Designed for Bispecific Coregulation of ErbB2 and ErbB3 Receptors: Insights into ErbB Receptor Biology", Molecular and Cellular Biology 25(20):9082-9091 (2005).
Mittelman et al., "Zinc-finger directed double-strand breaks within CAG repeat tracts promote repeat instability in human cells", Proceeds of the National Academy of Sciences of the United States of America, 106(24):9607-9612 (2009).
Morisaki, T. et al., "Rapid Transcriptional Activity in Vivo and Slow DNA Binding in Vitro by an Artificial Multi-Zinc Finger Protein1", Biochesmtry 47:10171-10177 (2008).
Spragga et al., "Spectroscopic studies of wild-type and mutant "zinc finger" peptides: Determination of domain folding and structure", Proc. Natl. Acad. Sci USA, 87:137-141 (1990).
Tan et al.,"Zinc-finger protein-targeted gene regulation: genomewide single-gene specificity", Proc Natl Acid Sci, 100 (21):11997-12002 (2003).

*Primary Examiner* — Addison D Ault
(74) *Attorney, Agent, or Firm* — Nixon Peabody LLP; David S. Resnick; Tari W. Mills

(57) ABSTRACT

Disclosed herein are zinc finger peptides having at least 4 zinc finger domains, such as 6, 11, 12 or 18 zinc finger domains. The zinc finger peptides may be fused to effector domains for modulating gene expression. Zinc finger peptides of the invention are useful for targeting trinucleotide-repeat sequences in mutant genes and may have applications in gene therapy. The zinc finger peptides may have nucleic acid recognition sequences according to SEQ ID NO: 101. Also disclosed are methods for constructing poly-zinc finger peptides having arrays of at least 8 zinc finger domains, along with zinc finger frameworks that may be useful for selecting zinc finger peptides from libraries.

18 Claims, 13 Drawing Sheets

PEPTIDES AND USES THEREOF

CROSS REFERENCE TO RELATED APPLICATIONS

This application is a continuation application of co-pending U.S. application Ser. No. 13/879,422 filed on Apr. 15, 2013, which is a 35 U.S.C. §371 National Phase Entry Application of International Application No. PCT/EP2011/068139 filed on Oct. 17, 2011, which designates the U.S., and which claims benefit of European Application No. 10187818.9 filed on Oct. 15, 2010, the contents of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Jul. 24, 2013, is named 051039-077700_SL.txt and is 54,676 bytes in size.

FIELD OF THE INVENTION

This invention relates to novel zinc finger peptides having desirable properties, including binding specificity and affinity for selected nucleic acid sequences and repression of target gene expression. In particular, the invention relates to zinc finger transcriptional repressor proteins and to the repression of genes involved in neurological disorders, and to methods and therapeutic uses involving such proteins.

BACKGROUND OF THE INVENTION

Neurological disorders are diseases that affect the central nervous system (brain and spinal cord), the peripheral nervous system (peripheral nerves and cranial nerves), and the autonomic nervous system (parts of which are located in both central and peripheral nervous systems). More than 600 neurological diseases have been identified in humans, which together affect all functions of the body, including coordination, communication, memory, learning, eating, and in some cases mortality.

Although many tissues and organs in animals are capable of self-repair, generally the neurological system is not. Therefore, neurological disorders are often characterised by a progressive worsening of symptoms, beginning with minor problems that allow detection and diagnosis, but becoming steadily more severe—sometimes resulting in the death of the affected individual. While the exact causes or triggers of many neurological disorders are still unknown, for others the causes are well documented and researched. For some of these diseases there are "effective" treatments, which alleviate symptoms and/or prolong survival. However, despite intense research efforts, for most neurological disorders, and particularly for the most serious diseases, there are still no cures. Hence, there is a clear need for new therapeutics and treatments for neurological disorders.

Current knowledge of neurological disorders shows that they can be caused by many different factors, including (but not limited to): inherited genetic abnormalities, problems in the immune system, injury to the brain or nervous system, or diabetes. One known cause of neurological disorder is a genetic abnormality leading to the pathological expansion of CAG repeats on certain genes, which results in extended polyglutamine (polyQ) tracts in the expressed mutated gene products (Walker (2007) *Lancet* 369(9557): 218-228). The resulting proteins are thought to aggregate and cause toxic gain-of-function diseases, including spinocerebellar ataxias, spinobulbar muscular atrophy and Huntington's disease (HD; Orr & Zoghbi (2007) *Annu. Rev. Neurosci.* 30: 575-621; Cha (2007) *Prog. Neurobiol.* 83(4): 228-248). HD neuropathology is associated with selective neuronal cell death, primarily of medium spiny neurons of the caudate and putamen, and to a lesser extent cortical neurons, leading to cognitive dysfunction and chorea (Walker (2007) *Lancet* 369(9557): 218-228; and Kumar et al. *Pharmacol. Rep.* 62(1): 1-14). Since the discovery, in 1993, that the htt gene caused HD (The-Huntington's-Disease-Collaborative-Research-Group (1993) *Cell* 72(6): 971-983), much attention has focused on how the CAG-repeat number affects the pathology and progression of this disease. Normally, the number of CAG repeats in the wild-type htt gene ranges from 10 to 29 (with a median of 18), whereas in HD patients it is typically in the range of 36 to 121 (with a median of 44). Furthermore, it has been shown that the age of onset of HD disease is correlated to CAG repeat number (Walker (2007) *Lancet* 369(9557): 218-228; and Kumar et al. *Pharmacol. Rep.* 62(1): 1-14).

Although there has been a great deal of research into cures for HD disease, currently available therapeutics treat only the symptoms of the disease, and so there is still no way of stopping or delaying the onset or progression of HD (Walker (2007) *Lancet* 369(9557): 218-228; and Kumar et al. *Pharmacol. Rep.* 62(1): 1-14). For this reason it would be extremely desirable to have a treatment for HD disease that addresses the cause rather than the symptoms of the disease.

Recently, RNA interference (RNAi) was shown to reduce expression of mutant htt (van Bilsen et al. (2008) *Hum. Gene Ther.* 19(7): 710-719; Zhang et al. (2009) *J. Neurochem.* 108(1): 82-90; Pfister et al. (2009) *Curr. Biol.* 19(9): 774-778). Although RNAi has been shown to be a very powerful tool, the success of this technique depends on targeting single nucleotide or deletion polymorphisms that differentiate between mutant and wt alleles, and these often differ from patient to patient. The apparent requirement for per-sonalised siRNA designs currently raises challenges for clinical trials and approved use in humans.

In a more general approach, Hu et al. used peptide nucleic acid (PNA) and locked nucleic acid (LNA) antisense oligomers, to target expanded CAG repeats of the ataxin-3 and htt genes (Hu et al. (2009) *Nat. Biotechnol.* 27(5): 478-484; Hu et al. (2009) *Ann. NY Acad. Sci.* 1175: 24-31). They reported selective inhibition of the mutant allele with peptide nucleic acids (PNAs) for up to 22 days. Although these results were promising, PNAs cannot be delivered to the central nervous system. Therefore, the authors also tried locked nucleic acids (LNAs), which are perhaps more suitable for use in vivo. Although selective inhibition of the mutant allele was observed, only up to 30% inhibition of wt htt was seen at the highest and most effective concentration of LNA used.

Therefore, it would be highly desirable to have alternative and/or more effective therapeutic molecules and treatments for HD and related disorders caused by expanded CAG repeats.

Accordingly, the present invention seeks to overcome or at least alleviate one or more of the problems in the prior art.

SUMMARY OF THE INVENTION

In general terms, the present invention provides new zinc finger peptide frameworks (and encoding nucleic acid molecules) that can be used for the modulation of gene expression in vitro and/or in vivo. The new zinc finger peptides of the invention may be particularly useful in the modulation of target genes associated with expanded nucleotide repeats, such as CAG repeats, and more specifically the repression of such genes. In some embodiments, the new zinc finger peptides of the invention contain a larger number of individual zinc finger domains than any known artificial zinc finger peptide shown to possess transcriptional modulation activity either in vitro or in vivo and, hence, the invention opens up the possibility of targeting longer nucleic acid sequences than previously thought possible. As a consequence, the possibility of more specific gene targeting is envisaged, which may be particularly useful for the modulation of gene expression within the genome and/or for distinguishing between similar nucleic acid sequences of differing lengths. Furthermore, the invention relates to therapeutic molecules and compositions for use in treating diseases associated with expanded CAG repeat sequences, such as neurological diseases, and particularly Huntington's disease (HD). In some aspects and embodiments, the invention is directed to methods and therapeutic treatment regimes for treating patients affected by or diagnosed with HD. For example, the therapeutic molecules of the invention may be used for delaying the onset of symptoms, and/or for treating or alleviating the symptoms of the disease, and/or for reducing the severity or preventing the progression of the disease.

Hence, in one aspect of this invention, the Applicant has created novel zinc finger peptides (ZFP) that may be used to reduce the expression of mutant htt genes. Furthermore, since zinc fingers can be readily re-engineered to bind different DNA sequences (*Annu. Rev. Biochem.* 70: 313-340 (2001); *Chem. Rev.* 104(2): 789-799; *Biochemistry* 41(22): 7074-7081 (2002); *Nucleic Acids Res.* 34(Web Server issue): W516-523 92006); *Nat. Methods* 7(2): 91-9, (2009); *Genome Res.* 19(7): 1279-1288 (2009); *Proc. Natl. Acad. Sci. USA* 100(21): 12271-12276 (2003); *Nat. Protoc.* 1(3): 1637-1652 (2006); *Mol. Cell* 31(2): 294-301(2008)., including CAG-repeats (*Proc. Natl. Acad. Sci. USA* 106(24): 9607-9612, (2009)), they may be useful for targeting genes such as htt at a transcriptional level. In particular, the modular nature of the zinc finger peptides of the invention makes them particularly suitable for targeting expanded repeat sequences that may be found in genomes, and especially triplet-repeat sequences for which there is a convenient correspondence in register between the targeted triplet nucleic acid stretch and its respective bound zinc finger peptide.

Rational design was used to create ZFPs able to recognise and bind poly-5'-GC (A/T)-3', such that it would recognise both poly-CAG sequences and its complementary DNA strand. Stable expression of the ZFPs was shown to reduce expression of chromosomal mutant htt gene in a model cell line, at both the protein and the RNA level. Furthermore, repression of the mutant gene was shown to persist for extended periods of at least 20 days. In vivo tests further demonstrated the ability of these zinc finger peptides to delay the onset of HD symptoms.

ZFP ranging from 4 to 18-fingers were synthesised and shown to repress a target gene with 35 or more CAG repeats preferentially, when compared to shorter repeats, thus demonstrating the utility of these molecules in preferentially targeting expanded CAG repeats. Accordingly, mutant htt gene expression can be repressed while leaving the wild-type allele relatively unaffected.

By concatenating individual zinc finger domains into long chains using selected linker sequences, zinc finger peptides of the invention have been designed and synthesised with a greater number of zinc finger domains than previously known; and these extended ZFPs have been demonstrated to selectively target nucleic acid sequences with high affinity and specificity. The zinc fingers and methods of the invention are particularly beneficial for targeting repeat nucleic acid sequences by concatenating essentially identical zinc finger-nucleic acid-binding domains.

Accordingly, in a first aspect of the invention there is provided a zinc finger peptide having from 8 to 32 zinc finger domains, and wherein at least one zinc finger domain comprises a nucleic acid recognition sequence according to SEQ ID NO: 101.

In another aspect, there is provided a zinc finger peptide comprising the sequence: N'-[(Formula 2)-$X_6]_{n0}$-{[(Formula 2)-$X_5$-(Formula 2)-$X_6]_{n1}$-[(Formula 2)-$X_5$-(Formula 2)-$X_L$]}$_{n2}$-[(Formula 2)-$X_5$-(Formula 2)-$X_6]_{n3}$-[(Formula 2)-$X_5$-(Formula 2)]-[$X_6$-(Formula 2)]$_{n4}$-C', wherein n0 is 0 or 1, n1 is from 1 to 4, n2 is 1 or 2, n3 is from 1 to 4, n4 is 0 or 1, $X_5$ is a linker sequence of 5 amino acids, $X_6$ is a linker sequence of 6 or 7 amino acids, and $X_L$ is a linker sequence of at least 8 amino acids; and Formula 2 is a zinc finger domain of the sequence—$X_{0-2}$ C $X_{1-5}$ C $X_{2-7}$ $X^{-1}$ $X^{+1}$ $X^{+2}$ $X^{+3}$ $X^{+4}$ $X^{+5}$ $X^{+6}$ H $X_{3-6}$ $H/_C$—, wherein X is any amino acid, the numbers in subscript indicate the possible numbers of residues represented by X at that position, and the number in superscript indicates the position of the amino acid in the recognition sequence of the zinc finger domain. Advantageously, n0 and/or n4=0. Suitably, in this and any other aspects and embodiments, $X_6$ is a linker of 6 amino acids. Thus, in a preferred embodiment, the zinc finger peptide of the invention has the formula N'-{[(Formula 2)-$X_5$-(Formula 2)-$X_6]_{n1}$-[(Formula 2)-$X_5$-(Formula 2)-$X_L$]}$_{n2}$-[(Formula 2)-$X_5$-(Formula 2)-$X_6]_{n3}$-[(Formula 2)-$X_5$-(Formula 2)]-C', wherein $X_6$ is a linker sequence of 6 amino acids, and n1, n2, n3, n4, $X_5$ and $X_L$ are as previously described. In some beneficial embodiments, the extended linker sequence $X_L$ is from 8 to 50 amino acids, or 11 to 40 amino acids; n1 is preferably 2, and n3 is preferably 2. In a preferred embodiment at least one zinc finger domain has a $X^{-1}$ $X^{+1}$ $X^{+2}$ $X^{+3}$ $X^{+4}$ $X^{+5}$ $X^{+6}$ recognition sequence according to SEQ ID NO: 101

By setting the sequence $X^{-1}$ $X^{+1}$ $X^{+2}$ $X^{+3}$ $X^{+4}$ $X^{+5}$ $X^{+6}$ to be the same or similar amino acid sequence in a plurality of adjacent zinc finger domains (so that each of the plurality of fingers binds preferentially to the same trinucleotide sequence), the peptides of the invention are advantageously capably of targeting (or binding) to trinucleotide repeat sequences in DNA, which may be associated with genetic abnormalities. In one embodiment of this and other aspects of the invention, therefore, at least one $X^{-1}$ $X^{+1}$ $X^{+2}$ $X^{+3}$ $X^{+4}$ $X^{+5}$ $X^{+6}$ sequence is the amino acid sequence QRATLQR (SEQ ID NO: 1), which enables the targeting of CAG-repeat and/or CTG-repeat sequences. It may be possible to make conservative mutations to the recognition sequence while still enabling zinc finger recognition of the same triplet nucleotide sequences. Therefore, each $X^{-1}$ $X^{+1}$ $X^{+2}$ $X^{+3}$ $X^{+4}$ $X^{+5}$ $X^{+6}$ sequence may be mutated (conservatively—so that it still binds CAG or CTG triplets), such that it is identical to QRATLQR (SEQ ID NO: 1) at 4, 5, 6 or 7 positions. Accordingly, in some embodiments the recognition sequences are selected from the group consisting of: SEQ ID NO: 1, SEQ ID NO: 101, SEQ ID NO: 102, SEQ ID NO: 103, SEQ ID NO: 104, SEQ ID NO: 105, SEQ ID NO: 106, and SEQ ID NO: 107 or combinations thereof.

Accordingly, the invention further provides a zinc finger peptide comprising at least 4 zinc finger domains of Formula 2: $X_{0-2}$ C $X_{1-5}$ C $X_{2-7}$ $X^{-1}$ $X^{+1}$ $X^{+2}$ $X^{+3}$ $X^{+4}$ $X^{+5}$ $X^{+6}$ H $X_{3-6}$ $^H/_C$, wherein X is any amino acid, the numbers in subscript indicate the possible numbers of residues represented by X at that position, and the number in superscript indicates the position of the amino acid in the recognition sequence of the zinc finger domain; and at least one $X^{-1}$ $X^{+1}$ $X^{+2}$ $X^{+3}$ $X^{+4}$ $X^{+5}$ $X^{+6}$ sequence is selected from the group consisting of: SEQ ID NO: 1, SEQ ID NO: 101, SEQ ID NO: 102, SEQ ID NO: 103, SEQ ID NO: 104, SEQ ID NO: 105, SEQ ID NO: 106, and SEQ ID NO: 107. Thus, in some embodiments, at least 4 (e.g. 4, 6, 11, 12, 18 or all of the) adjacent zinc finger domains of the peptide may have a sequence selected from the group consisting of: SEQ ID NO: 1, SEQ ID NO: 101, SEQ ID NO: 102, SEQ ID NO: 103, SEQ ID NO: 104, SEQ ID NO: 105, SEQ ID NO: 106, and SEQ ID NO: 107. A preferred recognition sequence is QRATLQR (SEQ ID NO: 1); and suitably all of the zinc finger domains of the peptide have this sequence.

Particularly useful peptides of the invention comprise the sequence of SEQ ID NO: 6, SEQ ID NO: 8, SEQ ID NO: 10, SEQ ID NO: 12, SEQ ID NO: 14 or SEQ ID NO: 108; or sequences having at least 70%, at least 80%, at least 90%, at least 95%, at least 98% or at least 99% sequence identity thereto.

Suitably, the peptide of the invention bind double-stranded trinucleotide repeat nucleic acid sequences comprising CAG-repeat, CTG-repeat, and/or CAGCTG-repeat sequences containing at least 10, at least 22 triplet repeats, at least 35 repeats, or at least 63 triplet repeats. Desirably, the peptides of the invention have binding affinity (dissociation constant) for its respective target sequence of at least 1 nM; at least 100 pM or at least 10 pM. Binding affinity may be determined in any suitable manner known to the person of skill in the art, such as by Biacore.

In another aspect, the invention relates to chimeric or fusion proteins comprising the zinc finger peptides of the invention conjugated to a non-zinc finger domain.

In another aspect, the invention relates to a naïve zinc finger peptide library. According to one embodiment, the naïve peptide library comprises a plurality of zinc finger peptides according to the invention, wherein at least one zinc finger domain is diversified at one or more of positions $X^{-1}$ $X^{+1}$ $X^{+2}$ $X^{+3}$ $X^{+4}$ $X^{+5}$ and $X^{+6}$. Another aspect relates to the use of a naïve zinc finger peptide library in the selection of a zinc finger peptide able to bind to a desired target nucleic acid sequence. Thus, another aspect of the invention relates to zinc finger peptides identified from the libraries of the invention.

In another aspect, the invention provides for therapeutic and non-therapeutic (e.g. diagnostic) uses for the zinc finger peptides and fusion proteins of the invention. Aspects and embodiments of the invention therefore include formulations, medicaments and pharmaceutical compositions comprising the zinc finger peptides. In one embodiment, the invention relates to a zinc finger peptide for use in medicine. More specifically, the zinc finger peptides and therapeutics of the invention may be used for modulating the expression of a target gene in a cell. The zinc finger peptides of the invention may be used in the treatment of various diseases and conditions of the human or animal body, such as neurological diseases, for example, Huntington's disease; and other diseases caused by or diagnosed by gene expansion of repeat nucleotide sequences—particularly trinucleotide-repeat sequences. In one embodiment, the invention relates to the treatment of diseases or conditions associated with the mutated CAG-repeat gene and/or expression of gene products containing extended polyglutamine (polyQ) tracts. Treatment may also include preventative as well as therapeutic treatments and alleviation of a disease or condition.

The invention further encompasses nucleic acids that encode the zinc finger peptides, peptide libraries and fusion proteins of the invention, for example: expression vectors, and viral vectors, such as AAV (e.g. for use in gene therapy). Also encompassed is a cell comprising the nucleic acids and/or polypeptides of the invention.

In yet another aspect, the invention provides a method of making a nucleic acid sequence encoding a poly-zinc finger peptide comprising at least 8 zinc finger domains of Formula 1: $X_{0-2}$ C $X_{1-5}$ C $X_{9-14}$ H $X_{3-6}$ $^H/_C$, wherein X is any amino acid and the numbers in subscript indicate the possible number of residues represented by X at that position. In one embodiment, the method comprises: (a) providing nucleic acid molecules that encode a pair of zinc finger domains of Formula 1, wherein the adjacent zinc finger domains of each pair are separated by a linker sequence of 5 amino acids; (b) joining together nucleic acid molecules from step (a) to create nucleic acid molecules that encode an array of 4 or 6 zinc finger domains, wherein the adjacent pairs of zinc finger domains from step (a) are separated by a linker sequence of 6 or 7 amino acids; and (c) joining together nucleic acid molecules from step (b) to create a nucleic acid sequence encoding a poly-zinc finger peptide, wherein the adjacent arrays of zinc finger domains from step (b) are separated by a linker sequence of at least 8 amino acids. Optionally, the method may further comprise adding a single zinc finger domain to create a poly-zinc finger peptide having an odd number of zinc finger domains. For example: the method may further comprise step (d) attaching to the N- or C-terminus of the poly-zinc finger peptide of step (c), a single zinc finger domain linked to the N- or C-terminus by a linker sequence of 5 to 7 amino acids to create a poly-zinc finger peptide having an odd number of zinc finger domains. The method steps of the invention may be performed in any appropriate order. It will be appreciated that there are many different methods by which a nucleic acid sequence encoding such a poly-zinc finger peptide can be obtained. Therefore, the invention is also directed to nucleic acids that encode such poly-zinc finger peptides however they are obtained, and to poly-zinc finger peptides that are obtainable by expressing the above nucleic acid sequences.

Accordingly, in another aspect there is provided a method of making a poly-zinc finger peptide comprising at least 8 zinc finger domains of Formula 1: $X_{0-2}$ C $X_{1-5}$ C $X_{9-14}$ H $X_{3-6}$ $^H/_C$, wherein X is any amino acid and the numbers in subscript indicate the possible number of residues represented by X at that position, the method comprising expressing a nucleic acid sequence obtainable by the above method.

In still yet another aspect of the invention, there is provided a method of making a poly-zinc finger peptide comprising at least 8 zinc finger domains of Formula 1: $X_{0-2}$ C $X_{1-5}$ C $X_{9-14}$ H $X_{3-6}$ $^H/_C$, wherein X is any amino acid and the numbers in subscript indicate the possible number of residues represented by X at that position, the method comprising: (a) creating at least 4 pairs of zinc finger domains of Formula 1, the adjacent zinc finger domains of each pair being separated by a linker sequence of 5 amino acids; (b) creating at least 2 arrays of 4 or 6 zinc finger domains each by joining together 2 or 3 pairs of zinc fingers from step (a) using a linker sequence of 6 or 7 amino acids; and (c) joining together the at least 2 arrays of zinc finger domains from step (b) using a linker sequence of at least 8 amino acids. Suitably, the method is for making a poly-zinc finger peptide according to the invention.

In the methods of the invention each zinc finger domain may comprise a recognition sequence $X^{-1} X^{+1} X^{+2} X^{+3} X^{+4} X^{+5} X^{+6}$, which is identical to QRATLQR (SEQ ID NO: 1) at 4, 5, 6 or 7 positions.

It will be appreciated that zinc finger peptides of the invention may be further derivatised or conjugated to additional molecules, and that such derivatives and conjugates fall within the scope of the invention.

It should also be appreciated that, unless otherwise stated, optional features of one of more aspects of the invention may be incorporated into any other aspect of the invention.

All references cited herein are incorporated by reference in their entirety. Unless otherwise defined, all technical and scientific terms used herein have the same meaning as commonly understood by one of ordinary skill in the art to which this invention belongs.

BRIEF DESCRIPTION OF THE DRAWINGS

The invention is further illustrated by the accompanying drawings in which:

FIG. 1 (A) discloses SEQ ID NO: 114. (B) Gel shift assays show 4-, 6- or 12-finger arrays binding poly-CAG dsDNA and forming distinct complexes; negative control, transcription-translation mix (TNT). FIG. 1 (B) discloses SEQ ID NOS 115, 100 and 116, respectively, in order of appearance. (C) Left hand column—a schematic illustration of a hybrid zinc finger design according to one embodiment of the invention, which recognises the nucleic acid sequence 5'-GC(A/T)-3', which allows binding to either the $(GCA)_n$ or the $(GCT)_n$ complementary strands of the CAG-repeat dsDNA sequence. Right hand column—a gel shift assay demonstrating that the hybrid zinc finger binds equally to GCA or GCT triplets in mixed sequences. FIG. 1 (C) discloses SEQ ID NOS 1, 98 and 117, respectively, in order of appearance. (D) Specificity gel shift assay illustrating that a zinc finger peptide according to one embodiment of the invention (ZF6× Hunt), binds preferentially to CAG-repeats when compared to mutant sequences (D=A,G,T; S=C,G; H=A,C,T) FIG. 1 (D) discloses SEQ ID NOS 100 and 118-120, respectively, in order of appearance.

DETAILED DESCRIPTION OF THE INVENTION

Figure 1:
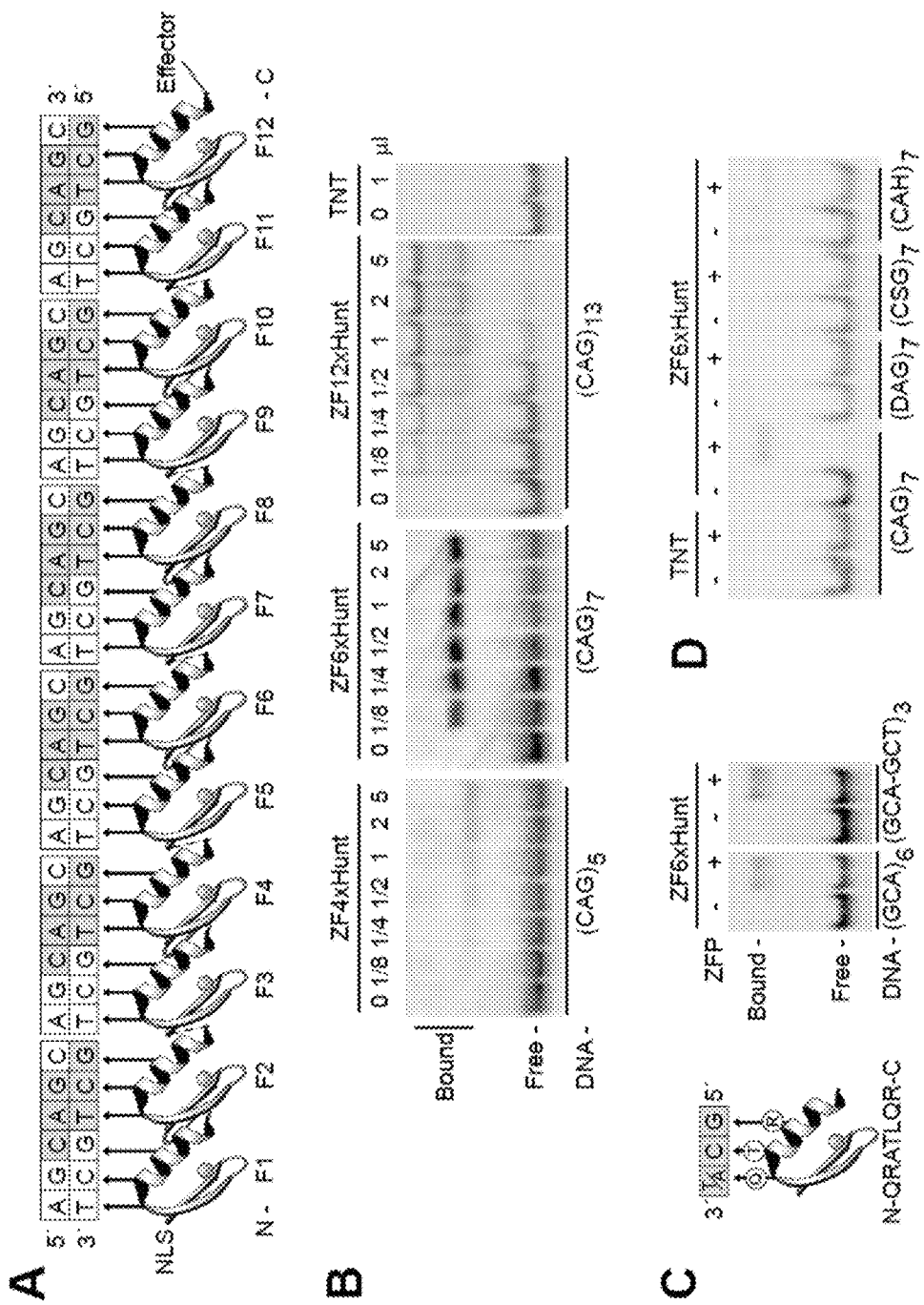
FIG. 1 Zinc finger arrays according to the invention bind to CAG-repeats. (A) A schematic illustration of a 12-finger array, showing recognition helices contacting 5'-GCT-3' bases on the lower DNA strand. Similar arrays of 4, 6, 12 or 18 zinc fingers were built (ZF4× Hunt, ZF6× Hunt, ZF12× Hunt and ZF18× Hunt). Nuclear localisation signals (NLS) and effectors (e.g. Kox-1 transcription repression domain) were added to N- and C-termini, respectively.

Unless defined otherwise, all technical and scientific terms used herein have the same meaning as commonly understood by one of ordinary skill in the art (e.g. in cell culture, molecular genetics, nucleic acid chemistry and biochemistry).

Unless otherwise indicated, the practice of the present invention employs conventional techniques of chemistry, molecular biology, microbiology, recombinant DNA technology, chemical methods, pharmaceutical formulations and delivery and treatment of patients, which are within the capabilities of a person of ordinary skill in the art. Such techniques are also explained in the literature, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N. Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridisation: Principles and Practice, Oxford University Press; M. J. Gait (Editor), 1984, Oligonucleotide Synthesis: A Practical Approach, IRL Press; and D. M. J. Lilley and J. E. Dahlberg, 1992, Methods of Enzymology: DNA Structure Part A: Synthesis and Physical Analysis of DNA Methods in Enzymology, Academic Press. Each of these general texts is herein incorporated by reference.

In order to assist with the understanding of the invention several terms are defined herein.

The term "amino acid" in the context of the present invention is used in its broadest sense and is meant to include naturally occurring L α-amino acids or residues. The commonly used one and three letter abbreviations for naturally occurring amino acids are used herein: A=Ala; C=Cys; D=Asp; E=Glu; F=Phe; G=Gly; H=His; I=Ile; K=Lys; L=Leu; M=Met; N=Asn; P=Pro; Q=Gln; R=Arg; S=Ser; T=Thr; V=Val; W=Trp; and Y=Tyr (Lehninger, A. L., (1975) *Biochemistry*, 2d ed., pp. 71-92, Worth Publishers, New York). The general term "amino acid" further includes D-amino acids, retro-inverso amino acids as well as chemically modified amino acids such as amino acid analogues, naturally occurring amino acids that are not usually incorporated into proteins such as norleucine, and chemically synthesised compounds having properties known in the art to be characteristic of an amino acid, such as β-amino acids. For example, analogues or mimetics of phenylalanine or proline, which allow the same conformational restriction of the peptide compounds as do natural Phe or Pro, are included within the definition of amino acid. Such analogues and mimetics are referred to herein as "functional equivalents" of the respective amino acid. Other examples of amino acids are listed by Roberts and Vellaccio, *The Peptides: Analysis, Synthesis, Biology*, Gross and Meiehofer, eds., Vol. 5 p. 341, Academic Press, Inc., N.Y. 1983, which is incorporated herein by reference.

The term "peptide" as used herein (e.g. in the context of a zinc finger peptide (ZFP) or framework) refers to a plurality of amino acids joined together in a linear or circular chain. The term oligopeptide is typically used to describe peptides having between 2 and about 50 or more amino acids. Peptides larger than about 50 amino acids are often referred to as polypeptides or proteins. For purposes of the present invention, however, the term "peptide" is not limited to any particular number of amino acids, and is used interchangeably with the terms "polypeptide" and "protein".

As used herein, the term "zinc finger domain" refers to an individual "finger", which comprises a ββα-fold stabilised by a zinc ion (as described elsewhere herein). Each zinc finger domain typically includes approximately 30 amino acids. The term "domain" (or "module"), according to its ordinary usage in the art, refers to a discrete continuous part of the amino acid sequence of a polypeptide that can be equated with a particular function. Zinc finger domains are largely structurally independent and may retain their structure and function in different environments. Typically, a zinc finger domain binds a triplet or (overlapping) quadruplet nucleotide sequence. Adjacent zinc finger domains arranged in tandem are joined together by linker sequences. A zinc finger peptide of the invention is composed of a plurality of "zinc finger domains", which in combination do not exist in nature. Therefore, they may be considered to be artificial or synthetic zinc finger peptides.

The terms "nucleic acid", "polynucleotide", and "oligonucleotide" are used interchangeably and refer to a deoxyribonucleotide (DNA) or ribonucleotide (RNA) polymer, in linear or circular conformation, and in either single- or double-stranded form. For the purposes of the present invention such DNA or RNA polymers may include natural nucleotides, non-natural or synthetic nucleotides, and mixtures thereof. Non-natural nucleotides may include analogues of natural nucleotides, as well as nucleotides that are modified in the base, sugar and/or phosphate moieties (e.g. phosphorothioate backbones). Examples of modified nucleic acids are PNAs and morpholino nucleic acids. Generally an analogue of a particular nucleotide has the same base-pairing specificity, i.e. an analogue of G will base-pair with C. For the purposes of the invention, these terms are not to be considered limiting with respect to the length of a polymer.

A "gene", as used herein, is the segment of nucleic acid (typically DNA) that is involved in producing a polypeptide or ribonucleic acid gene product. It includes regions preceding and following the coding region (leader and trailer) as well as intervening sequences (introns) between individual coding segments (exons). Conveniently, this term also includes the necessary control sequences for gene expression (e.g. enhancers, silencers, promoters, terminators etc.), which may be adjacent to or distant from the relevant coding sequence, as well as the coding and/or transcribed regions encoding the gene product.

As used herein the term "modulation", in relation to the expression of a gene refers to a change in the gene's activity. Modulation includes both activation (i.e. increase in activity or expression level) and repression or inhibition of gene activity. In preferred embodiments of the invention, the therapeutic molecules (e.g. peptides) of the invention are repressors of gene expression or activity.

A nucleic acid "target", "target site" or "target sequence", as used herein, is a nucleic acid sequence to which a zinc finger peptide of the invention will bind, provided that conditions of the binding reaction are not prohibitive. A target site may be a nucleic acid molecule or a portion of a larger polynucleotide. Particularly suitable target sites comprise repetitive nucleic acid sequences; especially trinucleotide repeat sequences. Preferred target sequences in accordance with the invention include those defined by CAG-repeat sequences (e.g. CAGCAG . . . ; AGCAGC . . . ; and GCAGCA . . . ), and their complementary sequences, CTG-repeats (e.g. CTGCTG . . . ; TGCTGC . . . ; and GCTGCT . . . ). In accordance with the invention, a target sequence for a poly-zinc finger peptide of the invention may comprise a single contiguous nucleic acid sequence, or more than one non-contiguous nucleic acid sequence (e.g. two separate contiguous sequences, each representing a partial target site), which are interspersed by one or more intervening nucleotide or sequence of nucleotides. These terms may also be substituted or supplemented with the terms "binding site", "binding sequence", "recognition site" or recognition sequence", which are used interchangeably.

As used herein, "binding" refers to a non-covalent interaction between macromolecules (e.g. between a zinc finger peptide and a nucleic acid target site). In some cases binding will be sequence-specific, such as between one or more specific nucleotides (or base pairs) and one or more specific amino acids. It will be appreciated, however, that not all components of a binding interaction need be sequence-specific (e.g. non-covalent interactions with phosphate residues in a DNA backbone). Binding interactions between a nucleic acid sequence and a zinc finger peptide of the invention may be characterised by binding affinity and/or dissociation constant (Kd). A suitable dissociation constant for a zinc finger peptide of the invention binding to its target site may be in the order of 1 µM or lower, 1 nM or lower, or 1 pM or lower. "Affinity" refers to the strength of binding, such that increased binding affinity correlates with a lower Kd value. Zinc finger peptides of the invention may have DNA-binding activity, RNA-binding activity, and/or even protein-binding activity. Preferably zinc finger peptides of the invention are designed or selected to have sequence specific dsDNA-binding activity. Preferably, the target site for a particular zinc finger peptide is a sequence to which the zinc finger concerned is capable of nucleotide-specific binding. It will be appreciated, however, that depending on the amino acid sequence of a zinc finger peptide it may bind to or recognise more than one target sequence, although typically one sequence will be bound in preference to any other recognised sequences, depending on the relative specificity of the individual non-covalent interactions. Generally, specific binding is preferably achieved with a dissociation constant (Kd) of 1 nM or lower, 100 pM or lower; or 10 pM or lower. Preferably, a zinc finger peptide of the invention binds to a specific target sequence with a dissociation constant of 1 pM or lower; such as 0.1 pM or lower, or even 10 fM or lower.

By "non-target" it is meant that the nucleic acid sequence concerned is not appreciably bound by the relevant zinc finger peptide. In some embodiments it may be considered that, where a zinc finger peptide of the invention has a known sequence-specific target sequence, all other nucleic acid sequences may be considered to be non-target. From a practical perspective it can be convenient to define an interaction between a non-target sequence and a particular zinc finger peptide as being sub-physiological (i.e. not capable of creating a physiological response under physiological target sequence/zinc finger peptide concentrations). For example, if any binding can be measured between the zinc finger peptide and the non-target sequence, the dissociation constant (Kd) is typically weaker than 1 µM, such as 10 µM or weaker, 100 µM or weaker, or at least 1 mM.

The term "library" is used according to its common usage in the art, to denote a collection of different polypeptides or a collection of nucleic acids encoding different polypeptides. The zinc finger peptide frameworks of the invention are useful for creating libraries of zinc finger peptides having extended runs of adjacent zinc finger domains, comprising or encoding a repertoire of polypeptides of different sequences, each of which may have a different preferred binding sequence. Preferred zinc finger framework libraries comprise at least 8 adjacent zinc fingers, and more preferably at least 11 or 12 adjacent zinc fingers. In some embodiments a zinc finger framework library comprises 18 adjacent zinc finger domains. As used herein, a "naïve" library refers to a collection of different zinc finger peptides or corresponding encoding nucleic acids that has not been predetermined or selected to have a particular preferred target binding site.

Zinc Finger Peptides

The present invention relates to non-naturally occurring zinc fingers for binding to any desired nucleic acid sequence, and their use as therapeutic molecules; for example, in the treatment of HD. The invention further provides for the use of zinc finger modules in poly-zinc finger peptides to bind repetitive nucleic acid sequences, such as trinucleotide repeats, and particularly expanded CAG-repeats in genomic DNA sequences. Preferably, the poly-zinc finger peptides of the invention bind expanded CAG-repeats associated with mutated gene sequences in preferably and/or selectively over the shorter CAG-repeat sequences of normal genes.

A zinc finger is a relatively small polypeptide domain comprising approximately 30 amino acids, which folds to form an α-helix adjacent an antiparallel β-sheet (known as a ββα-fold). The fold is stabilised by the co-ordination of a zinc ion between four largely invariant (depending on zinc finger framework type) Cys and/or His residues, as described further below. Natural zinc finger domains have been well studied and described in the literature, see for example, Miller et al., (1985) *EMBO J.* 4: 1609-1614; Berg (1988) *Proc. Natl. Acad. Sci. USA* 85: 99-102; and Lee et al., (1989) *Science* 245: 635-637. A zinc finger domain recognises and binds to a nucleic acid triplet, or an overlapping quadruplet (as explained below), in a double-stranded DNA target sequence. However, zinc fingers are also known to bind RNA and proteins (Clemens, K. R. et al. (1993) Science 260: 530-533; Bogenhagen, D. F. (1993) *Mol. Cell. Biol.* 13: 5149-5158; Searles, M. A. et al. (2000) *J. Mol. Biol.* 301: 47-60; Mackay, J. P. & Crossley, M. (1998) *Trends Biochem. Sci.* 23: 1-4).

Zinc finger proteins generally contain strings or chains of zinc finger domains (or modules). Thus, a natural zinc finger protein may include 2 or more zinc finger domains, which may be directly adjacent one another (i.e. separated by a short (canonical) linker sequence), or may be separated by longer, flexible or structured polypeptide sequences. Directly adjacent zinc finger domains are expected to bind to contiguous nucleic acid sequences, i.e. to adjacent trinucleotides/triplets. In some cases cross-binding may also occur between adjacent zinc fingers and their respective target triplets, which helps to strengthen or enhance the recognition of the target sequence, and leads to the binding of overlapping quadruplet sequences (Isalan et al., (1997) *Proc. Natl. Acad. Sci. USA*, 94: 5617-5621). By comparison, distant zinc finger domains within the same protein may recognise (or bind to) non-contiguous nucleic acid sequences or even to different molecules (e.g. protein rather than nucleic acid).

The majority of the amino acid side chains in a zinc finger domain that are important for dsDNA base recognition are located on the α-helix of the finger. Conveniently, therefore, the amino acid positions in a zinc finger domain are numbered from the first residue in the α-helix, which is given the number (+)1; and the helix is generally considered to end at the final zinc-coordinating Cys or His residue, which is typically position+11. Thus, "−1" refers to the residue in the framework structure immediately preceding the first residue of the α-helix. As used herein, residues referred to as "++" are located in the immediately adjacent (C-terminal) zinc finger domain. Generally, nucleic acid recognition by a zinc finger module is achieved primarily by the amino acid side chains at positions −1, +3, +6 and ++2; although other amino acid positions may sometimes contribute to binding between the zinc finger and the target molecule. Therefore, it is convenient to define the sequence of a zinc finger domain from −1 to (+)6 (i.e. residues −1, 1, 2, 3, 4, 5 and 6) as a zinc finger "recognition sequence". The first invariant histidine residue that coordinates the zinc ion is position (+)7 of the zinc finger domain.

When binding to a nucleic acid sequence, a zinc finger domain generally interacts mainly with one strand of a double stranded nucleic acid molecule (the primary strand or sequence). However, there can be subsidiary interactions between amino acids of a zinc finger domain and the complementary (or secondary) strand of the double-stranded nucleic acid molecule. The α-helix of the zinc finger domain almost invariably lies within the major groove of dsDNA and aligns antiparallel to the target nucleic acid strand. Accordingly, the primary nucleic acid sequence is arranged 3' to 5' in order to correspond with the N-terminal to C-terminal sequence of the zinc finger peptide. Since nucleic acid sequences are conventionally written 5' to 3', and amino acid sequences N-terminus to C-terminus, when a target nucleic acid sequence and a zinc finger peptide are aligned according to convention, the primary interaction of the zinc finger peptide is with the complementary (or minus) strand of the nucleic acid sequence, since it is this strand which is aligned 3' to 5'. These conventions are followed in the nomenclature used herein.

Zinc finger peptides according to the invention are non-natural and suitably contain 3 or more, for example, 4, 6, 8, 9, 10, 11, 12, 13, 14, 15, 16, 17, 18 or more (e.g. up to approximately 30 or 32) zinc finger domains arranged adjacent one another in tandem. Such peptides may be referred to as "poly-zinc finger peptides". Particularly beneficial zinc finger peptides of the invention include at least 6 zinc finger domains, at least 11 or at least 12 zinc finger domains; and in some cases at least 18 zinc finger domains. The zinc finger peptides of the invention may bind to non-contiguous or contiguous nucleic acid binding sites. When targeted to non-contiguous binding sites, each sub-site (or half-site where there are two non-contiguous sequences) is suitably approximately 18 bases long, but may alternatively be approximately 12 or 24 bases long.

In (poly-)zinc finger peptides of the present invention, adjacent zinc finger domains are joined to one another by "linker sequences" that may be canonical, canonical-like, flexible or structured, as described, for example, in WO 01/53480 (Moore et al., (2001) *Proc. Natl. Acad. Sci. USA* 98: 1437-1441). Generally, a natural zinc finger linker sequence lacks secondary structure in the free form of the peptide. However, when the protein is bound to its target site a canonical linker is typically in an extended, linear conformation, and amino acid side chains within the linker may form local interactions with DNA. In a tandem array of zinc finger domains, the linker sequence is the amino acid sequence that lies between the last residue of the α-helix in an N-terminal zinc finger and the first residue of the β-sheet in the next (i.e. C-terminal adjacent) zinc finger. For the purposes of the present invention, the last amino acid of the α-helix in a zinc finger is considered to be the final zinc coordinating histidine (or cysteine) residue, while the first amino acid of the following finger is generally a tyrosine, phenylalanine or other hydrophobic residue.

Zinc Finger Peptide Frameworks and Libraries

Zinc finger peptides have proven to be extremely versatile scaffolds for engineering novel DNA-binding domains (e.g. Rebar & Pabo (1994) *Science* 263: 671-673; Jamieson et al., (1994) *Biochemistry* 33: 5689-5695; Choo & Klug (1994) *Proc. Natl. Acad. Sci. USA.* 91: 11163-11167; Choo et al., (1994) *Nature* 372: 642-645; Isalan & Choo (2000) *J. Mol. Biol.* 295: 471-477; and many others).

For specific biological functionality and therapeutic use, particularly in vivo (e.g. in gene therapy and transgenic animals), it is desirable that a poly-zinc finger peptide of the invention is able to target unique or virtually unique sites within any genome. For complex genomes, such as in humans, it is generally considered that an address of at least 16 bps is required to specify a potentially unique DNA sequence. Shorter DNA sequences have a significant probability of appearing several times in a genome, which increases the possibility of obtaining undesirable non-specific gene targeting and biological effects. Since individual zinc fingers generally bind to 3 consecutive nucleotides, 6 zinc finger domains with an 18 bp binding site could, in theory, be used for the specific recognition of a unique target sequence within any genome. Accordingly, a great deal of research has been carried out into so-called "designer transcription factors" for targeted gene regulation, which typically involve 4 or 6 zinc finger domains that may be arranged in tandem or in dimerisable groups (e.g. of 3-finger units). However, it has not previously been demonstrated that tandem arrays of more than 6 zinc finger domains, such as 8, 9, 10, 11, 12 or more (e.g. 15, 16 or 18) zinc fingers can be synthesised and expressed. Also, it has never previously been shown that such long arrays of non-natural zinc finger domains can have in vitro or in vivo (specific) nucleic acid binding activity. Certainly, it has not previously been reported that such extended arrays of zinc finger peptides can target genomic DNA sequences and even have gene modulation activity in vitro and/or in vivo.

In the present invention, novel extended zinc finger peptide frameworks comprising at least 4, at least 6, at least 10, at least 11, at least 12, or at least 18 zinc finger domains have been created. Thus, preferred zinc finger peptide frameworks of the invention comprise 6, 10, 11, 12 or 18 zinc finger domains.

The zinc finger peptide frameworks of the invention may comprise directly adjacent zinc finger domains having canonical (or canonical-like) linker sequences between adjacent zinc finger domains, such that they preferentially bind to contiguous nucleic acid sequences. Accordingly, a 6-zinc finger peptide (framework) of the invention is particularly suitable for binding to contiguous stretches of approximately 18 nucleic acid bases or more, particularly of the minus nucleic acid strand; a 12-zinc finger peptide (framework) of the invention is particularly suitable for binding to approximately 36 nucleic acid bases or more, which may be arranged as a contiguous stretch or as non-contiguous sub-sites of e.g. 18 nucleic acid bases; a 10-zinc finger peptide is suitable for binding approximately 30 nucleic acid bases or more; an 11-zinc finger peptide is suitable for binding approximately 33 nucleic acid bases or more, showing that odd numbers of long-finger chains are also functional; and an 18-zinc finger peptide (framework) of the invention is particularly suitable for binding to approximately 54 nucleic acid bases or more, which may be arranged contiguously or in non-contiguous sub-sites of e.g. 18 nucleic acid bases.

In some embodiments, one or more pairs of adjacent zinc finger domains may be separated by short flexible linker sequences (e.g. of 6 or 7 amino acids). In this case such poly-zinc finger peptides typically bind to contiguous DNA target sites, as indicated above. In some other embodiments, one or more pairs of adjacent zinc finger domains may be separated by longer flexible linker sequences, for example, comprising 8 or more amino acids, such as between 8 and 50 amino acids. Particularly suitable long flexible linkers have between approximately 11 and 40 amino acids, between 15 and 35 amino acids, or between 19 and 30 amino acids. Preferred long flexible linkers have 15, 18 or 29 amino acids. Adjacent zinc finger domains separated by long flexible linkers have the capacity to bind to non-contiguous binding sites in addition to the capacity to bind to contiguous binding sites. The length of the flexible linker may influence the length of DNA that may lie between such non-contiguous binding sub-sites.

The zinc finger frameworks of the invention may comprise two or more (e.g. 2, 3 or 4) arrays of 4, 6 or 8 directly adjacent zinc finger domains separated by long flexible (or structured) linkers. Preferably, such extended (poly-)zinc finger peptides are arranged in multiple arrays of 6-finger units separated by long flexible linkers.

The inventors have shown for the first time that such extended zinc finger peptides of more than 6 zinc fingers can exhibit specific and high affinity binding to desired target sequences, both in vitro and in vivo. Furthermore, it has been demonstrated that these extended zinc finger peptides can be stably expressed within a target cell, can be non-toxic to the target cell, and can have a specific and desired gene modulation activity.

The extended zinc finger peptides of the invention are particularly suitable for binding to repeat sequences (e.g. trinucleotide repeats) in target genes. Suitable target repeat sequences comprise at least 10 trinucleotide repeats, at least 12 trinucleotide repeats, or at least 20 trinucleotide repeats. Beneficially, there are at least 22 trinucleotide repeats, at least 29 trinucleotide repeats or more.

In one embodiment, extended zinc finger peptides of the invention bind to sequences within expanded CAG and/or CTG-repeat sequences in double-stranded DNA e.g. DNA molecules, fragments, gene sequences or chromatin. Suitably, the binding site comprises repeats of 5'-GCA-3' and/or 5'-GCT-3'. Thus, the binding site preferably comprises repeats of the sequence 5'-$GC^{T}/_{A}$-3'. Desirably, target sequences for the preferred extended zinc finger peptides of the invention comprise 22 or more contiguous CAG (or CTG) repeats, such as at least 35 contiguous CAG (or CTG) repeats, at least 63 contiguous CAG (or CTG) repeats, at least 104 contiguous CAG (or CTG) repeats, or at least 111 contiguous CAG (or CTG) repeats.

A surprising advantage of the zinc finger peptides of one embodiment of the invention is that they bind to longer arrays of CAG or CTG-repeat sequences in preference to shorter arrays. Accordingly, the CAG (or CTG) targeting zinc finger peptides of the invention bind more effectively (e.g. with higher affinity or greater gene modulation ability) to expanded CAG or CTG-repeat sequences containing at least 22 repeats, compared to sequences containing e.g. 10 or less repeats. Similarly, sequences containing at least 35 CAG or CTG-repeats may be bound preferentially over sequences containing 22 or less repeats (including 10 or less); sequences containing at least 63 CAG or CTG-repeats may be bound preferentially over sequences containing 35 or less repeats (including 22 or less, or 10 or less); and sequences containing at least 104 CAG or CTG-repeats may be bound preferentially over sequences containing 63 or less repeats (including 35 or less, 22 or less, or 10 or less).

The extended zinc finger peptide frameworks of the invention are also suitable for the generation of naïve zinc finger peptide libraries, which can be screened or otherwise tested for desirable properties, such as binding affinity to a chosen target sequence (such as DNA or RNA). Therefore, in one aspect, the present invention relates to an extended zinc finger peptide framework that can form a scaffold for the selection or design of artificial zinc finger transcription factors and/or DNA binding proteins. For example, the extended zinc finger array framework may comprise 10, 11, 12 or more (such as 18) zinc finger domains, which may be diversified at one or more amino acid position.

There are a number of natural zinc finger frameworks known in the art, and any of these frameworks may be suitable for use in the extended zinc finger peptide frameworks of the invention. In general, a natural zinc finger framework has the sequence, Formula 1: $X_{0-2} \, C \, X_{1-5} \, C \, X_{9-14} \, H \, X_{3-6} \, ^{H}/_C$; or Formula 2: $X_{0-2} \, C \, X_{1-5} \, C \, X_{2-7} \, X^{-1} \, X^{+1} \, X^{+2} \, X^{+3} \, X^{+4} \, X^{+5} \, X^{+6} \, H \, X_{3-6} \, ^{H}/_C$ where X is any amino acid, the numbers in subscript indicate the possible numbers of residues represented by X, and the numbers in superscript indicate the position of the amino acid in the -helix. In one embodiment of the invention, the extended zinc finger peptide framework is based on an array of zinc finger domains of Formula 1 or 2. Alternatively, the zinc finger motif may be represented by the general sequence, Formula 3: $X_2 \, C \, X_{2,4} \, C \, X_{12} \, H \, X_{3,4,5} \, ^{H}/_C$; or Formula 4 (SEQ ID NO: 112): $X_2 \, C \, X_{2,4} \, C \, X_5 \, X^{-1} \, X^{+1} \, X^{+2} \, X^{+3} \, X^{+4} \, X^{+5} \, X^{+6} \, H \, X_{3,4,5} \, ^{H}/_C$. Still more preferably the zinc finger motif may be represented by the general sequence, Formula 5: $X_2 \, C \, X_2 \, C \, X_{12} \, H \, X_3 \, H$; or Formula 6 (SEQ ID NO: 113): $X_2 \, C \, X_2 \, C \, X_5 \, X^{-1} \, X^{+1} \, X^{+2} \, X^{+3} \, X^{+4} \, X^{+5} \, X^{+6} \, H \, X_3 \, H$. Accordingly, an extended zinc finger peptide framework of the invention may be based on zinc finger domains of Formulas 1 to 6, or combinations of Formulas 1 to 6, joined together in an array using the linker sequences described herein.

In these formulas, the fixed C and H residues coordinate the zinc ion to stabilise the zinc finger structure: the first H residue is position +7 of the α-helix. Particularly preferred positions for diverisification within the zinc finger domain frameworks of the invention are those within or adjacent the α-helix, for example, positions −1, 2, 3 and 6.

In one embodiment of the invention, the extended zinc finger peptide framework comprises at least 11 zinc finger domains of one of Formulas 1 to 6, joined together by linker sequences, i.e. Formula 7: [(Formula 1-6)-linker]$_n$-(Formula 1-6)], where n is≥10, such as between 10 and 31. As indicated, in Formula 7 any combination of Formulas 1 to 6 may be used. In another embodiment the extended zinc finger peptide framework comprises between 10 and 18 (e.g. 11 to 18) zinc finger domains of the above Formulas. Suitably, therefore, n is 9 to 17 (e.g. 10 to 17); more suitably n is 9, 10, 11, 13, 14, 15 or 17; and preferably n is 10, 11 or 17.

In a preferred embodiment of the invention, the recognition sequence of one or more of the zinc finger domains (i.e. positions $X^{-1}, X^{+1}, X^{+2}, X^{+3}, X^{+4}, X^{+5}$ and $X^{+6}$ in Formulas 2, 4 and 6 above is represented by the amino acid sequence of SEQ ID NO: 101. In some embodiments, the recognition sequence of one or more zinc finger domain is selected from SEQ ID NO: 1, SEQ ID NO: 102, SEQ ID NO: 103, SEQ ID NO: 104, SEQ ID NO: 105, SEQ ID NO: 106, and SEQ ID NO: 107 or combinations thereof. In a particularly preferred embodiment, the recognition sequence of one or more of the zinc finger domains is represented by the amino acid sequence QRATLQR (SEQ ID NO: 1). Alternative recognition sequences that bind to CAG- or CTG-repeat sequences are also encompassed, such as those having one or more, such as 1, 2 or 3 mutations (e.g. conservative substitutions) to SEQ ID NO: 1. Thus, in one embodiment, there is provided an engineered zinc finger (DNA-binding) peptide comprising at least 10 zinc finger domains, wherein at least one zinc finger recognition sequence has the sequence of SEQ ID NO: 1 and/or SEQ ID NO: 101. Beneficially, the engineered zinc finger peptide of the invention comprises at least 11 zinc finger recognition sequences of SEQ ID NO: 1 and/or SEQ ID NO: 101. Suitably, the zinc finger peptide comprises between 11 and 18 (e.g. 12) zinc finger recognition sequences of SEQ ID NO: 1 and/or SEQ ID NO: 101. In any of the embodiments of the invention it will be understood that one or more recognition sequence of SEQ ID NO: 1 may be replaced with a sequence selected from SEQ ID NO: 102, SEQ ID NO: 103, SEQ ID NO: 104, SEQ ID NO: 105, SEQ ID NO: 106, and SEQ ID NO: 107 without substantially changing the nucleic acid recognition and binding characteristics of the ZFP, and such alternative ZFPs are encompassed within the scope of the invention.

The zinc finger peptides of the invention preferably bind to CAG-repeat sequences and/or CTG-repeat sequences; and more preferably to human expanded htt gene sequences.

As already described, adjacent zinc finger domains are joined together by linker sequences. In a natural zinc finger protein, threonine is often the first residue in the linker, and proline is often the last residue of the linker. On the basis of sequence homology, the canonical natural linker sequence is considered to be -TGEKP- (Linker 1 or L1; SEQ ID NO: 20). However, natural linkers can vary greatly in terms of amino acid sequence and length. Therefore, a common consensus sequence based on natural linker sequences may be represented by -TG$^E$/$_Q$$^K$/$_R$P- (Linker 2 or L2; SEQ ID NO: 21), and this sequence is preferred for use as a "canonical" (or "canonical-like") linker in accordance with the invention.

However, in extended zinc finger arrays of e.g. 4 or more zinc finger domains, it has been shown that it can be beneficial to periodically disrupt the canonical linker sequence, when used between adjacent zinc fingers in an array, by adding one or more amino acid residue (e.g. Gly and/or Ser), so as to create sub-arrays of zinc finger domains (e.g. groups of 2 or 3) within the array (Moore et al., (2001) Proc. Natl. Acad. Sci. USA 98: 1437-1441; and WO 01/53480). Therefore, suitable linker sequences for use in accordance with the invention include canonical linker sequences of 5 amino acids (e.g. Linker 1 or Linker 2, above), or related canonical-like linker sequences of between 5 and 7 amino acids.

Canonical-like linkers for use in accordance with the invention may suitably be based on the sequence, -TG$^G$/$_S$$^E$/$_Q$$^K$/$_R$P- (Linker 3 or L3; SEQ ID NO: 22). Preferred canonical-like linkers thus include the specific sequences: TGGERP (SEQ ID NO: 23), TGSERP (SEQ ID NO: 24), TGGQRP (SEQ ID NO: 25), TGSQRP (SEQ ID NO: 26), TGGEKP (SEQ ID NO: 27), TGSEKP (SEQ ID NO: 28), TGGQKP (SEQ ID NO: 29), or TGSQKP (SEQ ID NO: 30). A particularly preferred canonical-like linker is TGSERP (Linker 4 or L4; SEQ ID NO: 24). However, other linker sequences may also be used between one or more pairs of zinc finger domains, for example, linkers of the sequence -TG($^G$/$_S$)$_{0-2}$$^E$/$_Q$$^K$/$_R$P- (Linker 5 or L5; SEQ ID NO: 33) or -T($^G$/$_S$)$_{0-2}$G$^E$/$_Q$$^K$/$_R$P- (Linker 6 or L6; SEQ ID NO: 34).

In some embodiments still longer flexible linkers of 8 or more amino acids may be used, as previously described. Linkers of 8 amino acids include the sequences -TG($^G$/$_S$)$_3$$^E$/$_Q$$^K$/$_R$P- (SEQ ID NO: 31) and -T($^G$/$_S$)$_3$G$^E$/$_Q$$^K$/$_R$P- (L12; SEQ ID NO: 32). Exemplary long flexible linkers are: LRQKDGGGGSQLVGTAERP (Linker 7 or L7; SEQ ID NO: 35), LRQKDGGGGSGGGGSQLVGTAERP (Linker 8 or L8; SEQ ID NO: 36), LRQKDGGGGSGGGGSGGGGSQLVGTAERP (Linker 9 or L9; SEQ ID NO: 37), LRQKDGGGSQLVGTAERP (Linker 10 or L10; SEQ ID NO: 38) and LRQKDGGGS-GTAERP (Linker 11 or L11; SEQ ID NO: 39).

The present inventors have shown that by selecting appropriate linker sequences and suitable combinations of linker sequences within an array of zinc fingers, extended arrays of zinc finger peptides of at least 10 zinc fingers [such as 10, 11, 12 or 18] can be synthesised, expressed and can have selective gene targeting activity. The extended arrays of zinc finger peptides of the invention are preferably arranged in tandem. Such 11, or 12-zinc finger peptides can recognise and specifically bind 33 or 36 nucleic acid residues, respectively, and longer arrays (such as 18-zinc finger peptides) recognise still longer nucleic acid sequences. In this way, the extended zinc finger peptides of the invention can be targeted to unique genomic sequences. Moreover, the sequence recognition length provides a greater number of unique sequence combinations within the recognition sequence, which can potentially provide for greater selectivity for the target sequence to distinguish over non-target sequences. In this way the zinc finger peptides of the invention have the potential to be more specific than any artificial transcription factor synthesised to date.

In addition, a significant increase in binding affinity might also be expected, compared to zinc finger peptides with fewer fingers. For example, where a 3-finger peptide (with a 9 bp recognition sequence) binds DNA with nanomolar affinity, a 6-finger peptide might be expected to bind an 18 bp sequence with an affinity of between $10^{-9}$ and $10^{-18}$ M, depending on the arrangement and sequence of zinc finger peptides. To optimise both the affinity and specificity of 6-finger peptides, a fusion of three 2-finger domains has been shown to be advantageous (Moore et al., (2001) *Proc. Natl. Acad. Sci. USA* 98: 1437-1441; and WO 01/53480). Therefore, in some embodiments of the invention, the zinc finger peptides of the invention comprise sub-arrays of 2-finger units arranged in tandem. In other embodiments the zinc finger peptides of the invention comprise sub-arrays of 3-finger units arranged in tandem.

Accordingly, the extended zinc finger framework of the invention may comprise a sequence selected from:

SEQ ID NO: 2 N'-[(Formula 2)-$X_6$]$_{n0}$-{[(Formula 2)-$X_5$-(Formula 2)-$X_6$]$_{n1}$-[(Formula 2)-$X_5$-(Formula 2)-$X_L$]}$_{n2}$-[(Formula 2)-$X_5$-(Formula 2)-$X_6$]$_{n3}$-[(Formula 2)-$X_5$-(Formula 2)]-[$X_6$-(Formula 2)-]$_{n4}$-C', wherein n0 is 0 or 1, n1 is from 1 to 4, n2 is 1 or 2, n3 is from 1 to 4, n4 is 0 or 1, $X_5$ is a linker sequence of 5 amino acids, $X_6$ is a linker sequence of 6 or 7 amino acids, and $X_L$ is a linker of at least 8 amino acids;

SEQ ID NO: 3 N'-[(Formula 1-6)-L3]$_{n0}$-{[(Formula 1-6)-L2-(Formula 1-6) -L3]$_{n1}$-[(Formula 1-6)-L2-(Formula 1-6)-$X_L$]}$_{n2}$-[(Formula 1-6)-L2-(Formula 1-6)-L3]$_{n3}$-[(Formula 1-6)-L2-(Formula 1-6)]-[L3-(Formula 1-6)]$_{n4}$-C' where n0, n1, n2, n3, n4 and $X_L$ are as defined above;

SEQ ID NO: 4 N'-[(Formula 1-6)-L4]$_{n0}$-{[(Formula 1-6)-L1-(Formula 1-6) -L4]$_{n1}$-[(Formula 1-6)-L1-(Formula 1-6)-$X_L$]}$_{n2}$-[(Formula 1-6)-L1-(Formula 1-6)-L4]$_{n3}$-[(Formula 1-6)-L1-(Formula 1-6)]-[L4-(Formula 1-6)]$_{n4}$-C', where n0, n1, n2, n3, n4 and $X_L$ are as defined above;

SEQ ID NO: 5 N'-[(Formula 6)-L4]$_{n0}$-{[(Formula 6)-L1-(Formula 6)-L4]$_{n1}$-[(Formula 6)-L1-(Formula 6)-$X_L$]}$_{n2}$-[(Formula 6)-L1-(Formula 6)-L4]$_{n3}$-[(Formula 6)-L1-(Formula 6)]-[L4-(Formula 6)]$_{n4}$-C', where n0, n1, n2, n3, n4 and $X_L$ are as defined above.

For the avoidance of doubt, hyphens ("-") in the Formulas and SEQ ID NOs of the invention represent linkages only, and so these Formulas and SEQ IDs may also be represented without hyphens.

Preferably in SEQ ID NOs: 2 to 5, n0 is 0 or 1, n1 is from 1 to 3, n2 is 1 or 2, n3 is 2 or 3, n4 is 0 and $X_L$ is about 8 to 50. More preferably, n0 is 0, n1 is 2 or 3, n2 is 1 or 2, n3 is 2 and n4 is 0, and/or $X_L$ is about 11 to 40 amino acids. Still more preferably, n0 is 0, n1 is 2, n2 is 1 or 2, n3 is 2 and n4 is 0; and/or $X_L$ is about 15 to 35 amino acids. Still more preferably $X_L$ is about 15 to 29 amino acids. Most preferably $X_L$ is selected from L7, L8, L9, L10, L11 and L12.

Accordingly, the invention further provides methods for the construction and use of poly-zinc finger peptides comprising at least 6, and preferably at least 11 or 12 (e.g. 11, 12 or 18) zinc finger domains. The methods of the invention are particularly suitable for constructing arrays of identical zinc finger domains, which can bind to repeat trinucleotide target sequences.

In the zinc finger frameworks above, the total number of zinc finger domains is preferably from 11 to 18 and the zinc finger recognition sequence is preferably SEQ ID NO: 1. Preferred zinc finger peptides have 6, 11, 12 or 18 zinc finger domains, and comprise the sequences of SEQ ID NO: 8, SEQ ID NO: 10, SEQ ID NO: 12 or SEQ ID NO: 14 respectively (see Table 1).

The invention also encompasses nucleic acid molecules that encode the peptide sequences of the invention. Preferred zinc finger peptide encoding sequences comprise SEQ ID NOs: 9, 11, 13 and 15 which encode the zinc finger peptides of SEQ ID NOs: 8, 10, 12 and 14, respectively.

It will be appreciated that the zinc finger peptide framework sequences of the invention may further include optional (N-terminal) leader sequences, such as: amino acids to aid expression (e.g. N-terminal Met-Ala dipeptide); purification tags (e.g. FLAG-tags); and localisation/targeting sequences (e.g. nuclear localisation sequences (NLS), such as PKKKRKV; (SEQ ID NO: 40). Also, the peptides may optionally include additional C-terminal sequences, such as: linker sequences for fusing zinc finger domains to effector molecules; and effector molecules. Other sequences may be employed for cloning purposes. The sequences of any N- or C-terminal sequences may be varied, typically without altering the binding activity of the zinc finger framework, and such variants are encompassed within the scope of the invention.

Zinc finger frameworks of the invention may be used to design or select for zinc finger peptide arrays that target any desired nucleic acid sequence. In this case, the zinc finger frameworks may be diversified at one or more positions. In some embodiments the framework is diversified at one or more of amino acids positions −1, 1, 2, 3, 4, 5 and 6 of Formulas 1 to 6, and hence of SEQ ID NOs: 2 to 5. The polypeptide sequence changes may conveniently be achieved by diversifying the nucleic acid sequence encoding the zinc finger peptide frameworks at the codons for at least one of those positions, so as to encode more than one polypeptide variant. In another embodiment, the framework nucleic acid or peptide is varied specifically or randomly at one or more (e.g. all) of positions −1, 2, 3 and 6. In yet another embodiment, the framework is varied at positions −1 3 and 6. Beneficially, at least 2, at least 3, at least 4, at least 5, or at least 6 of the positions in the recognition sequence of each zinc finger domain are diversified. All such nucleic acid and polypeptide variants are encompassed within the scope of the invention.

Hence, in one aspect the invention relates to a naïve library of nucleic acids or polypeptides comprising more than one zinc finger peptide or encoding nucleic acid sequence, which allow selection of zinc finger peptides having desirable properties (such as binding affinity for a chosen target nucleic acid sequence), from a suitable library screening/selection method. For the purposes of this invention, a library having a mixture of peptides or nucleic acids that has not been optimised or selected to have a particular functionality is termed herein a "naïve" library. A potential advantage of the zinc finger peptide framework of the invention is that target sites that may be bound by individual members of the framework library may not be restricted to a particular type or conformation of molecule (e.g. double stranded DNA). Thus, any desirable target molecule or sequence may be recognised (i.e. bound), such as nucleic acids (e.g. DNA or RNA), proteins or peptides. A preferred target molecule is a double stranded nucleic acid, and is most suitably DNA.

The amino acid residues at each of the diversified positions may be non-selectively randomised, i.e. by allowing the amino acid at the position concerned to be any of the 20 common naturally occurring amino acids; or may be selectively randomised, i.e. by allowing the specified amino acid to be any one from a defined sub-group of the 20 naturally occurring amino acids. It will be appreciated that one convenient way of creating a library of mutant peptides with randomised amino acids at each selected location, is to randomise the nucleic acid codon of the corresponding nucleic acid sequence that encodes the selected amino acid. On the other hand, given the knowledge that has now accumulated in relation to the sequence specific binding of zinc finger domains to nucleic acids, in some embodiments it may be convenient to select a specific amino acid (or small sub-group of amino acids) at one or more chosen positions in the zinc finger domain, for example, where it is known that a specific amino acid provides optimal binding to a particular nucleotide residue in a specific target sequence. Such peptides or frameworks are the result of "intelligent" design. Conveniently the whole of the zinc finger recognition sequence may be selected by intelligent design and inserted/incorporated into an appropriate zinc finger framework. The person of skill in the art is well aware of the codon sequences that may be used in order to specify one or more than one particular amino acid residue within a library. Non-randomised amino acid positions in each zinc finger domain may be chosen from known wild-type or artificial zinc finger structures.

Another aspect of the present invention is directed towards the selection, identification and/or characterisation of zinc finger peptides having a desired property, from a naïve zinc finger framework of the invention. A naïve library comprises a plurality of nucleic acid sequences (e.g. at least $10^6$, $10^8$, $10^9$, $10^{12}$ or more different coding sequences) that can be expressed and screened to identify zinc finger peptides having the desired property.

The invention also encompasses derivatives of the zinc finger peptides of the invention. In this regard, it will be appreciated that modifications, such as amino acid substitutions may be made at one or more positions in the peptide without adversely affecting its physical properties (such as binding specificity or affinity). By "derivative" of a zinc finger peptide it is meant a peptide sequence that has the selected desired activity (e.g. binding affinity for a selected target sequence), but that further includes one or more mutations or modifications to the primary amino acid sequence. Thus, a derivative of the invention may have one or more (e.g. 1, 2, 3, 4, 5 or more) chemically modified amino acid side chains, such as pegylation, sialylation and glycosylation modifications. In addition or alternatively, a derivative may contain one or more (e.g. 1, 2, 3, 4, 5 or more) amino acid mutations, substitutions or deletions to the primary sequence of a selected zinc finger peptide. Accordingly, the invention encompasses the results of maturation experiments conducted on a selected zinc finger peptide or a zinc finger peptide framework to improve or change one or more characteristics of the initially identified peptide. By way of example, one or more amino acid residues of a selected zinc finger domain may be randomly or specifically mutated (or substituted) using procedures known in the art (e.g. by modifying the encoding DNA or RNA sequence). The resultant library or population of derivatised peptides may further be selected—by any known method in the art—according to predetermined requirements: such as improved specificity against particular target sites; or improved drug properties (e.g. solubility, bioavailability, immunogenicity etc.). Peptides selected to exhibit such additional or improved characteristics and that display the activity for which the peptide was initially selected are derivatives of the zinc finger peptides of the invention and also fall within the scope of the invention.

Zinc Finger Peptide Modulators and Effectors

While the zinc finger peptides of the invention may have useful biological properties in isolation, they can also be given useful biological functions by the addition of effector domains. Therefore, in some cases it is desirable to conjugate a zinc finger peptide of the invention to one or more non-zinc finger domain, thus creating chimeric or fusion zinc finger peptides. It may also be desirable, in some instances, to create a multimer (e.g. a dimer), of a zinc finger peptide of the invention—for example, to bind more than one target sequence simultaneously.

Thus, having identified a desirable zinc finger peptide, an appropriate effector or functional group may then be attached, conjugated or fused to the zinc finger peptide. The resultant protein of the invention, which comprises at least a zinc finger portion (of more than one zinc finger domain) and a non-zinc finger effector domain, portion or moiety may be termed a "fusion", "chimeric" or "composite" zinc finger peptide. Beneficially, the zinc finger peptide will be linked to the other moiety via sites that do not interfere with the activity of either moiety.

A "non-zinc finger domain" (or moiety) as used herein, refers to an entity that does not contain a zinc finger ($\beta\beta\alpha$) fold. Thus, non-zinc finger moieties include nucleic acids and other polymers, peptides, proteins, peptide nucleic acids (PNAs), antibodies, antibody fragments, and small molecules, amongst others.

Beneficially, chimeric zinc finger peptides or fusion proteins of the invention are used to up- or down-regulate desired target genes, in vitro or in vivo. Thus, potential effector domains include transcriptional repressor domains, transcriptional activator domains, transcriptional insulator domains, chromatin remodelling, condensation or decondensation domains, nucleic acid or protein cleavage domains, dimerisation domains, enzymatic domains, signalling/targeting sequences or domains, or any other appropriate biologically functional domain. Other domains that may also be appended to zinc finger peptides of the invention (and which have biological functionality) include peptide sequences involved in protein transport, localisation sequences (e.g. subcellular localisation sequences, nuclear localisation, protein targeting) or signal sequences. Zinc finger peptides can also be fused to epitope tags (e.g. for use to signal the presence or location of a target nucleotide sequence recognised by the zinc finger peptide. Functional fragments of any such domain may also be used.

The expression of many genes is also achieved by controlling the fate of the associated RNA transcript. RNA molecules often contain sites for RNA-binding proteins, which determine RNA half-life and hence, levels of protein expression. Therefore, zinc finger peptide modulators of the invention may also control gene expression by specifically targeting RNA transcripts to either increase or decrease their half-life within a cell.

Beneficially, zinc finger peptides and fusion proteins of the invention have transcriptional activity and, therefore, preferred biological effector domains include transcriptional modulation domains such as transcriptional activators and transcriptional repressors, as well as their functional fragments. The effector domain can be directly derived from a basal or regulated transcription factor such as, for example, transactivators, repressors, and proteins that bind to insulator or silencer sequences (see Choo & Klug (1995) *Curr. Opin. Biotech.* 6: 431-436; Choo & Klug (1997) *Curr. Opin. Str. Biol.* 7:117-125; and Goodrich et al. (1996) *Cell* 84: 825-830); or from receptors such as nuclear hormone receptors (Kumar & Thompson (1999) *Steroids* 64: 310-319); or co-activators and co-repressors (Ugai et al. (1999) *J. Mol. Med.* 77: 481-494).

Other useful functional domains for control of gene expression include, for example, protein-modifying domains such as histone acetyltransferases, kinases, methylases and phosphatases, which can silence or activate genes by modifying DNA structure or the proteins that associate with nucleic acids (Wolffe (1996) *Science* 272: 371-372; and Hassig et al., (1998) *Proc. Natl. Acad. Sci. USA* 95: 3519-3524). Additional useful effector domains include those that modify or rearrange nucleic acid molecules such as methyltransferases, endonucleases, ligases, recombinases, and nucleic acid cleavage domains (see for example, Smith et al. (2000) *Nucleic Acids Res.,* 17: 3361-9; WO 2007/139982 and references cited therein).

Potential transcriptional/gene activation domains for fusing to zinc finger peptides of the invention include the VP64 domain (see Seipel et al., (1996) *EMBO J.* 11: 4961-4968) and the herpes simplex virus (HSV) VP16 domain (Hagmann et al. (1997) *J. Virol.* 71: 5952-5962; Sadowski et al. (1988) *Nature* 335: 563-564); and transactivation domain 1 and/or 2 of the p65 subunit of nuclear factor-κB (NFκB; Schmitz et al. (1995) *J. Biol. Chem.* 270: 15576-15584).

A preferred transcriptional repression domain is the Kruppel-associated box (KRAB) domain, which is a powerful repressor of gene activity. In some preferred embodiments, therefore, zinc finger peptides or frameworks of the invention are fused to the KRAB repressor domain from the human Kox-1 protein in order to repress a target gene activity (e.g. see Thiesen et al. (1990) *New Biologist* 2: 363-374). Fragments of the Kox-1 protein comprising the KRAB domain, up to and including full-length Kox protein may be used as transcriptional repression domains, as described in Abrink et al. (2001) *Proc. Natl. Acad. Sci. USA,* 98: 1422-1426. A useful Kox-1 domain sequence is shown in Table 2 (SEQ ID NO: 16, SEQ ID NO: 17). Other transcriptional repressor domains known in the art may alternatively be used, such as the engrailed domain, the snag domain, and the transcriptional repression domain of v-erbA.

All known methods of conjugating an effector domain to a peptide sequence are incorporated. The term "conjugate" is used in its broadest sense to encompass all methods of attachment or joining that are known in the art, and is used interchangeably with the terms such as "linked", "bound", "associated" or "attached". The effector domain(s) can be covalently or non-covalently attached to the binding domain: for example, where the effector domain is a polypeptide, it may be directly linked to a zinc finger peptide (e.g. at the C-terminus) by a flexible or structured amino acid (linker) sequence encoded by the corresponding nucleic acid molecule. One suitable linker sequence for joining an effector domain to the C-terminus of a zinc finger peptide is illustrated in Table 2 (SEQ ID NO: 18, SEQ ID NO: 19). Alternatively, a synthetic non-amino acid or chemical linker may be used, such as polyethylene glycol, a maleimide-thiol linkage (useful for linking nucleic acids to amino acids), or a disulphide link. Synthetic linkers are commercially available, and methods of chemical conjugation are known in the art.

Non-covalent linkages between a zinc finger peptide and an effector domain can be formed using, for example, leucine zipper/coiled coil domains, or other naturally occurring or synthetic dimerisation domains (Luscher & Larsson (1999) *Oncogene* 18: 2955-2966; and Gouldson et al. (2000) *Neuropsychopharm.* 23: S60-S77. Other non-covalent means of conjugation may include a biotin-(strept)avidin link or the like. In some cases, antibody (or antibody fragment)-antigen interactions may also be suitably employed, such as the fluorescein-antifluorescein interaction.

To cause a desired biological effect via modulation of gene expression, zinc finger peptides or their corresponding fusion peptides are allowed to interact with, and bind to, one or more target nucleotide sequence associated with the target gene, either in vivo or in vitro depending to the application. Beneficially, therefore, a nuclear localisation domain is attached to the DNA binding domain to direct the protein to the nucleus.

When the target sequence is DNA, preferred DNA regions from which to effect the up- or down-regulation of specific genes include promoters, enhancers or locus control regions (LCRs). Other suitable regions within genomes, which may provide useful targets for zinc finger peptides of the invention, include telomeres and centromeres. In one embodiment, the genomic DNA target sequence comprises a trinucleotide repeat sequence comprising at least 10 such repeats. In another embodiment, the genomic DNA target sequence comprises a CAG-repeat sequence as found in expanded CAG-repeats of mutant genes. In yet another embodiment the DNA target sequence comprises a CTG-repeat sequence, which is the complement of an expanded CAG-repeat sequence.

Nucleic Acids and Peptide Expression

The zinc finger peptides according to the invention and, where appropriate, the zinc finger peptide conjugate/effector molecules of the invention may be produced by recombinant DNA technology and standard protein expression and purification procedures. Thus, the invention further provides nucleic acid molecules that encode the zinc finger peptides of the invention as well as their derivatives; and nucleic acid constructs, such as expression vectors that comprise nucleic acids encoding peptides and derivatives according to the invention.

For instance, the DNA encoding the relevant peptide can be inserted into a suitable expression vector (e.g. pGEM®, Promega Corp., USA), where it is operably linked to appropriate expression sequences, and transformed into a suitable host cell for protein expression according to conventional techniques (Sambrook J. et al., Molecular Cloning: a Laboratory Manual, Cold Spring Harbor Press, Cold Spring Harbor, N.Y.). Suitable host cells are those that can be grown in culture and are amenable to transformation with exogenous DNA, including bacteria, fungal cells and cells of higher eukaryotic origin, preferably mammalian cells.

To aid in purification, the zinc finger peptides (and corresponding nucleic acids) of the invention may include a purification sequence, such as a His-tag. In addition, or alternatively, the zinc finger peptides may, for example, be grown in fusion with another protein and purified as insoluble inclusion bodies from bacterial cells. This is particularly convenient when the zinc finger peptide or effector moiety may be toxic to the host cell in which it is to be expressed. Alternatively, peptides of the invention may be synthesised in vitro using a suitable in vitro (transcription and) translation system (e.g. the *E. coli* S30 extract system, Promega corp., USA).

The term "operably linked", when applied to DNA sequences, for example in an expression vector or construct, indicates that the sequences are arranged so that they function cooperatively in order to achieve their intended purposes, i.e. a promoter sequence allows for initiation of transcription that proceeds through a linked coding sequence as far as the termination sequence.

It will be appreciated that, depending on the application, the zinc finger peptide or fusion protein of the invention may comprise an additional peptide sequence or sequences at the N- and/or C-terminus for ease of protein expression, cloning, and/or peptide or RNA stability, without changing the sequence of any zinc finger domain. For example, suitable N-terminal leader peptide sequences are MA, MAERP (SEQ ID NO: 41) or MAEERP (SEQ ID NO: 42).

In some applications it may be desirable to control the expression of zinc finger (fusion) polypeptides of the invention by tissue specific promoter sequences or inducible promoters, which may provide the benefits of organ or tissue specific and/or inducible expression of polypeptides of the invention. These systems may be particularly advantageous for in vivo applications and gene therapy. Examples of tissue-specific promoters include the human CD2 promoter (for T-cells and thymocytes, Zhumabekov et al. (1995) *J. Immunological Methods* 185: 133-140); the alpha-calcium-calmodulin dependent kinase II promoter (for hippocampus and neocortex cells, Tsien et al. (1996) *Cell* 87: 1327-1338); the whey acidic protein promoter (mammary gland, Wagner et al. (1997) *Nucleic Acids Res.* 25: 4323-4330); the mouse myogenin promoter (skeletal muscle, Grieshammer et al. (1998) *Dev. Biol.* 197: 234-247); and many other tissue specific promoters that are known in the art. For Huntington's disease gene therapy, it is desirable to infect particular parts of the brain (the striatum). Therefore, AAV2/1 subtype vectors (see e.g. *Molecular Therapy* (2004) 10: 302-317) are ideal for this purpose and can be used with a strong AAV promoter included in the vectors.

Suitable inducible systems may use small molecule induction, such as the tetracycline-controlled systems (tet-on and tet-off), the radiation-inducible early growth response gene-1 (EGR1) promoter, and any other appropriate inducible system known in the art.

Expression and Characterisation of Zinc Finger Peptides from Libraries

Zinc finger peptides having desirable binding activity may be selected by screening libraries of peptides from a zinc finger peptide framework of the invention. In accordance with one aspect of the invention, nucleic acid libraries encoding a plurality of zinc finger peptides are expressed, and the synthesised peptides are initially selected for their ability to bind a desired target sequence. The screening may be performed using any library generation and selection system known to the person of skill in the art, such as those identified below.

One approach is to produce a mixed population of candidate peptides by cloning a randomised oligonucleotide library into an Ff filamentous phage gene, which allows large peptides to be expressed on the surface of the bacteriophage (H. Lowman (1997) *Ann. Rev. Biophys. Biomol. Struct.*, 26: 401-424; and G. Smith et al. (1993) *Meth. Enz.*, 217: 228-257). Randomised peptide libraries up to 38 amino acids in length have also been made, and longer peptides are achievable using this system. The peptide libraries that are produced are then typically mixed with a pre-selected matrix-bound nucleic acid target sequence. Peptides that bind are isolated, and their sequences are determined. From this information new peptides are synthesised and their biological properties can be assessed.

A potential disadvantage of the above procedures is that the size of the libraries that are typically generated with both phage display and chemical synthesis is limited to within the $10^6$-$10^9$ range. This limitation can result in the isolation of peptides of relatively low binding affinity for the target ligand, unless a time-consuming maturation process is subsequently used. This library-size limitation has led to the development of techniques for the in vitro generation of peptide libraries including: mRNA display (Roberts, & Szostak (1997) *Proc. Natl. Acad. Sci. USA*, 94, 12297-12302); ribosome display (Mattheakis et al., (1994) *Proc. Natl. Acad. Sci. USA*, 91, 9022-9026); and CIS display (Odegrip et al., (2004) *Proc. Natl. Acad. Sci USA*, 101 2806-2810) amongst others. These libraries can be superior to phage display libraries (and other in vivo-based procedures), in that the size of libraries generated may be 2 to 5 orders of magnitude larger than is possible with phage display.

Where library size is too large or peptide length too long for a particular library screening strategy, zinc finger peptide domains may be screened and selected as part of smaller sub-domains (e.g. of 2 or 3 adjacent zinc finger domains), and then joined together using linkers, such as the linker arrangement described in relation to the framework peptides of the invention. Alternatively, nucleic acid sequences encoding the nucleic acid binding residues (e.g. the recognition sequence) of each zinc finger domain can be synthesised and grafted or cloned into the genetic sequence encoding each zinc finger domain of the framework.

The binding affinity of a selected zinc finger peptide for the selected target sequence can be measured using techniques known to the person of skill in the art, such as surface plasmon resonance, or biolayer interferometry. Biosensor approaches are reviewed by Rich et al. (2009), "A global benchmark study using affinity-based biosensors", *Anal. Biochem.*, 386:194-216. Alternatively, real-time binding assays between a zinc finger peptide and target site may be performed using biolayer interferometry with an Octet Red system (Fortebio, Menlo Park, Calif.).

Zinc finger peptides of the invention have µM or higher binding affinity for a target nucleic acid sequence. Suitably, a zinc finger peptide of the invention has nM or sub-nM binding affinity for its specific target sequence; for example, $10^{-9}$ M, $10^{-10}$ M, $10^{-11}$ M, or $10^{-12}$ M or less. In some particularly preferred embodiments the affinity of a zinc finger peptide of the invention for its target sequence is in the pM range or below, for example, in the range of $10^{-13}$ M, $10^{-14}$ M, or $10^{-15}$ M or less.

In some embodiments of zinc finger peptides for targeting to expanded CAG repeats, the zinc finger peptide has a dissociation constant for sequences of 35 or more CAG repeats that is at least 2-fold higher, at least 5-fold, or at least 10-fold higher than for sequences of less that 22 CAG repeats. Suitably, the affinity of such zinc finger peptides of the invention for DNA sequences having at least 63 CAG repeats is at least 2-fold, at least 5-fold or at least 20-fold higher than for sequences having less that 22 CAG repeats. In some particularly advantageous embodiments, the affinity of such zinc finger peptides for DNA sequences having at least 104 CAG repeats is at least 2-fold, at least 10-fold or at least 50-fold higher than for sequences having less that 22 CAG repeats.

Selection and screening methods used in accordance with the invention can be applied to the selection of zinc finger peptides for binding to any desired target site or nucleic acid sequence; particularly suitable recognition sequences comprise 18 or more, 36 or more, or 54 or more nucleotides, which may be contiguous, or non-contiguous—preferably comprising subsites of 18 contiguous nucleotides. Suitable nucleic acid target sequences are those associated with genetic disorders, particularly with neurological disorders, and still more suitably with disorders associated with duplication, insertion, and expansion of genomic sequences, such as HD.

Therapeutic Compositions

A zinc finger peptide or chimeric modulator of the invention may be incorporated into a pharmaceutical composition for use in treating an animal; preferably a human. A therapeutic peptide of the invention (or derivative thereof) may be used to treat one or more diseases or infections, depending on which binding site the zinc finger peptide was selected or designed to recognise. Alternatively, a nucleic acid encoding the therapeutic peptide may be inserted into an expression construct/vector and incorporated into pharmaceutical formulations/medicaments for the same purpose.

Zinc finger peptides and chimeric modulators of the invention typically contain naturally occurring amino acid residues, but in some cases non-naturally occurring amino acid residues may also be present. Therefore, so-called "peptide mimetics" and "peptide analogues", which may include non-amino acid chemical structures that mimic the structure of a particular amino acid or peptide, may also be used within the context of the invention. Such mimetics or analogues are characterised generally as exhibiting similar physical characteristics such as size, charge or hydrophobicity, and the appropriate spatial orientation that is found in their natural peptide counterparts. A specific example of a peptide mimetic compound is a compound in which the amide bond between one or more of the amino acids is replaced by, for example, a carbon-carbon bond or other non-amide bond, as is well known in the art (see, for example Sawyer, in *Peptide Based Drug Design*, pp. 378-422, ACS, Washington D.C. 1995). Such modifications may be particularly advantageous for increasing the stability of zinc finger peptide therapeutics and/or for improving or modifying solubility, bioavailability and delivery characteristics (e.g. for in vivo applications).

The therapeutic peptides and nucleic acids of the invention may be particularly suitable for the treatment of diseases, conditions and/or infections that can be targeted (and treated) intracellularly, for example, by targeting genetic sequences within an animal cell; and also for in vitro and ex vivo applications. As used herein, the terms "therapeutic agent" and "active agent" encompass both peptides and the nucleic acids that encode a therapeutic zinc finger peptide of the invention. Therapeutic nucleic acids include vectors, viral genomes and modified viruses, such as AAV, which comprise nucleic acid sequences encoding zinc finger peptides and fusion proteins of the invention.

Therapeutic uses and applications for the zinc finger peptides and nucleic acids of the invention include: anti-VEGF agents for treatment of various neoplastic and non-neoplastic diseases and disorders; cancers/neoplastic diseases and related conditions; non-neoplastic conditions, such as neurological disorders, including head injury, spinal cord injury, acute hypertension, meningitis, encephalitis, cerebral malaria, multiple sclerosis, and encephalopathy; diabetic and other proliferative retinopathies; inflammation and inflammatory-related conditions. Other therapeutic uses for the molecules and compositions of the invention include the treatment of microbial infections and associated conditions, for example, bacterial, viral, fungal or parasitic infection. Diseases of trinucleotide repeat expansion are particularly preferred and amenable to the therapies of the present invention, for example: Huntington's disease (poly-CAG), spinocerebellar ataxias (poly-CAG), dentatorubropallidoluysian atrophy (poly-CAG), juvenile myoclonic epilepsy (dodecamer repeats; poly-CCCCGCCCCGCG, SEQ ID NO: 43), Friedreich's ataxia (poly-GAA), fragile-X syndrome (poly-CGG), fragile X-E syndrome (poly-CCG), myotonic dystrophy (poly-CTG).

One or more additional pharmaceutical acceptable carrier (such as diluents, adjuvants, excipients or vehicles) may be combined with the therapeutic peptide of the invention in a pharmaceutical composition. Suitable pharmaceutical carriers are described in "*Remington's Pharmaceutical Sciences*" by E. W. Martin. Pharmaceutical formulations and compositions of the invention are formulated to conform to regulatory standards and can be administered orally, intravenously, topically, or via other standard routes.

In accordance with the invention, the therapeutic peptide or nucleic acid may be manufactured into medicaments or may be formulated into pharmaceutical compositions. When administered to a subject, a therapeutic agent is suitably administered as a component of a composition that comprises a pharmaceutically acceptable vehicle. The molecules, compounds and compositions of the invention may be administered by any convenient route, for example, intradermal, intramuscular, intraperitoneal, intravenous, subcutaneous, intranasal, epidural, oral, sublingual, intranasal, intravaginal, transdermal, rectally, by inhalation, or topically to the skin. Administration can be systemic or local. Delivery systems that are known also include, for example, encapsulation in microgels, liposomes, microparticles, microcapsules, capsules, etc., and can be used to administer the compounds of the invention. Any other suitable delivery systems known in the art are also envisioned in use of the present invention.

Acceptable pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilising, thickening, lubricating and colouring agents may be used. When administered to a subject, the pharmaceutically acceptable vehicles are preferably sterile. Water is a suitable vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or buffering agents.

The medicaments and pharmaceutical compositions of the invention can take the form of liquids, solutions, suspensions, lotions, gels, tablets, pills, pellets, powders, modified-release formulations (such as slow or sustained-release), suppositories, emulsions, aerosols, sprays, capsules (for example, capsules containing liquids or powders), liposomes, microparticles or any other suitable formulations known in the art. Other examples of suitable pharmaceutical vehicles are described in Remington's Pharmaceutical Sciences, Alfonso R. Gennaro ed., Mack Publishing Co. Easton, Pa., 19th ed., 1995, see for example pages 1447-1676.

Suitably, the therapeutic compositions or medicaments of the invention are formulated in accordance with routine procedures as a pharmaceutical composition adapted for oral administration (more suitably for human beings). Compositions for oral delivery may be in the form of tablets, lozenges, aqueous or oily suspensions, granules, powders, emulsions, capsules, syrups, or elixirs, for example. Thus, in one embodiment, the pharmaceutically acceptable vehicle is a capsule, tablet or pill.

Orally administered compositions may contain one or more agents, for example, sweetening agents such as fructose, aspartame or saccharin; flavouring agents such as peppermint, oil of wintergreen, or cherry; colouring agents; and preserving agents, to provide a pharmaceutically palatable preparation. When the composition is in the form of a tablet or pill, the compositions may be coated to delay disintegration and absorption in the gastrointestinal tract, so as to provide a sustained release of active agent over an extended period of time. Selectively permeable membranes surrounding an osmotically active driving compound are also suitable for orally administered compositions. In these dosage forms, fluid from the environment surrounding the capsule is imbibed by the driving compound, which swells to displace the agent or agent composition through an aperture. These dosage forms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade. For oral formulations, the location of release may be the stomach, the small intestine (the duodenum, the jejunem, or the ileum), or the large intestine. One skilled in the art is able to prepare formulations that will not dissolve in the stomach, yet will release the material in the duodenum or elsewhere in the intestine. Suitably, the release will avoid the deleterious effects of the stomach environment, either by protection of the peptide (or derivative) or by release of the peptide (or derivative) beyond the stomach environment, such as in the intestine. To ensure full gastric resistance a coating impermeable to at least pH 5.0 would be essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac, which may be used as mixed films.

To aid dissolution of the therapeutic agent or nucleic acid (or derivative) into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. Potential nonionic detergents that could be included in the formulation as surfactants include: lauromacrogol 400, polyoxyl 40 stearate, polyoxyethylene hydrogenated castor oil 10, 50 and 60, glycerol monostearate, polysorbate 20, 40, 60, 65 and 80, sucrose fatty acid ester, methyl cellulose and carboxymethyl cellulose. These surfactants, when used, could be present in the formulation of the peptide or nucleic acid or derivative either alone or as a mixture in different ratios.

Typically, compositions for intravenous administration comprise sterile isotonic aqueous buffer. Where necessary, the compositions may also include a solubilising agent.

Another suitable route of administration for the therapeutic compositions of the invention is via pulmonary or nasal delivery.

Additives may be included to enhance cellular uptake of the therapeutic peptide (or derivative) or nucleic acid of the invention, such as the fatty acids oleic acid, linoleic acid and linolenic acid.

In one pharmaceutical composition, a zinc finger peptide or nucleic acid of the invention (and optionally any associated non-zinc finger moiety, e.g. a modulator of gene expression and/or targeting moiety) may be mixed with a population of liposomes (i.e. a lipid vesicle or other artificial membrane-encapsulated compartment), to create a therapeutic population of liposomes that contain the therapeutic agent and optionally the modulator or effector moiety. The therapeutic population of liposomes can then be administered to a patient by any suitable means, such as by intravenous injection. Where it is necessary for the therapeutic liposome composition to target specifically a particular cell-type, such as a particular microbial species or an infected or abnormal cell, the liposome composition may additionally be formulated with an appropriate antibody domain or the like (e.g. Fab, $F(ab)_2$, scFv etc.) or alternative targeting moiety, which recognises the target cell-type. Such methods are known to the person of skill in the art.

The therapeutic peptides or nucleic acids of the invention may also be formulated into compositions for topical application to the skin of a subject.

Zinc finger peptides and nucleic acids of the invention may also be useful in non-pharmaceutical applications, such as in diagnostic tests, imaging, as affinity reagents for purification and as delivery vehicles.

Gene Therapy

One aspect of the invention relates to gene therapy treatments utilising zinc finger peptides of the invention for treating diseases.

Gene therapy is the insertion of genes into an individual's cell (e.g. animal or human) and biological tissues to treat disease, for example, by replacing deleterious mutant alleles with functional/corrected versions. The most promising target diseases to date are those that are caused by single-gene defects, such as cystic fibrosis, haemophilia, muscular dystrophy, sickle cell anaemia, and HD. Other common gene therapy targets are aimed at cancer and hereditary diseases linked to a genetic defect, such as expanded nucleotide repeats.

Gene therapy is classified into two type: germ line gene therapy, in which germ cells, (i.e. sperm or eggs), are modified by the introduction of therapeutic genes, which are typically integrated into the genome and have the capacity to be heritable (i.e. passed on to later generations); and somatic gene therapy, in which the therapeutic genes are transferred into somatic cells of a patient, meaning that they may be localised and are not inherited by future generations.

Gene therapy treatments require delivery of the therapeutic gene (or DNA or RNA molecule) into target cells. There are two categories of delivery systems, either viral-based delivery mechanisms or non-viral mechanisms, and both mechanisms are envisaged for use with the present invention.

Viral systems may be based on any suitable virus, such as: retroviruses, which carry RNA (e.g. influenza, SIV, HIV, lentivirus, and Moloney murine leukaemia); adenoviruses, which carry dsDNA; adeno-associated viruses (AAV), which carry ssDNA; herpes simplex virus (HSV), which carries dsDNA; and chimeric viruses (e.g. where the envelop of the virus has been modified using envelop proteins from another virus).

A particularly preferred viral delivery system is AAV. AAV is a small virus of the parvovirus family with a genome of single stranded DNA. A key characteristic of wild-type AAV is that it almost invariably inserts its genetic material at a specific site on human chromosome 19. However, recombinant AAV, which contains a therapeutic gene in place of its normal viral genes, may not integrate into the animal genome, and instead may form circular episomal DNA, which is likely to be the primary cause of long-term gene expression. Advantages of AAV-based gene therapy vectors include: that the virus is non-pathogenic to humans (and is already carried by most people); most people treated with AAV will not build an immune response to remove either the virus or the cells that have been successfully infected with it; it will infect dividing as well as non-dividing (quiescent) cells; and it shows particular promise for gene therapy treatments of muscle, eye, and brain. To date, AAV vectors have been used for first-and second-phase clinical trials for the treatment of cystic fibrosis; and first-phase clinical trials have been carried out for the treatment of haemophilia. There have also been encouraging results from phase I clinical trials for Parkinson's disease, which provides hope for treatments requiring delivery to the central nervous system. Gene therapy trials using AAV have also been reported for treatment of Canavan disease, muscular dystrophy and late infantile neuronal ceroid lipofuscinosis. HSV, which naturally infects nerve cells in humans also may offer advantages for gene therapy of diseases involving the nervous system.

Suitably, in accordance with the invention, zinc finger encoding nucleic acid constructs (as described elsewhere herein) are inserted into an adeno-associated virus (AAV) vector, particularly AAV2/1 subtype (see e.g. *Molecular Therapy* (2004) 10: 302-317). This vector is particularly suitable for injection and infection of the striatum, in the brain, where the deleterious effects of mutant Htt aggregation are most prevalent in HD. In this way, the zinc finger encoding nucleic acid constructs of the invention can be delivered to desired target cells, and the zinc finger peptides expressed in order to repress the expression of mutant htt genes.

Non-viral based approaches for gene therapy can provide advantages over viral methods, for example, in view of the simple large-scale production and low host immunogenicity. Types of non-viral mechanism include: naked DNA (e.g. plasmids); oligonucleotides (e.g. antisense, siRNA, decoy ds oligodeoxynucleotides, and ssDNA oligonucleotides); lipoplexes (complexes of nucleic acids and liposomes); polyplexes (complexes of nucleic acids and polymers); and dendrimers (highly branched, roughly spherical macromolecules).

Accordingly, the zinc finger-encoding nucleic acids of the invention may be used in methods of treating diseases by gene therapy. Particularly suitable diseases are those of the nervous system (peripheral and/or central); and a preferred disease is HD.

In particular, the gene therapy therapeutics and regimes of the invention may provide for the expression of therapeutic zinc fingers in target cells for repressing the expression of target genes, such as those having non-wild-type expanded CAG-repeat sequences, and especially the mutant htt gene. Zinc finger nucleases of the invention (e.g. as fusion proteins with Fok-1 nuclease domain) may also be useful in gene therapy treatments for gene cutting or directing the site of integration of therapeutic genes to specific chromosomal sites, as previously reported by Durai et al. (2005) *Nucleic Acids Res.* 33, 18: 5978-5990.

Huntington's Disease (HD) and Therapies

Unlike other neurological disorders, such as Alzheimer's and Parkinson's diseases, HD is monogenic (The Huntington's Disease Collaborative Research Group (1993) *Cell*, 72(6): 971-983). Therefore, a useful therapeutic strategy against HD may only need to target the expression of the single causal gene in order to reverse and treat the effects of the mutant protein. However, since wt Htt protein is widely expressed (Sharp et al. (1995) *Neuron* 14(5): 1065-1074); is essential for early embryonic development (Duyao et al. (1995) *Science* 269(5222): 407-410); and is required for neuronal function and survival in the brain (Dragatsis et al. (2000) *Nat. Genet.* 26(3): 300-306); it is important to reduce the expression of the mutant protein specifically, and to leave the expression of the wt protein unaffected.

Recently, RNA interference (RNAi) was shown to reduce expression of mutant htt (van Bilsen et al. (2008) *Hum. Gene Ther.* 19(7): 710-719; Zhang et al. (2009) *J. Neurochem.* 108(1): 82-90; Pfister et al. (2009) *Curr. Biol.* 19(9): 774-778). Although this technique may have the potential to be quite powerful, the success of RNAi depends on targeting single nucleotide or deletion polymorphisms that differentiate between mutant and wt alleles, and these often differ from patient to patient. The requirement for personalised siRNA designs currently raises challenges for clinical trials and approved use in humans.

In a more general approach, Hu et al. used peptide nucleic acid (PNA), and locked nucleic acid (LNA) antisense oligomers, to target expanded CAG-repeats of the ataxin-3 and htt genes (Hu et al. (2009) *Nat. Biotechnol.* 27(5): 478-484; Hu et al. (2009) *Ann. NY Acad. Sci.* 1175: 24-31). They observed selective inhibition of the mutant allele with peptide nucleic acids (PNAs) for up to 22 days. Although these results also appear promising, PNAs cannot be delivered to the central nervous system. Therefore, the authors also tried to use locked nucleic acids (LNAs), which are more suitable for in vivo applications. In this experiment inhibition of the mutant allele was observed, but up to 30% inhibition of wt htt was also seen at the most effective concentration of LNA used.

Therefore, there is still a clear need in the art for effective therapies for inhibiting the expression of mutant Htt protein, while leaving the expression of the wild type allele largely unaffected.

Accordingly, in this work, the inventors rationally designed zinc finger peptides to be able to recognise and bind poly-5'-GC(A/T)-3' sequences, such that they would recognise both poly-CAG and its complementary DNA strand, poly-CTG. Beneficial zinc finger peptides of the invention were able to repress a target gene with expanded CAG-repeat sequences preferentially over shorter repeat sequences in transient transfection reporter assays. Using a model cell line for HD, the inventors achieved stable expression of zinc finger peptides, which also reduced expression of the chromosomal mutant htt gene (having 111 CAG-repeats). Repression of gene expression was demonstrated both at the protein and the RNA levels. Repression of the mutant genes that were targeted was shown to persist for extended periods (e.g. over 20 days), and the expression of genes having shorter genomic CAG-repeat sequences were found to remain broadly unaffected. Thus, the zinc finger peptides of the invention target the expanded CAG repeats associated with the mutant Htt gene in preference to the normal CAG repeats associated with the wild type Htt gene. Therefore, zinc finger peptides of the invention are efficient and selective repressors of genes with long CAG-tracts.

Likewise, the zinc finger peptides of the invention are suitable for the targeting and modulation of genes containing long repeat sequences (particularly trinucleotide repeats) associated with genes other than Htt, as previously indicated.

The invention will now be further illustrated by way of the following non-limiting examples.

EXAMPLES

Unless otherwise indicated, commercially available reagents and standard techniques in molecular biological and biochemistry were used.

Materials and Methods

The following procedures used by the Applicant are described in Sambrook, J. et al., 1989 supra.: analysis of restriction enzyme digestion products on agarose gels and preparation of phosphate buffered saline. General purpose reagents, oligonucleotides, chemicals and solvents were purchased from Sigma-Aldrich Quimica SA (Madrid, Spain). Enzymes and polymerases were obtained from New England Biolabs (NEB Inc.; do IZASA, S.A. Barcelona, Spain).

Vector and Zinc Finger Peptide (ZFP) Construction

To build a zinc finger peptide (ZFP) framework that recognises both GCA and GCT DNA sequences (which are found within expanded CAG-repeats), a zinc finger scaffold based on the wild-type backbone sequence of the zinc finger region of wild-type zif268 was selected. Amino acid residues responsible for DNA target recognition (i.e. the "recognition sequence", which essentially corresponds to the α-helical region of the framework) were designed having regard to two previously reported studies: (1) Choo et al. (1994) *Nature* 372(6507): 642-645, engineered ZFPs with the following α-helical recognition sequences (residues −1 to 6), QAATLQR (SEQ ID NO: 44) for binding to the GCA triplet, and QAQTLQR (SEQ ID NO: 45) for binding to the GCT triplet; and (2) Isalan et al. (1998) *Biochemistry* 37(35): 12026-12033, reported that the sequence QRAS-RKR (SEQ ID NO: 46) was able to recognise GN(T/A) triplets. These α-helical amino acid sequences were combined to generate a novel hybrid α-helix sequence, QRATLQR (SEQ ID NO: 1), comprising positions −1, 1 and 2 from Isalan et al. and residues 3, 4, 5 and 6 from Choo et al. The resultant zinc finger domain was expected to bind the sequence GC(T/A), and was termed ZFx Hunt (FIG. 1C). A pUC57 vector containing 6 such zinc finger domains, termed ZF6x Hunt, was synthesised (Genscript Corporation (Piscataway, N.J.). This vector also included a T7 promoter, an N-terminal NLS (PKKKRKV; (SEQ ID NO: 40), and restriction sites for deriving 4 (ZF4), 11 (ZF11), 12 (ZF12) and 18 (ZF18) zinc finger peptides in tandem arrays by subcloning (see Table 1 for zinc finger sequences; SEQ ID NOs: 6 to 15). For example, to clone pUC57 ZF4, the vector pUC57 ZF6 was cut with Eag1 and re-ligated (zinc finger peptide SEQ ID NO: 6). To clone ZF12, pUC ZF6 was digested with SpeI, and a PCR fragment containing ZF6 (with SpeI linkers) was cloned into the SpeI site (zinc finger peptide, SEQ ID NO: 12). A KpnI site was added for future cloning purposes (PCR fragment: "SpeI-KpnI-ZF6-SpeI"). ZF11 was derived from ZF12 by deleting the N-terminal finger by homologous recombination (zinc finger peptide, SEQ ID NO: 10). ZF18 was constructed with a PCR-cloning strategy similar to that for ZF12, resulting in slightly shorter linkers (zinc finger peptide, SEQ ID NO: 14).

The zinc finger peptides were then subcloned into the mammalian expression vector pTarget (Promega). A 3× FLAG tag sequence (DYKDHDG DYKDHDI DYKDDDDK; SEQ ID NO: 47) was introduced by PCR at the N-terminus, and either the FokI endonuclease domain or the Kox-1 (KRAB repression domain) coding sequences were introduced at the C-terminus, with a 3Xggggs (SEQ ID NO: 48) linker between the zinc finger peptide and the effector domain.

The pEH vector series was cloned in two steps. First, the EGFP coding region was excised from pEGFP-N1 (Clontech), using HindIII/XbaI, and cloned into pGL4.13 (Promega) to give pSV40-EGFP. Then, a PCR product containing CMV-HcRed-polyA and ClaI linkers was cloned into pSV40-EGFP (partially digested with ClaI). The EGFP start codon was mutated to alanine by site directed mutagenesis, and PCR fragments containing human Htt exon I from different human genomic templates (to obtain different numbers of CAG repeats), were cloned into the pEH EcoRI site, upstream and in frame with EGFP (pEH-Q series). The pSV40-mCherry vector series were generated by replacing EGFP from the pSV40-EGFP vector series with mCherry using XmaI/XbaI sites.

In Vitro Gel Shift Assays

First, pUC57-ZFx Hunt, M13fwd and M13rev primers (M13fwd, GTAAAACGACGGCCAG (SEQ ID NO: 94); M13rev, CAGGAAACAGCTATGAC (SEQ ID NO: 95); see Table 3), were used to generate PCR products for in vitro expression of the ZFP, using the TNT T7 Quick PCR DNA kit (Promega). Double stranded DNA probes with different numbers of CAG repeats based on the standard sequence: 5'-ACG TAC (CAG)n TCA CAG TCA GTC CAC ACG TC-3' (SEQ ID NO: 49) were produced by Klenow fill-in. 100 ng of double stranded DNA was used in a DIG-labeling reaction using Gel Shift kit, $2^{nd}$ generation (Roche), following the manufacturer's instructions. For gel shift assays, 0.005 pmol of DIG-labelled probe were incubated with increasing amounts of TNT-expressed protein in a 20 µl reaction containing 0.1 mg/ml BSA, 0.1 pg/ml polydI:dC, 5% glycerol, 20 mM Bis-Tris Propane, 100 mM NaCl, 5 mM $MgCl_2$, 50 mg/ml $ZnCl_2$, 0.1% NonidetP40 and 5 mM DTT for 1 hour at 25° C. Binding reactions were separated in a 7% non-denaturing acrylamide gel for 1 hour at 100 V, transferred to a nylon membrane for 30 min at 400 mA, and visualisation was performed following manufacturer's instructions.

Cell Culture and Gene Delivery

The cell line HEK-293T (ATCC) was cultured in 5% $CO_2$ at 37° C. in DMEM (Gibco) supplemented with 10% FBS (Gibco). Qiagen purified DNA was transfected into cells using Lipofectamine 2000 (Invitrogen) according to the manufacturer's instructions. Briefly, cells were plated onto 10 mm wells to a density of 50% and 70 ng of reporter plasmid, 330 ng of ZFP expression plasmid and 2 µl of Lipofectamine 2000 were mixed and added to the cells. Cells were harvested for analysis 48 hours later.

STHdh+/Hdh+ and STHdhQ111/Hdh111 cells (gift from M. E. MacDonald) were cultured in 5% $CO_2$ at 33° C. in DMEM supplemented with 10% FBS (Gibco) and 400 µg/ml G418 (PAA). Cells were infected with retroviral particles using the pRetroX system (Clontech) according to the manufacturer's instructions.

Flow Cytometry Analysis

Cells were harvested 48 hours post-transfection and analysed in a BD FACS Canto Flow cytometer using BD FACSDiva software.

Western Blot 293T cells were harvested 48 hours post-transfection in 100 µl of 2× SDS loading dye with Complete protease inhibitor (Roche). 20 µl of sample was separated in 4-15% Criterion Tris-HCl ready gels (BioRad) for 2 hours at 100V, transferred to Hybond-C membrane (GE Healthcare) for 1 hour at 100V. Proteins were detected with either the primary antibody anti β-actin (Sigma A1978) at 1:3000 dilution or anti-EGFP (Roche) at 1:1500 dilution and with a peroxidase-conjugated donkey anti-mouse secondary antibody (Jackson ImmunoResearch) at 1:10000 dilution. Visualisation was performed with ECL system (GE Healthcare) using a LAS-3000 imaging system (Fujifilm). STHdh cells were trypsinised and harvested in PBS containing Complete protease inhibitor (Roche). Cells were resuspended in RIPA buffer (1% TritonX-100, 1% sodium deoxycholate, 40 mM Tris-HCl, 150 mM NaCl, 0.2% SDS, Complete), incubated in ice for 15 min, and were centrifuged at 13000 rpm for 15 min. The supernatant was collected and protein concentration was determined using BioRad's $D_C$ protein assay. 60 pg of protein was separated in a 5% Criterion Tris-HCl ready gel (BioRad) for 2 hours at 100V, transferred using iBlot Dry Blotting System (Invitrogen) for 8 min and endogenous Htt protein was detected with anti-Huntingtin primary antibody (Millipore MAB2166) at a 1:1000 dilution.

qRT-PCR

RNA was prepared with RNeasy kit (Qiagen) and reversed transcribed with Superscript II (Invitrogen). Real Time PCR was performed in a LightCycler® 480 Instrument (Roche) using LightCycler® 480 SYBR Green I Master (Roche). Primer sets are given in full in Table 3.

Production of Adeno-Associated Viral Vector

AAV2/1-CAG-GFP-WPRE and AAV2/1-CAG-ZF11× Hunt-KoxI-WPRE containing a CAG promoter (CMV early enhancer element and the chicken beta-actin promoter) and WPRE (Woodchuck post-translational regulatory element), were produced at the Centre for Animal Biotechnology and Gene Therapy of the Universitat Autonoma of Barcelona (CBATEG-UAB) as previously described (Salvetti et al. (1998) Hum. Gene Ther. 9: 695-706). Recombinant virus was purified by precipitation with PEG8000 followed by iodixanol gradient ultracentrifugation with a final titre of $7.41 \times 10^{11}$ genome copies/ml.

Animals—R6/2 Transgenic Mice

R6/2 transgenic mice were purchased form Jackson Laboratories (B6CBA -Tg(HDexon1)62Gpb/3J). Ovarian transplanted hemizygous females and wt B6CBAF1/J males were bred in house, and progeny was genotyped as previously described (Benn, et al. (2009), PLoS One 4, e5747).

Stereotaxic injections were performed on 4-week-old mice. Briefly, mice were anesthetised with isofluorane and fixed on a stereotaxic frame. Buprenorphine was injected at 0.05 mg/kg. AAVs were injected bilaterally into the striatum (A/P+0.7 mm, M/L ±1.8 mm, D/V −3.0 mm relative to bregma) using a 10 µl Hamilton syringe at a rate of 0.25 µl/min controlled by an Ultramicropump (World Precision Instruments). For each hemisphere, a total volume of 3 µl ($2.2 \times 10^9$ genomic particles) were injected in two steps: 1.5 µl were injected at −3.0 mm DV, the needle was let to stand for 3 minutes in position, and then the other half was injected at −2.5 mm DV. Females were randomly injected with AAV-CAG-ZF11× Hunt-Kox-1-WPRE in one hemisphere and with control AAV expressing GFP (AAV2/1-GFP) into the other hemisphere. Some females were injected only in one hemisphere with either AAV-CAG-ZF11× Hunt-Kox-1-WPRE or AAV2/1-GFP.

Female mice were sacrificed at different ages for posterior analysis by RT-PCR, immunohistochemistry or western blot. Males were bilaterally injected with 3 µl of the same virus in both hemispheres (AAV-CAG-ZF11× Hunt-Kox-1-WPRE or AAV2/1-GFP) for behavioral assays.

Animal Behavioral Tests

Behavioural monitoring commenced at 3 weeks of age and tests took place bimonthly until 11 weeks of age. All the experiments were performed double-blind with respect to the genotype and treatment of the mice.

Clasping behaviour was checked by suspending the animal by the tail for 20 seconds. Mice clasping their hindlimbs were given a score of 1, and mice that did not clasp were given a score of 0.

Grip strength was measured by allowing the mice to secure to a grip strength meter and pulling gently by the tail. The test was repeated three times and the mean and maximum strength recorded.

For the accelerating rotarod test, mice were trained at 3 weeks of age to stay in the rod at a constant speed of 4 rpm until they reached a criterion of 3 consecutive minutes in the rod. In the testing phase, mice were put in the rotarod at 4 rpm and the speed was constantly increased for 2 minutes until 40 rpm. The assay was repeated twice and the maximum and average latency to fall from the rod was recorded.

For the open field test, mice were put in the centre of a white methacrylate squared open field (70×70 cm) illuminated by a dim light (70 lux) to avoid aversion, and their distance travelled, speed and position was automatically measured with a video tracking software (SMART system, Panlab, Spain). Other activities, such as rearing, leaning, grooming and number of faeces were monitored de visu.

For the paw print test, mice hindpaws were painted with a non-toxic dye and mice were allowed to walk through a small tunnel (10×10×70 cm) with a clean sheet of white paper in the floor. Footsteps were analysed for three step cycles and three parameters measured: (1) stride length—the average distance between one step to the next; (2) hind-base width—the average distance between left and right hind footprints; and (3) splay length—the diagonal distance between contralateral hindpaws as the animal walks.

Example 1

Design of Zinc Finger Peptide (ZFP) Arrays to Bind CAG Repeats

It is known that zinc finger domains can be concatenated to form multi-finger (e.g. 6-finger) chains (Moore et al.

(2001) *Proc. Natl. Acad. Sci. USA* 98(4): 1437-1441; and Kim & Pabo (1998) *Proc. Natl. Acad. Sci. USA* 95(6): 2812-2817), but to date, no systematic exploration of the binding modes of different-length ZFP to long repetitive DNA tracts has been reported.

The inventors, therefore, used rational design to construct a zinc finger domain (ZF× Hunt) that would bind the 5'-GC(A/T)-3' sequence in double stranded DNA. Polyfinger proteins comprising arrays of Zf× Hunt were, therefore, expected to bind to poly-GCA and poly-GCT sequences (see Materials and Methods above and FIG. 1). Both DNA strands of the CAG double stranded repeat were targeted because: (i) it was thought that this would increase the avidity of the zinc finger peptides for low-copy chromosomal targets; and (ii) it enabled Fok-I nuclease fusion designs to be tested (as described below). To try to avoid the zinc finger peptides of the invention losing their register with cognate DNA (after 3 or more adjacent fingers and 9 contiguous base pairs of double helical DNA), the linker sequences were carefully designed. In particular, the length of the linkers between adjacent zinc fingers in the arrays was modulated. In this way, the register between the longer arrays of zinc finger peptides, especially on binding to dsDNA, could be optimised. Using structural considerations, it was decided to periodically modify the standard canonical linker sequences in the arrays. Therefore, canonical-like linker sequences containing an extra Gly (or Ser) residue or flexible (up to 29-residue) linker sequences were included in the long zinc finger array after every 2- and 6-fingers, respectively (see Table 1 and SEQ ID NOs: 6, 8, 10, 12 and 14). In this way, different numbers of zinc fingers could be tested for optimal length-dependent discrimination.

TABLE 1

Zinc finger peptide framework amino acid and encoding nucleic acid sequences. In amino acid sequences recognition sequences are underlined and linker sequences are shown in bold.

ZF4xHunt amino acid sequence (SEQ ID NO: 6):
FQCRICMRNFSQRATLQRHIRTH TGEKP

FACDICGRKFAQRATLQRHTKIH TGSERP

FQCRICMRNFSQRATLQRHIRTH TGEKP

FACDICGRKFAQRATLQRHTKIH

ZF4xHunt nucleic acid sequence
(SEQ ID NO: 7):
TTCCAGTGCCGCATTTGTATGCGCAACTTTAGCCAGCGCGCGAC

CCTGCAGCGTCATATTCGCACCCATACCGGTGAAAAACCGTTTG

CGTGCGATATTTGCGGTCGTAAATTTGCGCAGCGTGCGACCCTG

CAGCGCCATACCAAAATTCACACCGGATCCGAACGGCCGTTTCA

GTGCAGGATTTGCATGCGTAATTTTTCCCAGCGCGCGACCCTGC

AGCGCCATATTCGCACCCATACTGGTGAAAAACCGTTTGCCTGC

GATATTTGCGGTCGTAAATTTGCGCAGCGTGCTACCTTACAGCG

CCATACCAAAATTCAT

ZF6xHunt amino acid sequence (SEQ ID NO: 8):
FQCRICMRNFSQRATLQRHIRTH TGEKP

FACDICGRKFAQRATLQRHTKIH TGSERP

FQCRICMRNFSQRATLQRHIRTH TGEKP

TABLE 1-continued

Zinc finger peptide framework amino acid and encoding nucleic acid sequences. In amino acid sequences recognition sequences are underlined and linker sequences are shown in bold.

FACDICGRKFAQRATLQRHTKIH TGSERP

FQCRICMRNFSQRATLQRHIRTH TGEKP

FACDICGRKFAQRATLQRHTKIH

ZF6xHunt nucleic acid sequence
(SEQ ID NO: 9):
TTCCAGTGCCGCATTTGTATGCGCAACTTTAGCCAGCGCGCGAC

CCTGCAGCGTCATATTCGCACCCATACCGGTGAAAAACCGTTTG

CGTGCGATATTTGCGGTCGTAAATTTGCGCAGCGTGCGACCCTG

CAGCGCCATACCAAAATTCACACCGGATCCGAACGGCCGTTTCA

GTGCCGTATTTGCATGCGTAATTTTAGCCAGCGTGCGACCCTGC

AGCGCCATATTCGTACCCATACCGGTGAAAAACCGTTTGCCTGC

GATATTTGTGGCCGTAAATTTGCCCAGCGCGCGACCCTGCAGCG

CCATACCAAAATTCATACCGGTTCTGAACGGCCGTTTCAGTGCA

GGATTTGCATGCGTAATTTTTCCCAGCGCGCGACCCTGCAGCGC

CATATTCGCACCCATACTGGTGAAAAACCGTTTGCCTGCGATAT

TTGCGGTCGTAAATTTGCGCAGCGTGCTACCTTACAGCGCCATA

CCAAAATTCAT

ZF11xHunt amino acid sequence
(SEQ ID NO: 10):
FQCRICMRNFSQRATLQRHTKIH TGSERP

FQCRICMRNFSQRATLQRHIRTH TGEKP

FACDICGRKFAQRATLQRHTKIH TGSERP

FQCRICMRNFSQRATLQRHIRTH TGEKP

FACDICGRKFAQRATLQRHTKIH **LRQKDGGGGSGGGGSGGGGS
QLVGTAERP**

FQCRICMRNFSQRATLQRHIRTH TGEKP

FACDICGRKFAQRATLQRHTKIH TGSERP

FQCRICMRNFSQRATLQRHIRTH TGEKP

FACDICGRKFAQRATLQRHTKIH TGSERP

FQCRICMRNFSQRATLQRHIRTH TGEKP

FACDICGRKFAQRATLQRHTKIH

ZF11xHunt nucleic acid sequence
(SEQ ID NO: 11):
TTCCAGTGCCGCATTTGTATGCGCAACTTTAGCCAGCGCGCGAC

CCTGCAGCGCCATACCAAAATTCACACCGGATCCGAACGGCCGT

TTCAGTGCCGTATTTGCATGCGTAATTTTAGCCAGCGTGCGACC

CTGCAGCGCCATATTCGTACCCATACCGGTGAAAAACCGTTTGC

CTGCGATATTTGTGGCCGTAAATTTGCCCAGCGCGCGACCCTGC

AGCGCCATACCAAAATTCATACCGGTTCTGAACGGCCGTTTCAG

TGCAGGATTTGCATGCGTAATTTTTCCCAGCGCGCGACCCTGCA

GCGCCATATTCGCACCCATACTGGTGAAAAACCGTTTGCCTGCG

TABLE 1-continued

Zinc finger peptide framework amino acid and encoding nucleic acid sequences. In amino acid sequences recognition sequences are underlined and linker sequences are shown in bold.

ATATTTGCGGTCGTAAATTTGCGCAGCGTGCTACCTTACAGCGC

CATACCAAAATTCATCTGCGCCAGAAAGATGGTGGCGGCGGCTC

AGGTGGCGGCGGTAGTGGTGGCGGCGGCTCACAACTAGTCGGTA

CCGCCGAGCGCCCCTTCCAGTGCCGCATTTGTATGCGCAACTTT

AGCCAGCGCGCGACCCTGCAGCGTCATATTCGCACCCATACCGG

TGAAAAACCGTTTGCGTGCGATATTTGCGGTCGTAAATTTGCGC

AGCGTGCGACCCTGCAGCGCCATACCAAAATTCACACCGGATCC

GAACGGCCGTTTCAGTGCCGTATTTGCATGCGTAATTTTAGCCA

GCGTGCGACCCTGCAGCGCCATATTCGTACCCATACCGGTGAAA

AACCGTTTGCCTGCGATATTTGTGGCCGTAAATTTGCCCAGCGC

GCGACCCTGCAGCGCCATACCAAAATTCATACCGGTTCTGAACG

GCCGTTTCAGTGCAGGATTTGCATGCGTAATTTTTCCCAGCGCG

CGACCCTGCAGCGCCATATTCGCACCCATACTGGTGAAAAACCG

TTTGCCTGCGATATTTGCGGTCGTAAATTTGCGCAGCGTGCTAC

CTTACAGCGCCATACCAAAATTCAT

ZF12xHunt amino acid sequence
(SEQ ID NO: 12):
FQCRICMRNFS<u>QRATLQR</u>HIRTH TGEKP

FACDICGRKFA<u>QRATLQR</u>HTKIH TGSERP

FQCRICMRNFS<u>QRATLQR</u>HIRTH TGEKP

FACDICGRKFA<u>QRATLQR</u>HTKIH TGSERP

FQCRICMRNFS<u>QRATLQR</u>HIRTH TGEKP

FACDICGRKFA<u>QRATLQR</u>HTKIH LRQKDGGGGSGGGGSGGGGS QLVGTAERP

FQCRICMRNFS<u>QRATLQR</u>HIRTH TGEKP

FACDICGRKFA<u>QRATLQR</u>HTKIH TGSERP

FQCRICMRNFS<u>QRATLQR</u>HIRTH TGEKP

FACDICGRKFA<u>QRATLQR</u>HTKIH TGSERP

FQCRICMRNFS<u>QRATLQR</u>HIRTH TGEKP

FACDICGRKFA<u>QRATLQR</u>HTKIH

ZF12xHunt nucleic acid sequence
(SEQ ID NO: 13):
TTCCAGTGCCGCATTTGTATGCGCAACTTTAGCCAGCGCGCGAC

CCTGCAGCGTCATATTCGCACCCATACCGGTGAAAAACCGTTTG

CGTGCGATATTTGCGGTCGTAAATTTGCGCAGCGTGCGACCCTG

CAGCGCCATACCAAAATTCACACCGGATCCGAACGGCCGTTTCA

GTGCCGTATTTGCATGCGTAATTTTAGCCAGCGTGCGACCCTGC

AGCGCCATATTCGTACCCATACCGGTGAAAAACCGTTTGCCTGC

GATATTTGTGGCCGTAAATTTGCCCAGCGCGCGACCCTGCAGCG

CCATACCAAAATTCATACCGGTTCTGAACGGCCGTTTCAGTGCA

TABLE 1-continued

Zinc finger peptide framework amino acid and encoding nucleic acid sequences. In amino acid sequences recognition sequences are underlined and linker sequences are shown in bold.

GGATTTGCATGCGTAATTTTTCCCAGCGCGCGACCCTGCAGCGC

CATATTCGCACCCATACTGGTGAAAAACCGTTTGCCTGCGATAT

TTGCGGTCGTAAATTTGCGCAGCGTGCTACCTTACAGCGCCATA

CCAAAATTCATCTGCGCCAGAAAGATGGTGGCGGCGGCTCAGGT

GGCGGCGGTAGTGGTGGCGGCGGCTCACAACTAGTCGGTACCGC

CGAGCGCCCCTTCCAGTGCCGCATTTGTATGCGCAACTTTAGCC

AGCGCGCGACCCTGCAGCGTCATATTCGCACCCATACCGGTGAA

AAACCGTTTGCGTGCGATATTTGCGGTCGTAAATTTGCGCAGCG

TGCGACCCTGCAGCGCCATACCAAAATTCACACCGGATCCGAAC

GGCCGTTTCAGTGCCGTATTTGCATGCGTAATTTTAGCCAGCGT

GCGACCCTGCAGCGCCATATTCGTACCCATACCGGTGAAAAACC

GTTTGCCTGCGATATTTGTGGCCGTAAATTTGCCCAGCGCGCGA

CCCTGCAGCGCCATACCAAAATTCATACCGGTTCTGAACGGCCG

TTTCAGTGCAGGATTTGCATGCGTAATTTTTCCCAGCGCGCGAC

CCTGCAGCGCCATATTCGCACCCATACTGGTGAAAAACCGTTTG

CCTGCGATATTTGCGGTCGTAAATTTGCGCAGCGTGCTACCTTA

CAGCGCCATACCAAAATTCAT

ZF18xHunt amino acid sequence
(SEQ ID NO: 14):
FQCRICMRNFS<u>QRATLQR</u>HIRTH TGEKP

FACDICGRKFA<u>QRATLQR</u>HTKIH TGSERP

FQCRICMRNFS<u>QRATLQR</u>HIRTH TGEKP

FACDICGRKFA<u>QRATLQR</u>HTKIH TGSERP

FQCRICMRNFS<u>QRATLQR</u>HIRTH TGEKP

FACDICGRKFA<u>QRATLQR</u>HTKIH LRQKDGGGSQLVGTAERP

FQCRICMRNFS<u>QRATLQR</u>HIRTH TGEKP

FACDICGRKFA<u>QRATLQR</u>HTKIH TGSERP

FQCRICMRNFS<u>QRATLQR</u>HIRTH TGEKP

FACDICGRKFA<u>QRATLQR</u>HTKIH TGSERP

FQCRICMRNFS<u>QRATLQR</u>HIRTH TGEKP

FACDICGRKFA<u>QRATLQR</u>HTKIH LRQKDGGGSGTAERP

FQCRICMRNFS<u>QRATLQR</u>HIRTH TGEKP

FACDICGRKFA<u>QRATLQR</u>HTKIH TGSERP

FQCRICMRNFS<u>QRATLQR</u>HIRTH TGEKP

FACDICGRKFA<u>QRATLQR</u>HTKIH TGSERP

FQCRICMRNFS<u>QRATLQR</u>HIRTH TGEKP

FACDICGRKFA<u>QRATLQR</u>HTKIH

TABLE 1-continued

Zinc finger peptide framework amino acid and encoding nucleic acid sequences. In amino acid sequences recognition sequences are underlined and linker sequences are shown in bold.

ZF18xHunt nucleic acid sequence
(SEQ ID NO: 15):
TTCCAGTGCCGCATTTGTATGCGCAACTTTAGCCAGCGCGAC

CCTGCAGCGTCATATTCGCACCCATACCGGTGAAAAACCGTTTG

CGTGCGATATTTGCGGTCGTAAATTTGCGCAGCGTGCGACCCTG

CAGCGCCATACCAAAATTCACACCGGATCCGAACGGCCGTTTCA

GTGCCGTATTTGCATGCGTAATTTTAGCCAGCGTGCGACCCTGC

AGCGCCATATTCGTACCCATACCGGTGAAAAACCGTTTGCCTGC

GATATTTGTGGCCGTAAATTTGCCCAGCGCGCGACCCTGCAGCG

CCATACCAAAATTCATACCGGTTCTGAACGGCCGTTTCAGTGCA

GGATTTGCATGCGTAATTTTTCCCAGCGCGCGACCCTGCAGCGC

CATATTCGCACCCATACTGGTGAAAAACCGTTTGCCTGCGATAT

TTGCGGTCGTAAATTTGCGCAGCGTGCTACCTTACAGCGCCATA

CCAAAATTCATCTGCGCCAGAAAGATGGTGGCGGCTCACAACTA

GTCGGTACCGCCGAGCGCCCCTTCCAGTGCCGCATTTGTATGCG

CAACTTTAGCCAGCGCGCGACCCTGCAGCGTCATATTCGCACCC

ATACCGGTGAAAAACCGTTTGCGTGCGATATTTGCGGTCGTAAA

TTTGCGCAGCGTGCGACCCTGCAGCGCCATACCAAAATTCACAC

CGGATCCGAACGGCCGTTTCAGTGCCGTATTTGCATGCGTAATT

TTAGCCAGCGTGCGACCCTGCAGCGCCATATTCGTACCCATACC

GGTGAAAAACCGTTTGCCTGCGATATTTGTGGCCGTAAATTTGC

CCAGCGCGCGACCCTGCAGCGCCATACCAAAATTCATACCGGTT

CTGAACGGCCGTTTCAGTGCAGGATTTGCATGCGTAATTTTTCC

CAGCGCGCGACCCTGCAGCGCCATATTCGCACCCATACTGGTGA

AAAACCGTTTGCCTGCGATATTTGCGGTCGTAAATTTGCGCAGC

GTGCTACCTTACAGCGCCATACCAAAATTCATCTGCGCCAGAAA

GATGGTGGCGGCt caggt accGCCGAGCGCCCCTTCCAGTGCCG

CATTTGTATGCGCAACTTTAGCCAGCGCGCGACCCTGCAGCGTC

ATATTCGCACCCATACCGGTGAAAAACCGTTTGCGTGCGATATT

TGCGGTCGTAAATTTGCGCAGCGTGCGACCCTGCAGCGCCATAC

CAAAATTCACACCGGATCCGAACGGCCGTTTCAGTGCCGTATTT

GCATGCGTAATTTTAGCCAGCGTGCGACCCTGCAGCGCCATATT

CGTACCCATACCGGTGAAAAACCGTTTGCCTGCGATATTTGTGG

CCGTAAATTTGCCCAGCGCGCGACCCTGCAGCGCCATACCAAAA

TTCATACCGGTTCTGAACGGCCGTTTCAGTGCAGGATTTGCATG

CGTAATTTTTCCCAGCGCGCGACCCTGCAGCGCCATATTCGCAC

CCATACTGGTGAAAAACCGTTTGCCTGCGATATTTGCGGTCGTA

AATTTGCGCAGCGTGCTACCTTACAGCGCCATACCAAAATTCAT

Example 2

Binding of Zinc Finger Peptides to DNA Target Sequences In Vitro

To show that the zinc finger peptides of the invention are capable of binding to CAG repeat sequences, in vitro gel shift assays were carried out as follows.

Zinc finger peptide arrays containing either 4, 6 or 12 ZFx Hunt domains were constructed and tested in gel shift assays, for binding to double-stranded CAG probes (FIG. 1B). These results show that the longer ZFPs gave more complete binding of the probe. Interestingly, distinct bound complexes were observed in the gel shift, indicating that the ZFPs found single thermodynamic equilibria and were not trapped by kinetic intermediates. Highly-repetitive zinc finger and DNA sequences might have been expected to form contiguous partial binding events, which would have been expected to result in broad smears in gel shifts; but this was not the case. Notably, the 12-finger ZFP did give a lower, secondary shift, which is presumably caused by a 6-finger degradation by-product (zinc fingers can be unstable in linker regions; Miller et al. (1985) *EMBO J.* 4(6): 1609-1614). It is believed that the 12-finger and subsequently 18-finger (see below) constructs described herein are the longest functional artificial ZFP chains ever built.

To test whether ZFx Hunt zinc finger domains were able to bind both strands of a CAG-repeat DNA probe, ZF6x Hunt (i.e. the 6-finger peptide) was assayed by gel shift, and was shown to bind equally to both a CAG repetitive probe, $(GCA)_{x6}$ (SEQ ID NO: 98), and to an alternate CAG-CTG probe, $(GCA-GCT)_{x3}$ (SEQ ID NO: 99), as shown in FIG. 1C. Furthermore, when compared to mutated sequences, ZF6x Hunt showed specificity for the $(CAG)_{x7}$ (SEQ ID NO: 100) sequence (see FIG. 1D).

In summary, 4-, 6- and 12-finger ZFPs were synthesised and shown to be able to bind poly 5'-GC(A/T)-3' DNA probes in vitro; and it was shown that the longer ZFPs bound most specifically and efficiently to their target sequences.

Example 3

Repression of polyQ Reporter Genes In Vivo

The intracellular activity of the ZFx Hunt zinc finger domain was tested in vivo using reporter vectors with different numbers of 5' CAG-repeats in frame with EGFP (Q0, Q10, Q35 and Q104; where Q=CAG and the number indicates the number of repeats). To assess whether there were any non-specific effects caused by the zinc finger proteins, an HcRed reporter was cloned in a different region of the same vector, under an independent promoter (FIG. 2A).

HEK293T cells were transiently cotransfected with the indicated reporter and ZFx Hunt vectors, in which zinc finger expression was driven by CMV promoters. Three sets of assays were carried out: quantifying EGFP and HcRed fluorescent cells using Fluorescence-Activated Cell Sorting (FACS); EGFP protein levels in Western blots; and EGFP and HcRed mRNA levels in qRT-PCR (FIGS. 2B to 2D). Whereas shorter CAG-repeats (Q0, Q10) were essentially unaffected by any of ZF4, ZF6, ZF11 or ZF18x Hunt peptides, the longer CAG-repeat targets (Q35, Q104) were strongly repressed in all three assays, e.g. up to 10-fold EGFP repression by FACS, which equates to a 90% reduction (FIG. 2B).

Figure 2:
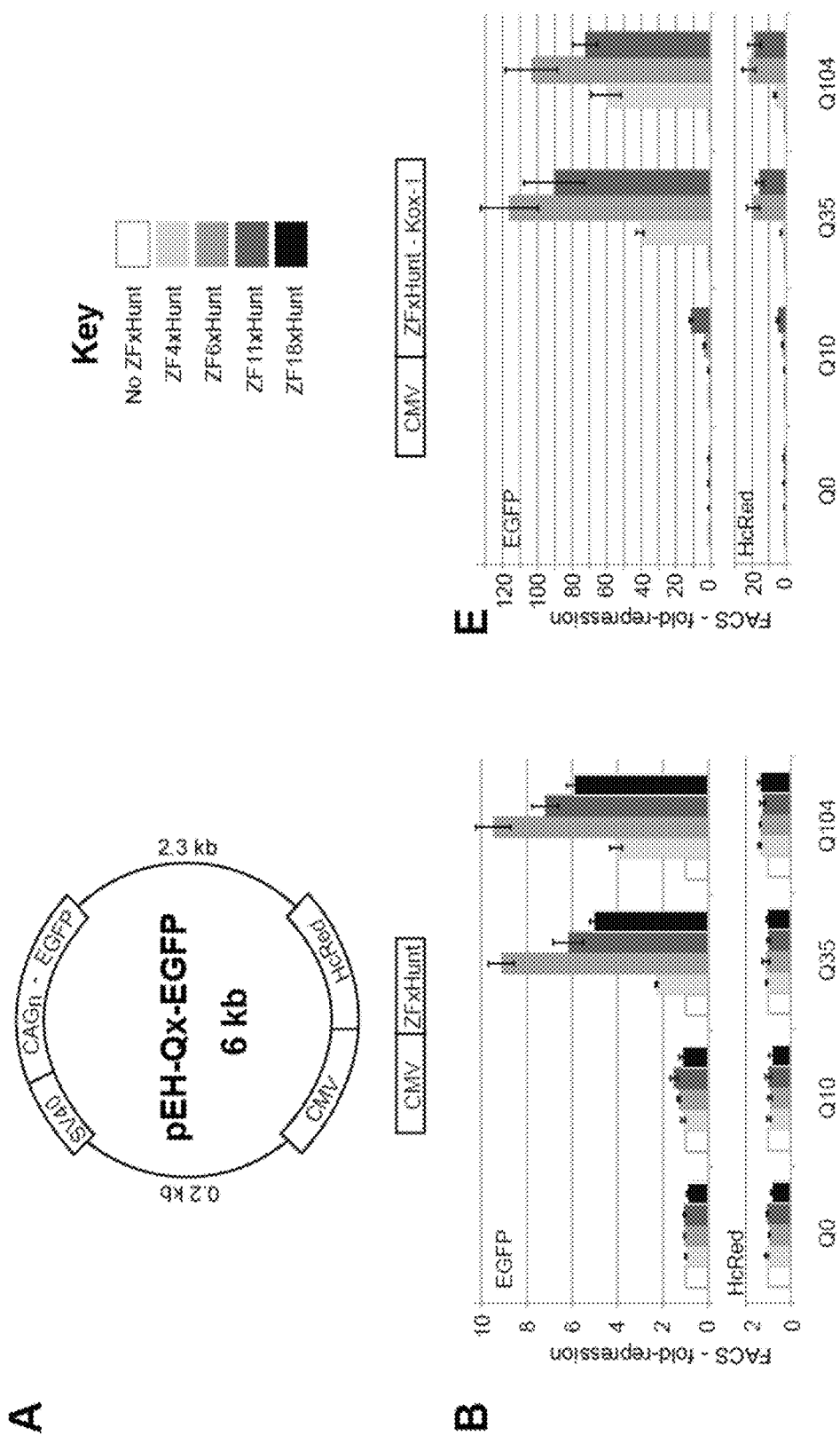
FIG. 2 Episomal poly-CAG-reporter repression by zinc finger peptides of the invention. Results are illustrated for ZFPs without effector domains (panels B to D), or fused to the Kox-1 repressor domain (panels E to G). (A) The pEH reporter plasmid contains EGFP, fused to different-length poly-Q coding sequences, under an SV40 promoter. A control HcRed gene, under a CMV promoter, measures off-target or long-range repression; key: ZFP expression constructs containing 0, 4, 6, 11 or 18 fingers. (B) FACS assay measuring the fold-reduction in EGFP and HcRED fluorescent cells, in response to exposure to different zinc fingers. A 10-fold repression is equivalent to a 90% reduction in protein fluorescence. (C) Illustrates an EGFP Western blot for ZFP repression of pEH-Qx targets. (D) Shows the results of a qRT-PCR assay to measure fold-repression of EGFP or HcRED mRNA by ZFP. (E to G) The same three assays (FACS, Western, qRT-PCR) repeated for ZFPs fused to Kox-1. In panels E to G the vertical scales are larger, which reflects the stronger repression caused by the Kox-1 domain (>100-fold repression; >99% reduction in protein fluorescence), and long-range repression of the HcRed gene by Kox-1.
Figure 2:
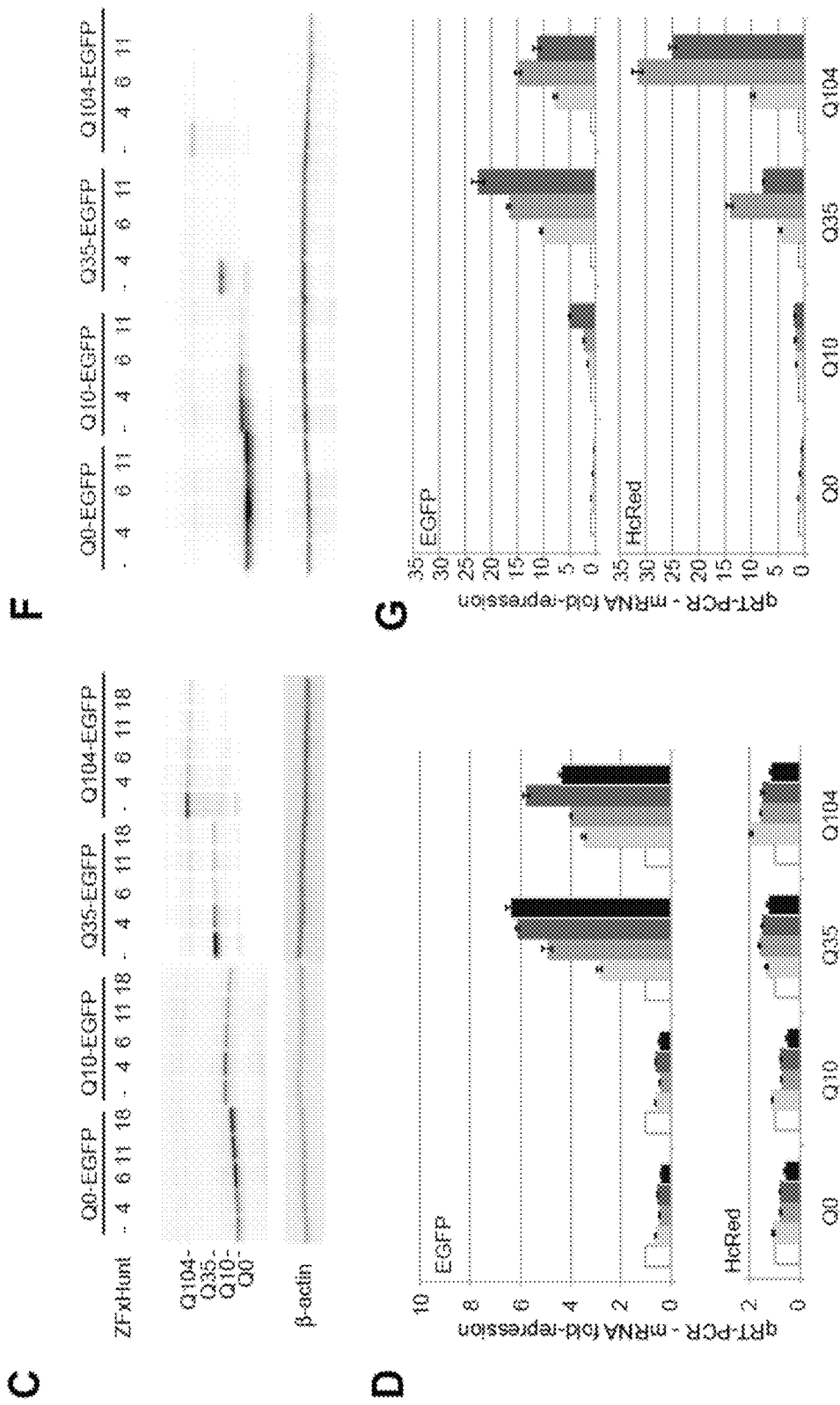

It was also found that longer zinc finger chains gave greater repression of target gene expression as determined in qRT-PCR (FIG. 2D). The 6-finger protein, ZF6× Hunt, was found to be optimal in FACS (FIG. 2B) and Western blots (FIG. 2C).

To test the potential for even stronger repression, the KRAB repression domain Kox-1 (Groner et al. *PLoS Genet* 6(3): e1000869) was fused to the C-terminus of ZF× Hunt proteins (FIGS. 2E to 2G; Table 2). As expected, Kox-1 repression was indeed much stronger. For example, there was up to 98% reduction of green cells by FACS for Q35- and Q104-EGFP, with undetectable levels of EGFP protein by western blot analysis (FIG. 2F). Although repression was generally stronger, it was still proportional to ZFP and CAG-length: for example, the EGFP construct lacking CAG repeats was not repressed, and the constructs having longer CAG-repeats (e.g. Q35) were repressed more strongly than shorter repeat constructs (e.g. Q10-EGFP). In this assay, the ZF11× Hunt-Kox-1 protein was found to provide the strongest level of repression, as shown in FIGS. 2E and G. This demonstrates that, with suitable linker designs, long chains containing odd-numbers of zinc fingers can also function. Moreover, the mechanism of Kox-1-mediated HcRed repression is demonstrated to be dependent on the presence of long CAG-repeats in the plasmid. The unintended level of repression of the neighbouring gene (HcRed) with Kox-1 proteins may be due to the long-range effects of Kox-1 on chromatin structure.

A similar assay was carried out to test the ability of the ZF4, ZF6 and ZF12× Hunt peptides to inhibit episomal reporter expression when fused to the Fok1 nuclease domain, and the results are shown in FIGS. 3A to 3C. The results of these experiments were similar to those reported for "naked" zinc finger peptides (i.e. lacking the Kox-1 domain), although the reduction in cell fluorescence as measured by FACS was less significant for the Fok1 fusion proteins. The results suggest that the Fok1 nuclease domain may act by steric hindrance in these assays because no DNA cleavage was observed and the level of repression was similar to naked zinc fingers (without any repression domain, which can only function by steric mechanisms.

Figure 4:
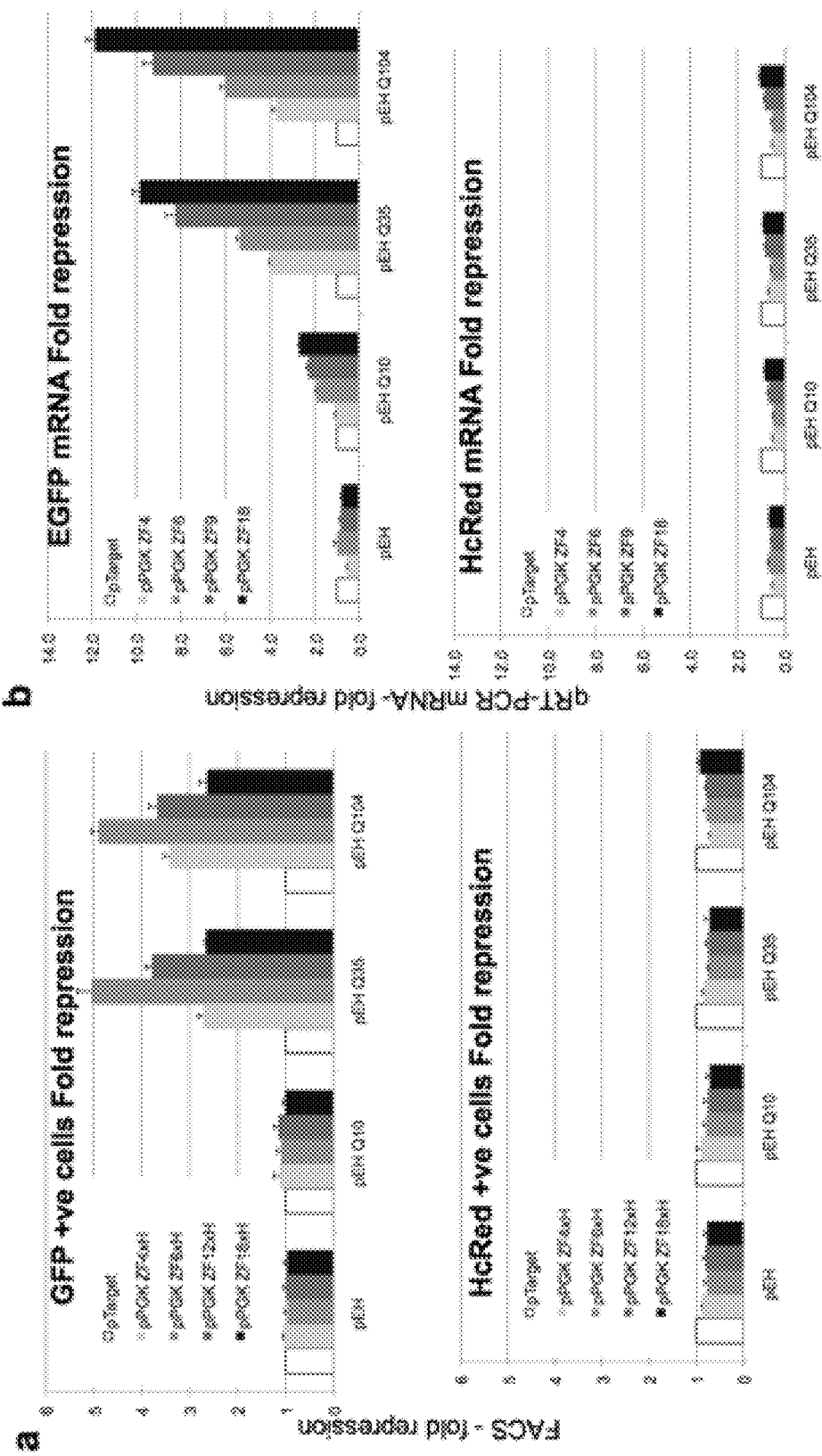
FIG. 4 Episomal reporter repression by ZFPs of the invention. Cells were cotransfected with reporter and zinc finger plasmids: the pEH reporter plasmid contains EGFP, fused to different-length poly-Q coding sequences, under an SV40 promoter. A control HcRed gene, under a CMV promoter, measures off-target or long-range repression. pPGK-ZF (PGK-promoter) expression constructs contain chains of ZF× Hunt (0, 4, 6, 12 or 18 fingers, as indicated). ZFPs are not fused to any effector domains. The pTarget vector does not contain a ZFP and is used as a control. (A) FACS assay measuring the fold-reduction in EGFP or HcRED fluorescent cells, in response to different zinc fingers. A 5-fold repression is equivalent to 80% reduction. (B) gRTPCR assay to measure fold-repression of EGFP or HcRED mRNA by ZFP. (C) EGFP Western blot for ZFP repression of pEH-Qx targets. β-actin staining is used as a loading control.
Figure 4:
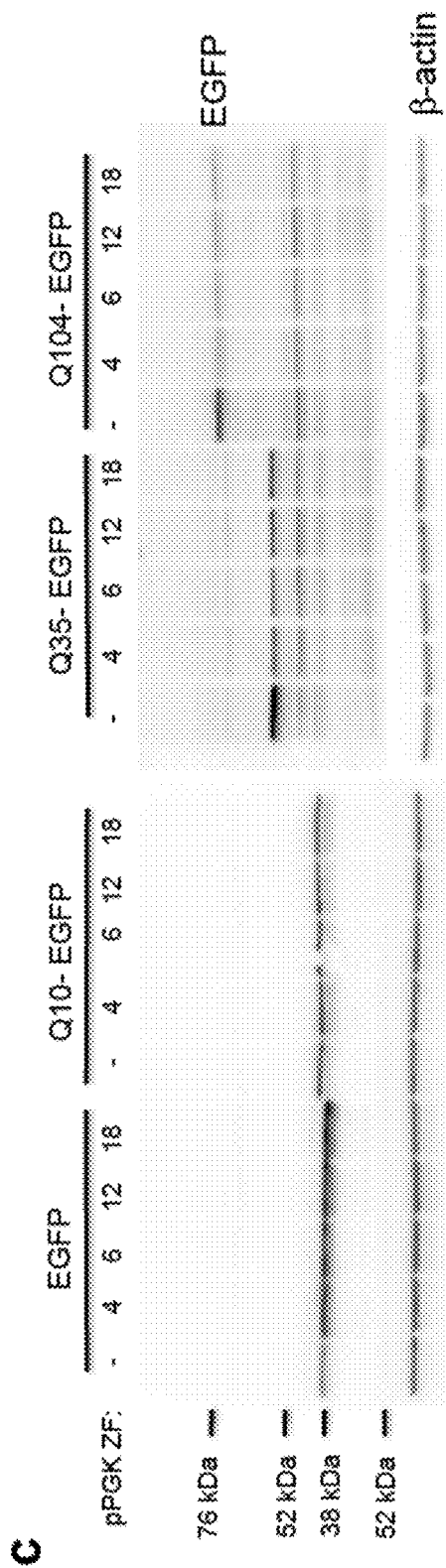

In order to check that these results were not purely specific to ZFPs under the control of the CMV promoter, equivalent tests were also carried out with the ZFPs being expressed under the control of the phosphoglycerate kinase (PGK) promoter. As illustrated in FIG. 4, essentially the same results were obtained for the naked zinc finger peptide constructs.

Importantly, no non-specific repression of HcRed was observed with naked ZFP, suggesting that specific binding of the ZF× Hunt proteins to long CAG repeats is required for repression.

In summary, in transient transfection assays, naked ZF× Hunt proteins specifically repressed the expression of a reporter gene containing 35 or more CAG repeats. ZF× Hunt proteins fused to the Kox-1 domain had a stronger repressive effect, and reduced expression of all CAG-containing reporter genes, with the longer constructs also having a slight affect on a neighbouring control reporter gene.

TABLE 2

Kox-1 domain peptide and encoding nucleic acid sequences, and zinc finger-effector domain linker peptide and encoding nucleic acid sequences.

Kox-1 domain amino acid sequence (SEQ ID NO: 16):
SSLSPQHSAVTQGSIIKNKEGMDAKSLTAWSRTLVTFKDVFVDFTREEWKL

LDTAQQIVYRNVMLENYKNLVSLGYQLTKPDVILRLEKGEEPWLVEREIHQ

ETHPDSETAFEIKSSV

Kox-1 domain nucleic acid sequence (SEQ ID NO: 17):
TCTAGTTTGTCTCCTCAGCACTCTGCTGTCACTCAAGGAAGTATCATCAAG

AACAAGGAGGGCATGGATGCTAAGTCACTAACTGCCTGGTCCCGGACACTG

GTGACCTTCAAGGATGTATTTGTGGACTTCACCAGGGAGGAGTGGAAGCTG

CTGGACACTGCTCAGCAGATCGTGTACAGAAATGTGATGCTGGAGAACTAT

AAGAACCTGGTTTCCTTGGGTTATCAGCTTACTAAGCCAGATGTGATCCTC

CGGTTGGAGAAGGGAGAAGAGCCCTGGCTGGTGGAGAGAGAAATTCACCAA

GAGACCCATCCTGATTCAGAGACTGCATTTGAAATCAAATCATCAGTT

Zinc finger-effector domain peptide sequence
(SEQ ID NO: 18):
LRQKDGGGGSGGGGSGGGGSQLV Zinc finger-effector domain nucleic acid sequence
(SEQ ID NO: 19):
CTGCGCCAGAAAGATGGTGGCGGCGGCTCAGGTGGCGGCGGTAGTGGTGGC

GGCGGCTCACAACTAGTC

Example 4

Competition Binding Assays for Repression of Long CAG-Repeats

For human therapeutic use, ZFPs should preferentially repress long mutant CAG-alleles and have less effect on short wt alleles (e.g. 10- to 29-repeats; the length of wt htt varies in the human population, but is usually in this range; median=18). Therefore, we developed a competition assay to measure length-preference directly. HEK293T cells were cotransfected with three plasmids: the indicated polyQ-EGFP and polyQ-mCherry reporter vectors, together with various ZF× Hunt vectors.

Figure 5:
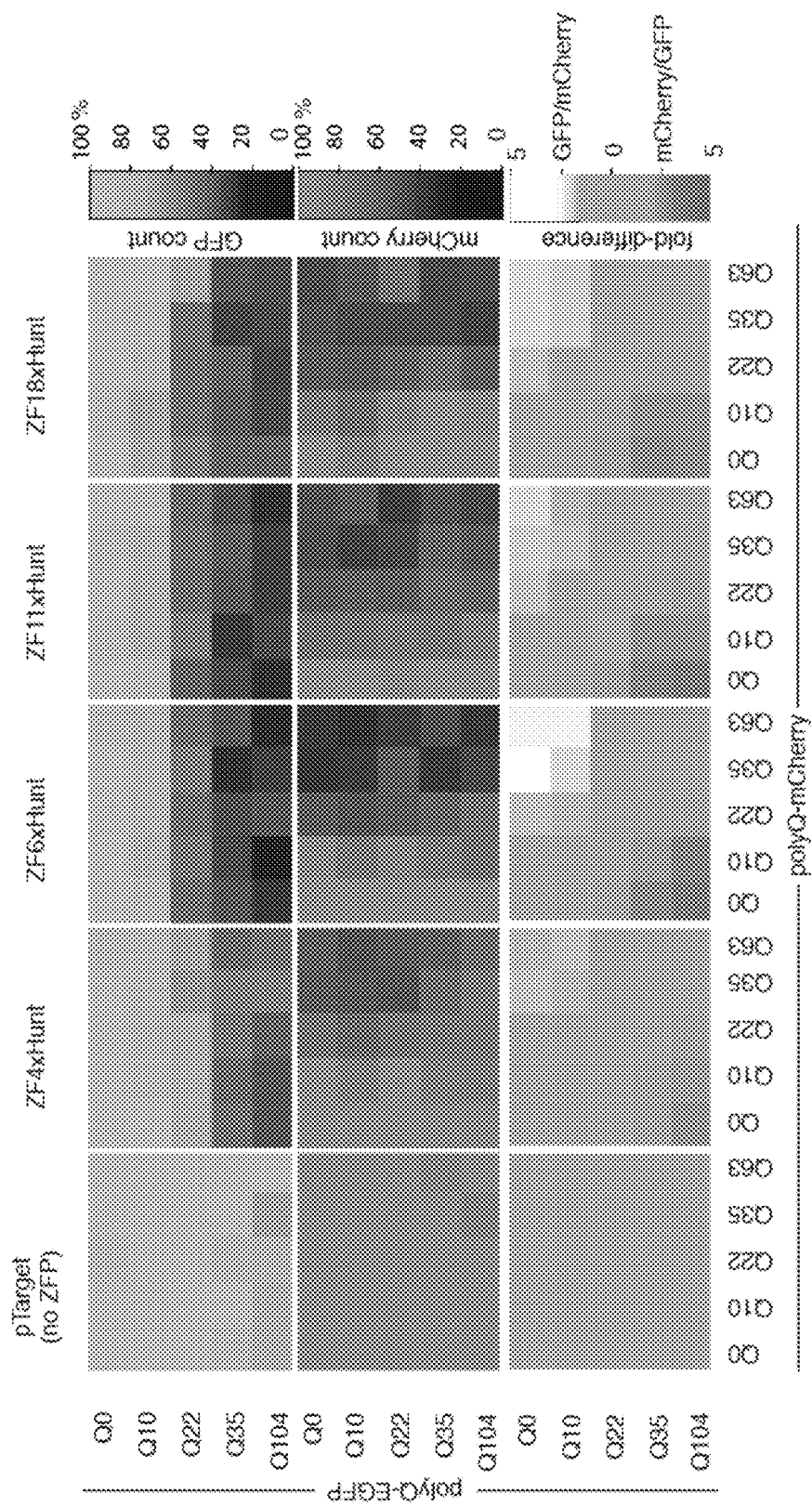
FIG. 5 ZFP competition assay against pairs of different-length CAG-repeat sequences. Each small square represents one transfection experiment, where cells simultaneously receive two reporter plasmids: poly-Q-EGFP and poly-Q-mCherry of different length CAG-repeats (Q0=no repeats; Q10=10 repeats; Q22=22 repeats; Q35=35 repeats; Q63=63 repeats; and Q104=104 repeats). Zinc finger peptides of the invention with 4-, 6-, 11- or 18-fingers were tested for their ability to reduce the number of detectable green and red cells in FACS assays (%). Top row: light grey boxes represent high levels of GFP protein expression, dark grey boxes represent low levels of GFP protein expression; middle row: light grey boxes represent high levels of mCherry protein expression, dark grey boxes represent low levels of mCherry protein expression; bottom row: light (grey) boxes represent higher levels of GFP protein expression compared to mCherry, dark grey boxes represent higher levels of mCherry protein expression compared to GFP. Similar results were obtained using ZFPs fused to the FokI nuclease domain (not shown).

The relative expression of the two reporters was measured by FACS (EGFP or mCherry positive cells), and the results are displayed in FIG. 5. In the top row, light grey boxes represent high levels of GFP protein expression, while dark grey boxes represent low levels of GFP protein expression; in the middle row, light grey boxes represent high levels of mCherry protein expression, while dark grey boxes represent low levels of mCherry protein expression; and in the bottom row, light (grey) boxes represent higher levels of GFP protein expression compared to mCherry, dark grey boxes represent higher levels of mCherry protein expression compared to GFP. The results demonstrate that longer CAG-repeats are preferentially targeted and repressed by all ZF× Hunt peptides, so that cells are dominated by the expression of the shorter green or red constructs when the number of CAG-repeat sequences of their opposite counterpart is longer. This is seen directly by looking at the ratio of green-to-red expression in the bottom row, in which the top right hand corner of each grid is a lighter shade, indicating higher expression levels of GFP; and the bottom left corner of each grid is a darker shade, indicating higher expression levels of mCherry. All constructs, up to 18-finger chains demonstrate active repressing of the longer CAG-repeat reporters.

The experiment was repeated using the same zinc finger peptides fused to the Fok1 effector (nuclease) domain, and the same general results were observed (data not shown). This result once again confirms that the zinc finger proteins are able to bind to both strands of the CAG-repeat sequence and that the zinc finger proteins of the invention are able to preferentially target expanded CAG-repeats.

It is possible that the selective inhibition of longer target sequences is at least partly due to a mass action effect (i.e. longer CAG-repeats contain more potential binding sites for the zinc finger peptides). However, it is also possible that in the case of longer arrays of zinc fingers and shorter CAG-repeat sequences, the peptides may compete with each other for the binding site, and as a consequence, the longer arrays of zinc fingers may bind more transiently or more weakly (e.g. to partial or sub-optimal recognition sequences).

Example 5

Chromosomal Repression of Mutant Htt

Figure 6:
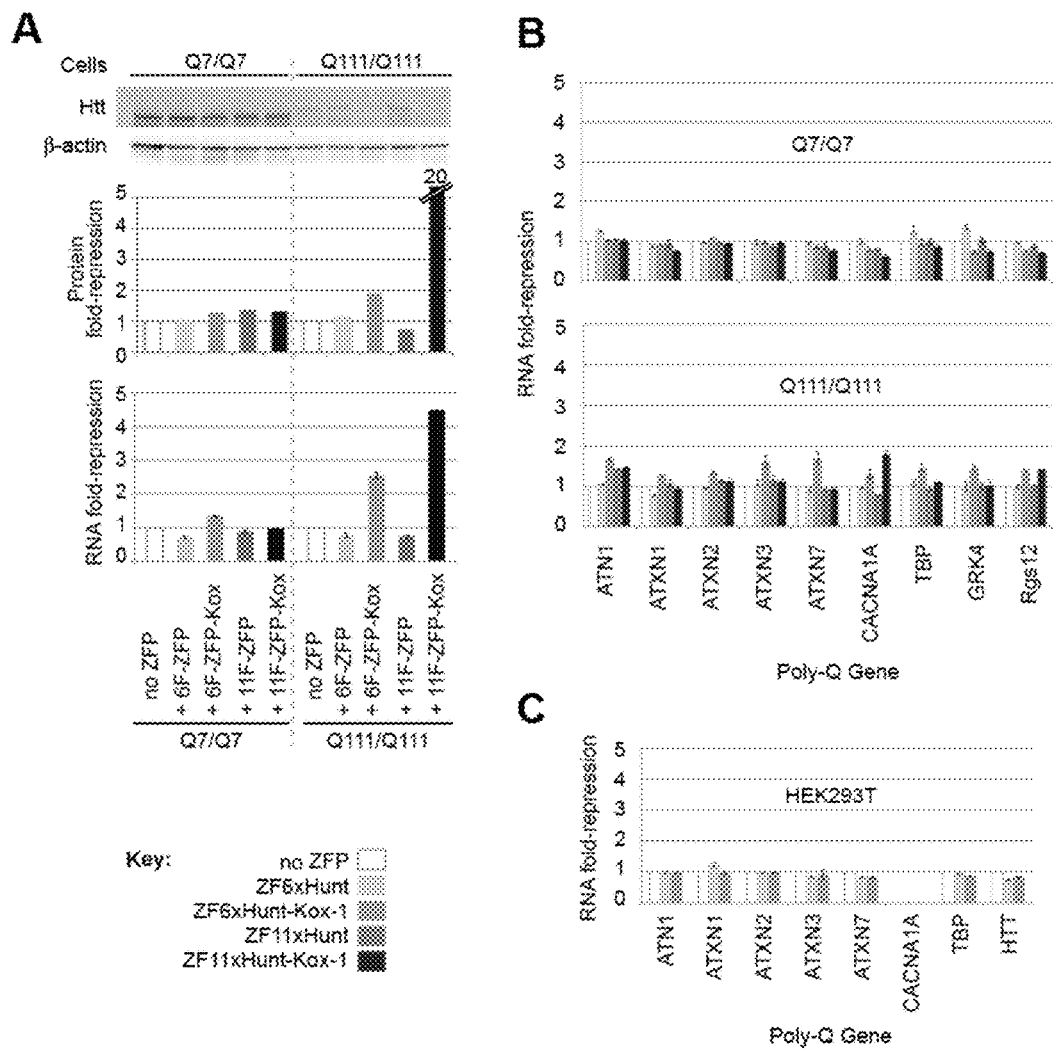
FIG. 6 Expression of chromosomal CAG-repeat genes, 20 days after retroviral ZFP delivery. Assays were carried out in wild-type (wt) mouse STHdh cells with 7 CAG-repeats associated with each copy of the Hdh gene (Q7/Q7); in poly-Q STHdh mutant mice with 111 CAG-repeats associated with each copy of the Hdh gene (Q111/Q111); and in human HEK293T, as indicated. (A) Illustrating the repression of endogenous htt by 6- and 11-finger peptides of the invention (ZF6× Hunt and ZF11× Hunt, respectively), with or without the Kox-1 repressor domain. Western blots for Htt (top row) were controlled with β-actin staining and quantified using ImageJ (Protein fold-repression; middle row). qRT-PCR was used to compare htt mRNA levels (RNA fold repression; bottom row). (B) Shows that the mRNA levels of other wt CAG-repeat genes are broadly unaffected. The expression levels of seven wt genes associated with CAG-repeats were tested by qRT-PCR (atrophin1: ATN1; ataxin-1, -2, -3 and -7: ATXN1, ATXN2, ATXN3 and ATXN7; calcium channel alpha 1A subunit: CACNA1A; and TATA binding protein: TBP). CAG-repeat numbers are illustrated in Table 3. Two genomic neighbours of htt (G protein-coupled receptor kinase 4: GRK4; and G-protein signaling 12: Rgs12) were also unaffected in STHdh cells. (C) The mRNA levels of the seven wt CAG genes and wt HTT (huntingtin; 21 CAG-repeats) were also broadly unaffected in HEK293T cells (N.B. CACNA1A is not expressed in HEK293T cells).

We next tested the effects of the zinc finger repressor peptides, ZF6x Hunt and ZF11x Hunt, on chromosomal htt genes. STHdh cells (Trettel et al. (2000) *Hum. Mol. Genet.* 9(19): 2799-2809) are an established neuronal progenitor cell line from E14 striatal primordia, derived from wt mice (STHdh$^{Q7}$/Hdh$^{Q7}$), or knock-ins, where the first exon of the mouse htt gene with 7 CAG-repeats has been replaced by a human exon with 111 CAG repeats (STHdh$^{Q111}$/Hdh$^{Q111}$). STHdh cells stably expressing naked or Kox-1-fused ZF6x Hunt and ZF11x Hunt peptides were harvested 20 days after retroviral infection, and htt levels were analysed by western blot and qRT-PCR. The experiment was repeated independently twice, and similar results were obtained both times. The results of one experiment are displayed in FIG. 6.

As illustrated in FIG. 6A, neither protein nor RNA levels of wt htt (Q7) were reduced by naked or Kox-1 fused ZF6x Hunt and ZF11x Hunt. By contrast, Q111-mutant htt RNA and protein levels were repressed with ZF6x Hunt-Kox-1 by up to 2.5-fold (60% reduction) and 2-fold (50% reduction), respectively. ZF11x Hunt-Kox-1 showed even stronger repression, with almost 80% reduction in mRNA expression and 95% reduction in the protein levels. Naked ZF6x Hunt and ZF11x Hunt had less effect repressing the chromosomal mutant htt gene, suggesting that the stronger Kox-1 repression effect may be beneficial for chromosomal repression of htt.

Example 6

Specificity of Repression in Wild-Type Genomes

Normal genomes contain several endogenous genes that are known to have CAG-repeat sequences. Therefore, the potential side-effects of stably expressed ZFx Hunt proteins in cells were assayed by qRT-PCR for the wt genes atrophin1, ataxin-1, ataxin-2, ataxin-3, ataxin-7, calcium channel alpha 1A subunit, and TATA binding protein, which all contain CAG-repeat sequences. The number of CAG-repeat sequences in each wild-type gene is shown in Table 3 below.

The results of these assays are displayed in FIGS. 6B and 6C. As illustrated, no adverse effects were measured in either STHdh mouse cells (FIG. 6B), or in HEK293T human cells (FIG. 6C). In the latter, even human htt, which has the most wt CAG repeats in this particular cell line (21-repeats), was also not repressed.

Since Kox-1 repression spreads by establishing heterochromatin (Groner et al. *PLoS Genet* 6(3): e1000869), we also tested the effects of ZF6x Hunt-Kox-1 and ZF11x Hunt-Kox-1 on genes neighbouring htt, in stably-transduced STHdh cells, by qRT-PCR (FIG. 6B). The two adjacent genes, G protein-coupled receptor kinase 4, which is approximately 7 kb upstream; and G-protein signaling 12, which is approximately 188 kb downstream, were assayed and found to be unaffected by the presence of the zinc finger repressor proteins. This suggests that both of these neighbouring genes are out of the range of Kox-1 effects.

The results indicate that both ZF6x Hunt-Kox-1 and ZF11x Hunt-Kox-1 repression is specific for mutant htt in chromosomal loci.

TABLE 3

CAG-repeat number per gene and corresponding primer sets for qRT-PCR. Name prefixes: h = human; m = mouse. Approximate CAG repeat number for wild-type genes was obtained from Genbank mRNA data.

| Gene | CAG repeat length | Forward primer (SEQ ID NO:) | Reverse primer (SEQ ID NO:) |
|---|---|---|---|
| EGFP | 0-104 | CCTGAAGTTCATC TGCACCA (50) | AAGTCGTGCTGCT TCATGTG (51) |
| HcRed | 0 | AGATGCTGCGGAA GAAGAAG (52) | GGTACCGTCGACT GCAGAA (53) |
| hHPRT | N/A | CTTTGCTTTCCTT GGTCAGG (54) | TATCCAACACTTC GTGGGGT (55) |
| hATN1 | 15 | GTCTCCCTCCGAT CTGGATA (56) | CACACTTCCAGGG CTGTAGA (57) |
| hATXN1 | 12 | CCAGCACCGTAGA GAGGATT (58) | AGCCCTGTCCAAA CACAAA (59) |
| hATXN2 | 13 | GACGCAGCTGAGC AAGTTAG (60) | GAAGGAACGTGGG TTGAACT (61) |
| hATXN3 | 7 | AGAGCTTCGGAAG AGACGAG (62) | ACTCCCAAGTGCT CCTGAAC (63) |
| hATXN7 | 10 | AACTGTGTGGCTC ACTCTGG (64) | TGGGAAGATGTTA CCGTTGA (65) |
| hCACNA1A | 13 | GGGAACTACACCC TCCTGAA (66) | CGCTGCTTCTTCT TCCTCTT (67) |
| hTBP | 19 | ACGCCGAATATAA TCCCAAG (68) | CTTCACTCTTGGC TCCTGTG (69) |
| hHtt | 21 | CAGATGTCAGAAT GGTGGCT (70) | GCCTTGGAAGATT AGAATCCA (71) |
| mATN1 | 3 | CACCTGCCTCCAC CTCATGGC (72) | ATGCTCCTTGGGG GCCCTGG (73) |
| mATXN1 | 2 | TGTGGAGAGAATC GAGGAGA (74) | CAGCCCTGTCCAA ATACAAA (75) |
| mATXN2 | 6 | ATCCCAATGCAAA GGAGTTC (76) | CTGCTGATGACCC ACCATAG (77) |
| mATXN3 | 5 | ACCTCGCACTATT CTTGGCT (78) | TGCATCTGTTGGA CCTTGAT (79) |
| mATXN7 | 5 | TGCCCGTGTTCCT CACCGGA (80) | GCGCGGAGACAGT GGTTGCT (81) |
| mCACNA1A | 2 | CACTGGCAATAGC AAAGGAA (82) | TTCTTGAGCGAGT TCACCAC (83) |

TABLE 3-continued

CAG-repeat number per gene and corresponding primer sets for qRT-PCR. Name prefixes: h = human; m = mouse. Approximate CAG repeat number for wild-type genes was obtained from Genbank mRNA data.

| Gene | CAG repeat length | Forward primer (SEQ ID NO:) | Reverse primer (SEQ ID NO:) |
|---|---|---|---|
| mTBP | 3 | ACTTCGTGCAAGA AATGCTG (84) | GCTCATAGCTCTT GGCTCCT (85) |
| mGRK4 | N/A | TCCTGGCTTTGAG GAGCCGA (86) | CCACAGCACAGCT CTGCAGCAT (87) |
| mRgs12 | N/A | GGGGGCTCAAGCA GGCATGG (88) | GGGAGCCAGCCTC CGAGTCA (89) |
| mHtt | 7 or 111 | CAGATGTCAGAAT GGTGGCT (90) | GCCTTGGAAGATT AGAATCCA (91) |
| mHPRT | N/A | GGTTAAGCAGTAC AGCCCCA (92) | AGAGGTCCTTTTC ACCAGCA (93) |
| M13 | N/A | GTAAAACGACGGC CAG (94) | CAGGAAACAGCTA TGAC (95) |

Example 7

Cell Toxicity Assay

Since it would be advantageous for a ZFP-repressor therapy to have low toxicity, we carried out a dye-labelling cell viability assay to test the (non-specific) toxicity of the ZFPs.

Figure 7:
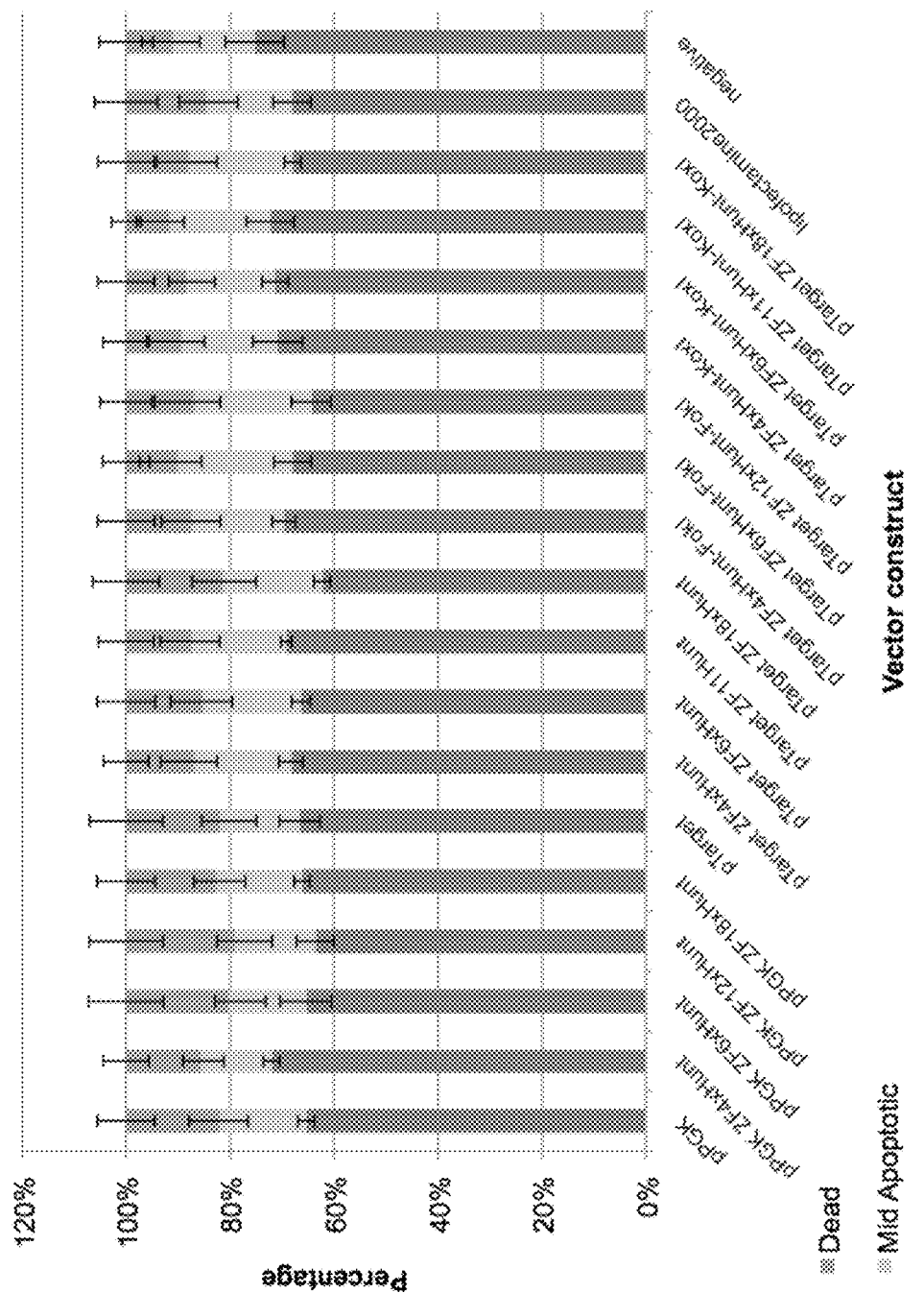
FIG. 7 ZFP toxicity assay. HEK-293T cells were transfected with the indicated vector constructs. As a control Lipofectamine2000-only or untransfected cells (negative) were used. Cytotoxicity was analysed using Guava Cell Toxicity (PCA) Assay and the bars show the percentage of dead mid-apoptotic and viable cells. The results are an average of at least 3 independent experiments.

HEK-293T cells were transfected with 400 ng of the indicated vector constructs using Lipofectamine2000 and harvested 48 hours after transfection. As a control Lipofectamine2000-only or untransfected cells (negative) were used. Cytotoxicity was analysed using the Guava Cell Toxicity (PCA) Assay according to the manufacturer's instructions. The results are presented as the percentage of dead, mid-apoptotic and viable cells (see FIG. 7), in which the bars express results of at least 3 independent experiments.

These data show that no statistically significant toxicity effects were produced in cells expressing zinc finger peptides of the invention, as compared to control experiments. Moreover, ZF6× Hunt-Kox-1 and ZF11× Hunt-Kox-1 were tolerated for over 20 days following stable retroviral transfection, without any apparent adverse cellular effects. Overall, the repressor properties of the zinc finger peptides of the invention and their potential for stable expression, particularly of ZF6× Hunt-Kox-1 and ZF11× Hunt-Kox-1 proteins, suggest that the peptides of the invention have significant potential for gene therapeutic applications.

Example 8

Repression of Mutant Htt Gene in a Mouse Model for Huntington's Disease

As described above, the inventors have designed long zinc finger protein chains (ZFP) to preferentially repress target genes with approximately 35 or more CAG-repeats. It has also been shown that stable expression of the zinc finger proteins of the invention in a model HD cell line reduced chromosomal expression of the mutant htt gene (with 111 CAG-repeats), at both the protein and mRNA level. Meanwhile, the shorter wild-type htt gene (with 7 CAG-repeats in this particular mouse cell line) was unaffected, as were other wild-type genomic CAG repeat genes.

R6/2 mice are a well-established animal model for the study of HD and potential therapeutics. These mice express exon 1 of the human HD gene with approximately 150 CAG repeats. R6/2 mice have an early onset of HD symptoms and a fast progression of the disease, showing a life expectancy of 12 to 17 weeks (Gil & Rego (2009) *Brain Res. Rev.* 59: 410-431).

In this study, the zinc finger proteins of the invention are assayed for their ability to reduce expression of mutant htt in a transgenic mouse model of HD, accordingly to the timeline shown below.

First, the ZF6× Hunt-Kox-1, ZF11× Hunt-Kox-1 and ZF12× Hunt-Kox-1 repressor proteins are inserted into adeno-associated virus (AAV) vectors (AAV2/1 subtype; *Molecular Therapy* (2004) 10: 302-317). In parallel experiments, the zinc finger-AAV vectors are injected into the striatum of R6/2 mice in order to mediate expression of ZFP-Kox-1 fusion proteins in striatum cells. The ability of expressed ZFP-Kox-1 fusion proteins in striatum cells to reduce HD symptoms in R6/2 mice is assessed over a period of at least 20 weeks by periodically assessing the behaviour and symptoms of zinc finger-AAV infected R6/2 mice, as well as the expression levels of the mutant htt protein, in comparison to control R6/2 mice infected with a AAV-GFP control vector.

Timeline:

Week 0: New born R6/2 mice.

Week 4: Stereotaxic injection into the striatum of R6/2 mice with AAV—e.g. ZF6× Hunt-Kox-1-ires-GFP and control AAV-GFP.

Week 4 to 20: Weekly behavioural test: accelerating rotarod test, hind-limb clasping and stride length analysis.

Every two weeks: sacrifice of mice for qRT-PCR to check for reduction of expression of mutant HD fragments and immunohistochemistry to show a reduction in polyQ aggregates and expression of other neuronal markers such as DARPP-32 and NeuN.

ZFP-Kox1 fusion proteins of the invention are shown to reduce mutant htt protein expression, improve motor and neuropathological abnormalities, and prolong longevity (i.e. age of mice that naturally die before sacrifice), of R6/2 mice in comparison to negative controls.

Example 9

Striatal Delivery of Zinc Fingers in R6/2 Mice Causes Dose-dependent Repression of Mutant Huntingtin and Attenuates Disease Phenotypes The ZF11× Hunt-Kox-1 peptide was shown to be effective in inhibiting mutant htt expression in the STHdh model cell line (Example 5). Therefore, to test the ability of zinc finger peptides of the invention to treat/alleviate HD in vivo in an HD-mouse model we used AAV virus to deliver ZF11× Hunt-Kox-1 to the affected brain area in R6/2 mice.

ZFx Hunt Fused to Kox-1 Reduces Expression of Mutant Htt In Vivo

Female R6/2 mice were stereotaxically injected at 4 weeks of age with AAV2/1 virus expressing ZF11x Hunt-Kox-1, under a CAG-promoter with WPRE elements (Garg et al. (2004) *J. Immunol.*, 173: 550-558). Injections were into the striatum of one brain hemisphere, with AAV2/1-GFP control injections into the other.

Figure 8:
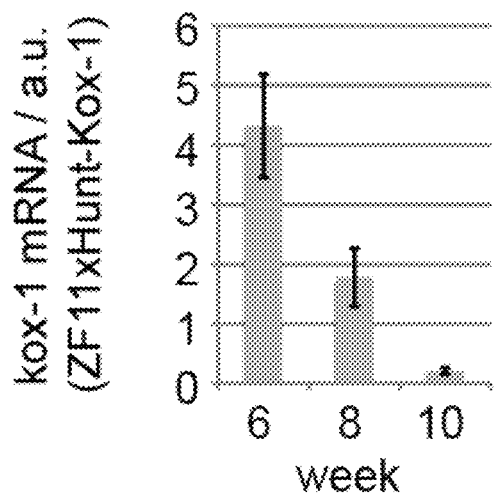
FIG. 8 Illustrates qRT-PCR data quantifying mRNA levels in mouse striatal samples injected with ZF11× Hunt-Kox-1. (A) Measurement of Kox-1 levels reveals peak zinc finger expression at 6 weeks with a steady decline thereafter. (B) Mutant huntingtin repression (mut htt) was repressed most at week 6 and is no longer significantly repressed by week 10. (C) Zinc finger treatment has no significant effect on wild-type huntingtin levels (wt htt).
Figure 8:
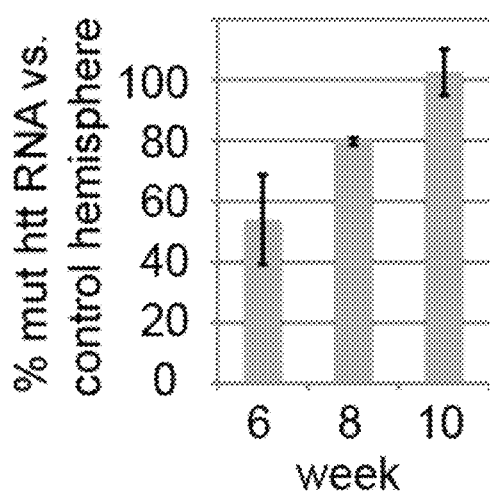
Figure 8:
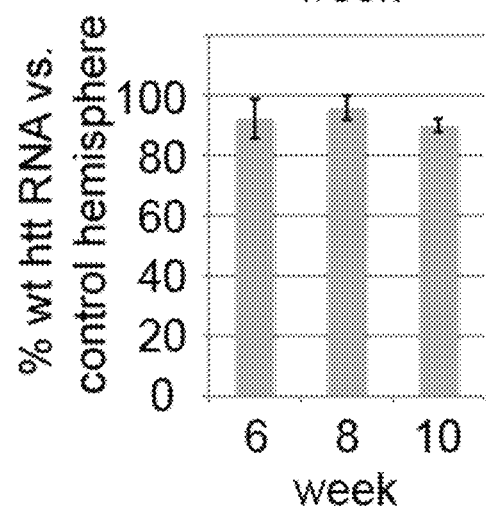

Analysis by qRT-PCR showed the highest expression levels of ZF11x Hunt-Kox-1 in the injected striatum of 6-week-old mice (see FIG. 8A). At the same time, the levels of the mutant htt transgene mRNA in these portions of the brain were reduced by over 45% (on average), as compared to measured levels in the control hemisphere (see FIG. 8B).

Furthermore, in linear regression analysis, it was noted that ZF11x Hunt-Kox-1 mRNA levels correlated negatively and closely with mutant htt mRNA levels (r-squared=0.79; p=0.0072), which is consistent with an in vivo dose-dependent repression of mutant htt by the zinc finger construct.

Repression levels of mutant htt mRNA reached up to 60% in some of the mice analysed at week 6. Notably, this repression was specific for mutant htt, since wt htt was unaltered at all time points analysed (see FIG. 8C). However, expression of the ZFP was significantly reduced by week 8, and concomitantly, repression levels of the htt gene, although still statistically-significant, dropped to 20% in comparison with the control hemisphere. By 10 weeks post-injection the ZFP expression levels were greatly reduced, and mutant htt levels were not reduced compared to the control hemisphere.

Similar results were obtained in mice injected in only one hemisphere with AAV-ZF11x Hunt-Kox-1, when compared to non-injected control hemispheres (data not shown).

ZFx Hunt-Kox-1 Delays the Expression of Behavioral Symptoms in R6/2 Mice

In a double blind experiment, male R6/2 mice and their wild-type littermates were treated in both hemispheres, at 4 weeks of age, with either AAV2/1-ZF11x Hunt-Kox-1 or AAV2/1-GFP (i.e. lacking a zinc finger repression protein). The general condition of the mice (body weight, grip strength, clasping behavior), and their performance in different behavioural motor tests (accelerating rotarod, activity in an open field, paw print) were analysed twice a month, from week 3 of age (pre-surgery).

Figure 9:
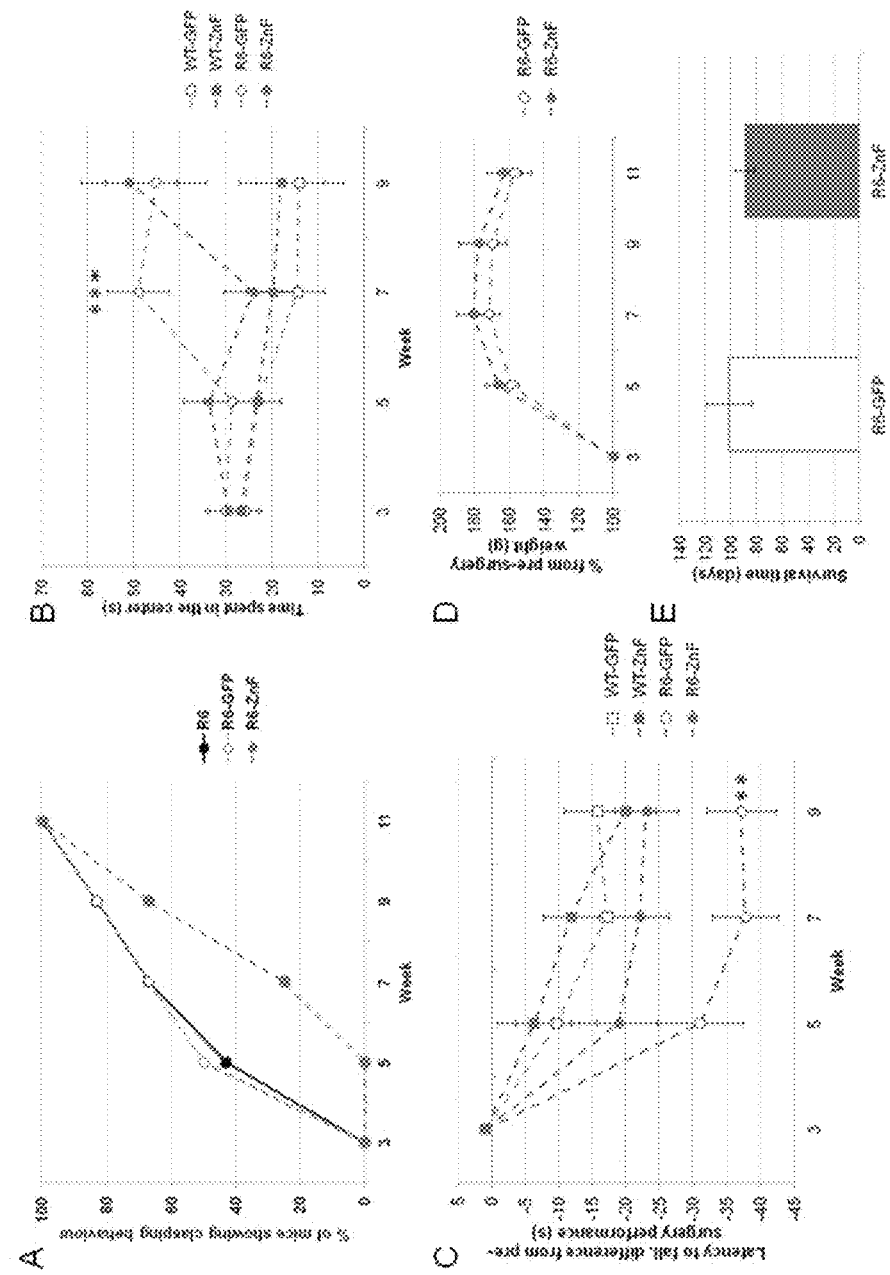
FIG. 9 Behavioural tests on the performance and general condition of R6/2 and wt male mice treated with either ZFP or GFP. (A) Graph showing results of clasping behavioural test. ZFP treatment resulted in a delay in the onset of clasping behaviour when compared with GFP-treated and non-operated R6/2 control mice. (B) Graph showing results of open field test. Increase of time spent in the centre of the open field was also delayed by the ZFP treatment at week 7. A significant difference was observed in R6/2-GFP mice at week 7 relative to all the other groups, but the effect had largely disappeared by week 9. (C) Graph showing results of rotarod test. The decline in the rotarod performance from pre-surgery levels was attenuated by ZFP. An ANOVA with repeated measures revealed that the R6/2-GFP group differed from WT-GFP, whereas R6/2-ZFP did not differ from its control WT-ZFP. (D) Graph showing body weight gain over the course of the experiment. Body weight gain was similar between both ZFP and GFP-treated mice, and started declining after week 7 of age, with no effect from the treatment. (E) Bar chart showing survival time. Survival was not significantly different between the groups of R6/2 mice. All data are presented as mean±S.E.M. , $p<0.01$. *, $p<0.001$.

Consistent with the observed peak of repression at 6-weeks of age (FIG. 8B), the greatest improvements in HD symptoms were found between weeks 5 and 7. For example, ZF11x Hunt-Kox-1 clearly delayed the onset of clasping behaviour in comparison to AAV2/1-GFP-treated or non-operated R6/2 control mice, as shown in FIG. 9A. Thus, whereas both GFP-treated and untreated R6/2 mice started clasping at week 5, this disease-behaviour was not detected at this time in any of the ZF11x Hunt-Kox-1 treated mice at 5 weeks of age. Furthermore, by week 7, when 67% of the mice in the control groups exhibited clasping, only 25% of the treated mice exhibited such behaviour.

In the open field test, distance travelled and mean speed did not vary between treated and untreated R6/2 mice. However, the time spent in the centre of the open field at week 7 was increased in GFP-treated mice, with respect to both groups of wild-type mice, but not in ZF11x Hunt-Kox-1 treated mice (Repeated Measures ANOVA: Groupx Week significant interaction, p<0.01; post-hoc pair-wise comparisons at week 7: WT-GFP versus R6/2-GFP, p<0.001; WT-ZF versus R6/2-ZF, n.s.), as indicated in FIG. 9B. This effect might be due to the difficulty for untreated R6/2 mice in initiating the movement of escape towards the periphery of the open field, or simply due to a decreased reactivity.

In the accelerating rotarod test, treatment with ZF11x Hunt-Kox-1 was also found to attenuate the decline of performance with age, with respect to pre-surgery levels (Repeated measures ANOVA: significant main effect of Group, p<0.05; post-hoc comparisons between groups: WT-GFP vs R6/GFP, p<0.05; WT-ZF vs R6/2-ZF, n.s.), and the results are displayed in FIG. 9C.

However, the grip strength and gait parameters measured in the paw print test did not reveal any notable difference between the groups, and neither did weight loss or survival time (see FIG. 9D).

In summary, the in vivo data in Huntington's disease models are consistent with a partial improvement in symptoms due to zinc finger repressor protein expression, which was coincident with a peak in zinc finger repression at 6 weeks. However, the loss in ZFP expression over time allowed the symptoms of HD to return in the treated mice, indicated that control and treatment of symptoms is transient: i.e. dependent on ZFP-repressor expression in these tests. Although the CAG-WPRE system is already designed to be an improvement on previous expression constructs (Garg et al. (2004) *J. Immunol.*, 173: 550-558), it is possible that further improvements might be achievable if zinc finger expression level and duration were increased. Hence, the data provided here demonstrates both zinc finger-mediated repression of the htt gene in vivo, and partial disease phenotype amelioration.

Example 10

ZFx Hunt Sequence Variants for Improved Viral Packaging

The QRATLQR (SEQ ID NO: 1) zinc finger helix was rationally designed, as described elsewhere in this document, and was demonstrated to bind htt DNA specifically with high affinity, when concatenated into long ZFP chains. However, this necessitates making highly-repetitive DNA and protein expression constructs, which in some cases may be suboptimal for viral packaging in AAV2 gene therapy applications.

Therefore, to devise a solution to this potential problem we decided to make a number of variants of the ZFP that conserve the desired nucleic acid recognition/DNA-binding functionality of the ZFPs described herein. Accordingly, the amino acid sequences of the nucleic acid recognition helices were varied slightly using known zinc finger-nucleic acid recognition rules (e.g. as reviewed in Pabo et al. (2001), *Annu. Rev. Biochem.* 70: 313-340).

It is also possible to vary ZFP backbone sequences conservatively without affecting zinc finger functionality. Therefore, in one or more zinc finger domains, the backbone residues forming the beta-beta-alpha-fold may also be varied to avoid undesirable repetition of sequences.

Furthermore, as already discussed above, the ZFP linker sequences between adjacent zinc finger domains may also be varied in sequence, if desired.

In this Example, therefore, to optimise viral packaging we made several ZF× Hunt variants, including the sequence exemplified below (SEQ ID NO: 108), which has slightly-altered zinc finger backbones and α-helices, and tested for binding to the appropriate CAG-repeat target sequences. The altered backbones are based on different DNA-binding zinc finger sequences, including fingers from wild-type zif268 and sp1. Furthermore, in order to reduce AAV2 construct size by approx. 240 bp, FLAG-epitope tag and one ZF× Hunt domain were also removed, resulting in a viral package of optimum size encoding a 10-finger peptide.

Figure 10:
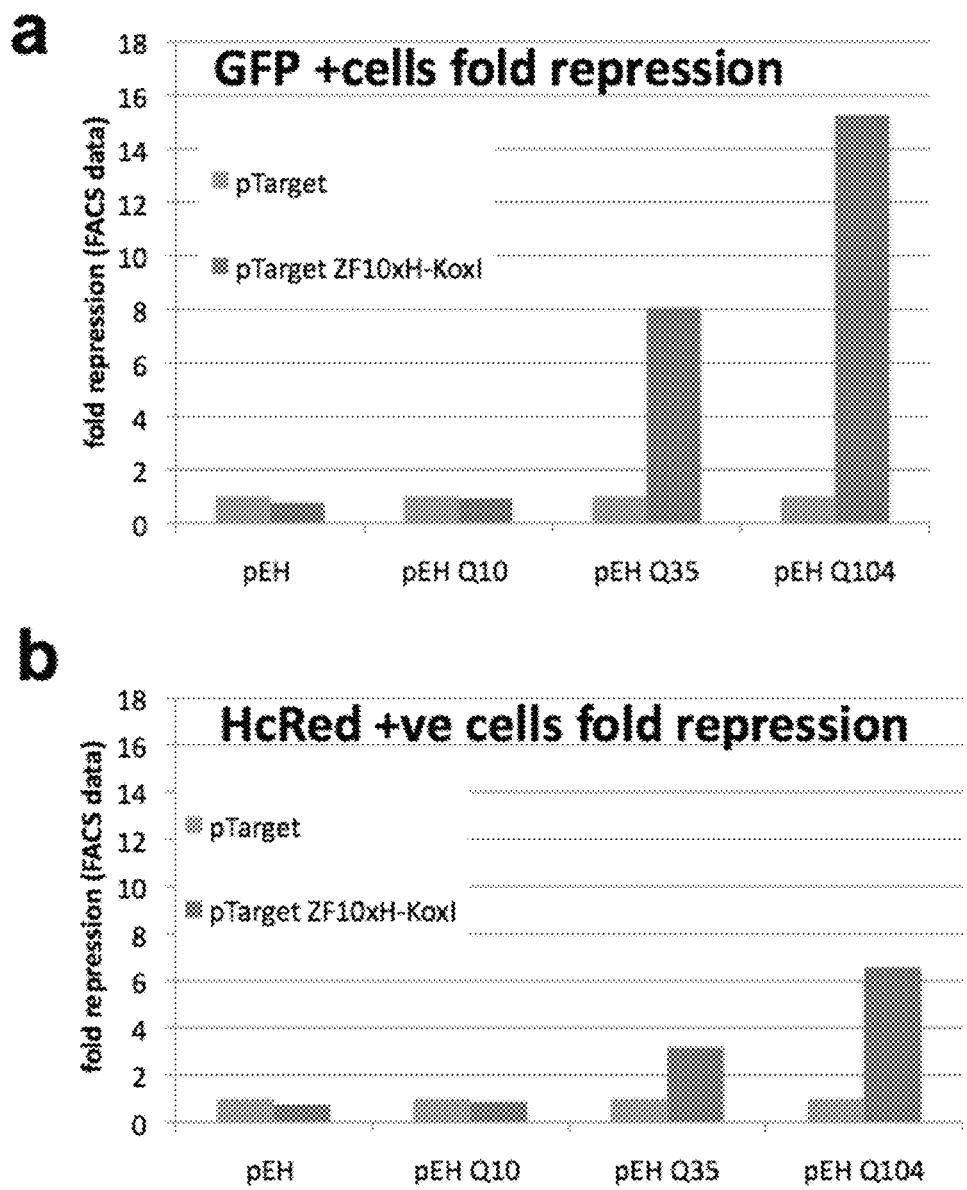
FIG. 10 Repression of poly-CAG constructs by ZF10× Hunt (SEQ ID NO: 108) containing conservative variant sequences in the nucleic acid recognition helix. An episomal assay was used including transient transfection followed by FACS for fluorescent cells. The poly-CAG-GFP reporter constructs code for 0 (pEH), 10 (Q10), 35 (Q35), and 104 (Q104) CAG-repeats, respectively. (a) ZF10× Hunt-Kox-1 zinc fingers repress the fused GFP reporter gene. For comparison, the pTarget control contains no zinc fingers. (b) Kox-1-ZFP fusions also slightly repress a control HcRed gene on the same plasmid.

The resultant ZF10× Hunt ZFP targets and binds repetitive CAG sequences with high affinity and specificity, as do the previously described ZFPs. Moreover, the ZF10× Hunt ZFP was shown to retain strong HTT-repression activity in episomal assays, as shown in FIG. 10. An episomal assay was used, which involved transient transfection followed by FACS for fluorescent cells. The poly-CAG-GFP reporter constructs code for 0 (pEH), 10 (Q10), 35 (Q35), and 104 (Q104) CAG-repeats, respectively. As shown in FIG. 10(a) ZF10× Hunt-Kox-1 zinc fingers repress the fused GFP reporter gene. For comparison, the pTarget control contains no zinc fingers. However, as shown in FIG. 10(b), the Kox-1-ZFP fusions also slightly repressed a control HcRed gene on the same plasmid, which effect is likely to be due to the recruitment of chromatin repression factors.

TABLE 4

ZF10xHunt amino acid and encoding nucleic acid sequences. In amino acid sequences recognition sequences are underlined and linker sequences are shown in bold. The mutated amino acids in the recognition sequences are shown in lowercase.

ZF10xHunt amino acid sequence (SEQ ID NO: 108):
YACPVESCDRRFSQRATLtRHIRIH TGQKP

FQCRI CMRNFSQRATLsRHIRTH QNKKGS

HICHIQGCGKVYGQRATLQRHLRWH TGERP

FMCTWSYCGKRFTQRATLQRHKRTH LRQKDGERP

YACPVESC DRRFSQRATLsRHIRIH TGEKP

YKCPE CGKSFSQRATLQRHQRTH TGSERP

FMCNWSYCGKRFTQRATLtRHKRTH TGEKP

FACPE CPKRFMQRATLQRHIKTH TGSEKP

FQCRI CMRNFSQRATLQRHIRTH TGERP

FACDI CGRKFAQRATLQRHTKIH

ZF10xHunt nucleic acid sequence (SEQ ID NO: 109):
TACGCCTGCCCTGTGGAGTCCTGCGATAGAAGATTTTCCCAGAGAGCAA

CCCTGACCAGACATATTCGGATTCACACCGGCCAGAAGCCATTCCAGTG

CAGAATCTGTATGCGGAACTTTTCCCAGAGAGCCACACTGTCTCGGCAC

ATTCGCACTCATCAGAATAAGAAAGGGTCTCACATCTGCCATATTCAGG

GGTGTGGCAAAGTGTATGGACAGCGAGCCACCCTGCAGCGACACCTGAG

GTGGCATACCGGAGAGAGGCCCTTCATGTGCACATGGAGTTACTGTGGC

TABLE 4-continued

ZF10xHunt amino acid and encoding nucleic acid sequences. In amino acid sequences recognition sequences are underlined and linker sequences are shown in bold. The mutated amino acids in the recognition sequences are shown in lowercase.

AAGAGGTTCACCCAGCGAGCTACACTGCAGAGACACAAACGGACACATC

TGCGACAGAAGGACGGAGAGCGACCATATGCATGCCCAGTCGAAAGTTG

TGATAGGAGATTCTCACAGCGCGCTACTCTGAGCCGCCACATCCGAATT

CATACCGGCGAGAAACCTTACAAGTGCCCAGAATGTGGAAAGAGCTTTT

CCCAGAGAGCAACTCTGCAGAGGCACCAGAGAACCCATACAGGCAGTGA

GCGGCCCTTCATGTGCAACTGGTCATATTGTGGAAAAAGGTTTACCCAG

AGAGCTACTCTGACCCGGCACAAACGCACACATACTGGCGAGAAGCCTT

TCGCTTGCCCCGAATGTCCTAAGCGGTTTATGCAGCGCGCAACACTGCA

GCGGCACATCAAAACCCATACAGGAAGCGAGAAGCCTTTCCAGTGCCGA

ATTTGTATGAGGAATTTTTCCCAGAGGGCAACTCTGCAGCGACACATCA

GGACTCATACCGGGGAACGGCCATTCGCCTGCGACATTTGTGGCAGAAA

ATTTGCACAGCGAGCTACTCTGCAGCGACACACCAAAATCCAC

ZF10xHunt C-terminal linker and Kox-1 repressor peptide (SEQ ID NO: 110):
LRQKDA PKKKRKV GGS LSPQHSAVTQGSIIKNKEGMDAKSLTAWSR

TLVTFKDVFVDFTREEWKLLDTAQQIVYRNVMLEN YKNLVSLGYQLTK

PDVILRLEKGEEPWLVEREIHQETHPDSETAFEIKSSV*

ZF10xHunt C-terminal linker and Kox-1 repressor nucleic acid (SEQ ID NO: 111):
CTGCGCCAGAAGGATGCTCCCAAGAAAAAGAGGAAAGTGGGCGGATCTC

TGAGTCCTCAGCACTCCGCAGTCACCCAGGGATCTATCATCAAGAACAA

GGAGGGGATGGACGCAAAGTCACTGACAGCCTGGAGCCGCACACTGGTG

ACTTTCAAAGACGTGTTCGTCGACTTCACCAGGGAGGAATGGAAGCTGC

TGGACACTGCCCAGCAGATCGTGTACAGGAATGTCATGCTGGAAAACTA

TAAGAATCTGGTGAGCCTGGGATACCAGCTGACCAAACCAGATGTCATT

CTGAGACTGGAGAAGGGGGAGGAACCCTGGCTGGTGGAACGGGAGATTC

ATCAGGAAACCCACCCAGATTCAGAGACAGCATTTGAGATTAAGTCATC

CGTC

ZF× Hunt Variants

To demonstrate that the desirable binding activity for the CAG-repeat nucleic acid target sequences is not limited solely to the α-helix amino acid recognition sequences exemplified above, further ZF× Hunt sequence variants were constructed and tested for binding activity. Mutations to the ZFP sequences of the invention described in the above Examples were focussed primarily in the α-helix recognition sequences.

Functional, conservative sequence variations were made in the amino acid sequences of various α-helices of the ZFPs, and the resultant ZFPs were shown to bind poly-CAG sequences. Exemplary recognition sequences are shown in Table 5. In the table below, the original recognition sequences of the ZFPs are shown aligned with the target nucleic acid sequence (above) with exemplary conservative variant sequences (below). As shown, up to 50% of the recognition sequence may be varied using conservative substitutions.

TABLE 4

Top-zinc finger helices are shown in the N-C terminal protein direction, aligned 3'-5' to the primary DNA recognition strand. Top/middle-functionally-conservative mutations are underlined in recognition sequences (top and middle). Bottom-generic sequence for binding CAG-repeat sequences shown. The variant zinc fingers can be combined in any number and order and function in zinc finger scaffolds of different lengths, including ZF11xHunt. Table 4 discloses the 'wt ZFxHunt' sequences as six repeats of SEQ ID NO: 1, the DNA sequence as SEQ ID NO: 98 and the 'variant ZFxHunt' sequences as SEQ ID NOS: 103-106, 1 and 107, respectively, in order of appearance.

```
Amino acid- nucleic acid recognition alignment
wt ZFxHunt
QRATLQR QRATLQR QRATLQR QRATLQR QRATLQR QRATLQR ... etc (e.g. 11 repeats)
  | | | | | | | | | | | | | | | | | | | | |
3'-a c g a c g a c g a c g a c g a c g-5' DNA
  | | | | | | | | | | | | | | | | | | | | |
QRATLSR QLATLQR QSSVLQR QSADLTR QRATLQR QSSELQR ... etc (e.g. 11 repeats)
variant ZFxHunt
```

Exemplary CAG recognition sequence variants

QRATLQR (SEQ ID NO: 1)

QRATLTR (SEQ ID NO: 102)

QRATLSR (SEQ ID NO: 103)

QLATLQR (SEQ ID NO: 104)

QSSVLQR (SEQ ID NO: 105)

QSADLTR (SEQ ID NO: 106)

QSSELQR (SEQ ID NO: 107)

Generic CAG recognition sequence

Q(R/L/S)(A/S)(T/V/D/E)L(Q/T/S)R (SEQ ID NO: 101)

Discussion

In these Examples, we have described the design of zinc finger peptides able to recognise and bind both DNA strands of a stretch of CAG repeats, by recognising both poly-GCA and poly-GCT triplets; and shown that such proteins are able to induce transcription repression of target genes both in vitro and in vivo.

Recently, Mittelman et al. (2009), *Proc. Natl. Acad. Sci. USA* 106(24): 9607-9612 employed a different ZFP approach for exploring CAG-tract instability, after inducing double-stranded breaks with paired 3-finger Fok-I nuclease fusions. They described two ZFP proteins, zfGCT (alpha-helical recognition sequence: QSSDLTR; (SEQ ID NO: 96) and zfGCA (QSGDLTR; SEQ ID NO: 97), designed to recognize GCT and GCA, respectively. Cleavage events inducing CAG-tract shortening were observed in up to 1 in $10^4$ cell colonies.

Figure 3:
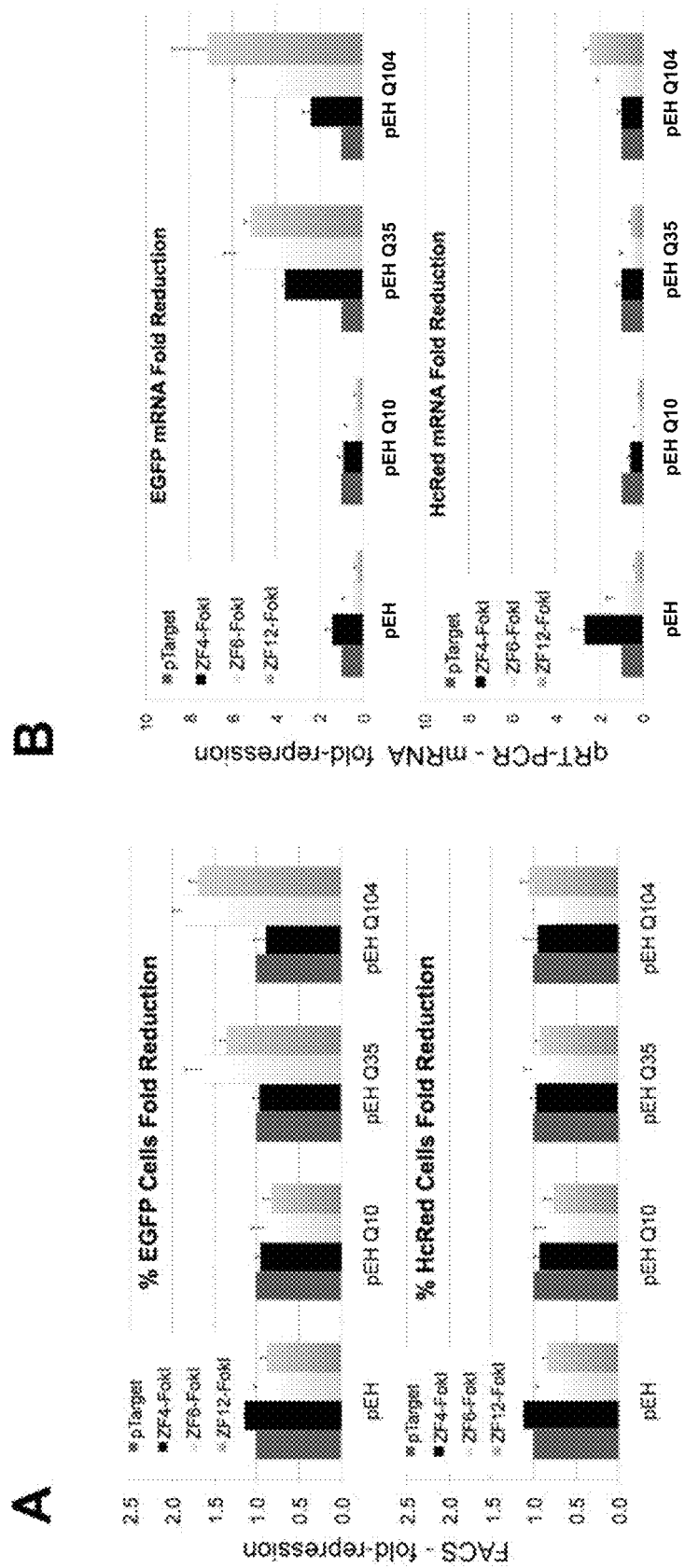
FIG. 3 Episomal reporter repression by ZF× Hunt-FokI. Cells were cotransfected with reporter and ZFP-Fok1 expression plasmids: the pEH reporter plasmid contains EGFP, fused to different-length poly-Q coding sequences, under an SV40 promoter. A control HcRed gene, under a CMV promoter measures off-target or long-range repression. ZF-FokI (CMV-promoter) expression constructs contain chains of ZF× Hunt (0, 4, 6 or 12 fingers, as indicated). The pTarget vector does not contain ZFP and is used as a control. (A) FACS assay measuring the fold-reduction in EGFP or HcRED fluorescent cells, in response to different zinc fingers. A 2.5-fold repression is equivalent to 60% reduction. (B) gRTPCR assay to measure fold-repression of EGFP or HcRED mRNA by ZFP. (C) EGFP Western blot for ZFP repression of pEH-Qx targets. β-actin staining is used as a loading control.
Figure 3:
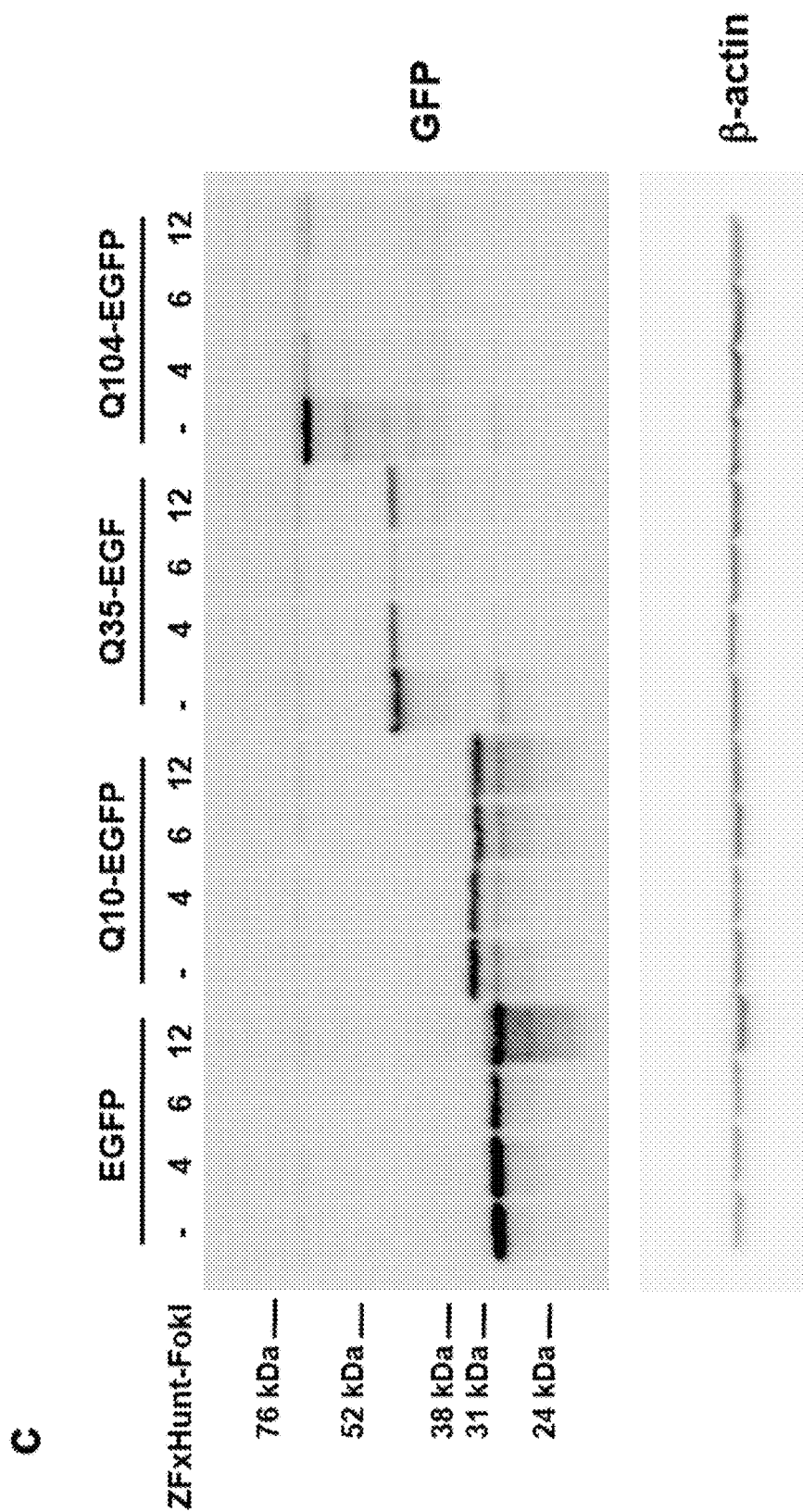

We also originally tested the zinc finger peptides of the invention, ZFx Hunt (with recognition sequence, QRATLQR; SEQ ID NO: 1) as fusions to FokI and found that they reduced poly-CAG-EGFP transcription in a similar way to naked ZFP (FIG. 3). This effect is much stronger than a nuclease effect since GFP is repressed in up to approximately 85% of cells—as assessed by FACS of transiently-transfected cells. Furthermore, the effect is believed to be at the RNA level since both RNA and protein levels were reduced (FIG. 3). Reporter plasmids were extracted from transfected cells and sequenced to look for non-homologous-end-joining frameshifts that could explain the observed EGFP repression (i.e. up to approximately 85% reduction). However, we were unable to detect any non-homologous-end-joining frameshifts in the 30 plasmids that were extracted from and sequenced. This suggests that the transcriptional repression effects of the zinc finger peptides simply through binding to their target sequences is far stronger than any possible nuclease effects; and indicates that the mechanism of action of the ZFx Hunt peptides of the invention is entirely different to the mechanism reported by Mittelman et al.

We have also demonstrated that naked zinc finger peptides (i.e. lacking additional effector domains) can be highly efficient inhibitors of target gene expression (polyQ-EGFP expression was reduced by up to 90%), particularly when the number of CAG-repeats is equal or superior to 35. This is a significant finding, since the number of CAG-repeats in wild-type genes in the human genome (including the htt gene), is less than 35. Without being bound by theory, it is likely that the mechanism of repression in these cases is due to steric hindrance of RNA polymerase complex progression, as reported by Choo et al. for a synthetic ZFP against the Bcr-Abl oncogene (Choo et al. (1994) *Nature* 372(6507): 642-645).

Fusing the Kox-1 repression domain to the zinc finger peptides of the invention was found to further reduce expression of targeted genes. In these experiments, it was demonstrated that repression required binding to CAG repeats, since control vectors lacking CAG repeats were not affected. However, in some cases there was also a repressive effect on a neighbouring reporter gene control, HcRed, especially for the longer targets. This non-specificity, however, is likely to be an effect of the specific repressor domain rather than of the zinc finger peptide: Kox-1 is known to recruit the co-repressor KAP-1 and induces long-range repression through the spread of heterochromatin (Groner et al. *PLoS Genet.* 6(3): e1000869).

Although partial reduction of the shorter wild-type htt protein has been shown to be tolerated for up to 4 months in animal models (Boudreau et al. (2009) *Mol. Ther.* 17(6): 1053-1063), it is generally considered that a safe and effective therapy for HD should preferentially target the mutant htt allele. Using a competition assay, it has been shown that the zinc finger peptides of the invention preferentially repress the expression of reporter genes containing over 35 CAG repeats, which suggests that they hold significant promise for a therapeutic strategy to reduce the levels of mutant huntingtin protein in heterozygous patients.

It is worth noting that there are some relevant differences between plasmid and chromosomal repression, which presumably reflect target copy number and accessibility within chromatin. Episomally, 6-finger peptides alone have been shown to be effective repressors of target genes. However, Kox-1 repression appears to be too strong for optimal length-discrimination. Conversely, at endogenous loci, the Kox-1 fusion proteins appear to be better for mutant repression, while eschewing the wild-type allele. In this case, the 6- and 11-finger Kox-1 constructs are strong repressors of both target protein and RNA expression. After 20 days of stable expression of the zinc finger peptides, the 11-finger protein was found to exhibit the strongest repression of the target mutant allele. In fact, when fused to the Kox-I repression domain, the most active zinc finger peptides of the invention were able to dramatically reduce the levels of the endogenous mutant protein by 95%, and the levels of the mutant mRNA by approximately 80%, with negligible effect on the expression of the wild-type allele, or on any other genes containing a wild-type number of CAG repeats. Sustained therapeutic expression is therefore potentially feasible.

Gene therapy is an attractive therapeutic strategy for various neurodegenerative diseases. For example, lentiviral vectors have been used to mediate the widespread and long-term expression of transgenes in non-dividing cells such as mature neurons (Dreyer, *Methods Mol. Biol.* 614: 3-35). An rAAV vector was also used by Rodriguez-Lebron et al. (2005) *Mol. Ther.* 12(4): 618-633, to deliver anti-mutant Htt shRNAs in HD model mice; thereby reducing striatal mHtt levels and slowing progression of the HD-like phenotype. Moreover, as RNAi (van Bilsen et al. (2008) *Hum. Gene Ther.* 19(7): 710-719; Zhang et al. (2009) *J. Neurochem.* 108(1): 82-90; Pfister et al. (2009) *Curr. Biol.* 19(9): 774-778), and LNAs (Hu et al. (2009) *Nat. Biotechnol.* 27(5): 478-484; and Hu et al. (2009) *Ann. NY Acad. Sci.* 1175: 24-31) have recently shown promise for treating HD, suitable delivery vehicles are likely to be optimised in the years ahead, and the complementary ZFP approach described here would likely benefit from such advances.

Accordingly, a model cell line derived from striatal cells of a knock-in HD mouse model (Trettel et al. (2000) *Hum. Mol. Genet.* 9(19): 2799-2809) has been developed and used to demonstrate the effects of the zinc finger peptides of the invention under likely therapeutic conditions (i.e. single-copy alleles in chromosomal loci).

rAAV appeared as a promising delivery system, and so we used it to deliver the ZF11x Hunt-Kox-1 gene to the striatum of the R6/2 model mouse for HD. We initially produced and tested AAV2/1 expressing the ZFP under a CMV promoter, but we observed very low levels of expression of the ZFP and its mRNA, and no repression of mutant htt (data not shown). CMV promoters can be quickly silenced by DNA methylation (Migliaccio et al. (2000) *Gene*, 3, 256(1-2): 197-214), whereas high and persistent levels of expression can be achieved in the central nervous system with rAAV using the CAG promoter and a WPRE (reviewed in Tenenbaum et al. (2004) *J. Gene Med.*, 6 Suppl 1: S212-22). We therefore produced a new rAAV using these elements, and noticed a significantly improved expression compared to rAAV-CMV. With improved expression, we observed a significant repression of the mutant htt transgene in R6/2 brain striatum, compared to control striatum, while expression of the wt gene was unaltered. However, even with the improved rAAV expression construct, we observed reduced expression of the ZFP over time, with a concomitant reduction in mutant htt repression. Decreased expression of the ZFP over time might be due to promoter silencing, as in the case of the CMV promoter, or to instability of the ZFP DNA that remains as extra-chromosomal DNA in quiescent striatal cells.

Co-incident with the reduced mutant htt expression levels at 6-8 weeks of age, mice showed a delay in the onset of many HD-like symptoms characteristic of the R6/2 model line. Specifically, we found a delay in the onset of clasping behaviour, as well as an attenuation of the deficits in the accelerating rotarod (Menalled et al. (2009) *Neurobiol. Dis.* 35: 319-336). However, since ZFP-repressor expression had dropped off by weeks 9 to 10, we were unable to demonstrate, in these studies, an improved grip strength (which only starts to decline at around week 9), improved gait and locomotion parameters, or improved survival time and body weight. It is likely that this is related to the transient repression seen in our brain samples, so that any effects seen are due to an acute effect of the treatment and not to a failure of the ZFP to repress the target mutant htt gene.

Overall, the results presented in this study establish that the ZFPs can repress mutant htt in vivo (via striatal injection), in a dose-dependent manner; and that, as a result, there are some clear behavioural improvements and reduction in Huntington's disease symptoms. We believe that these results and the treatment of Huntington's disease would be improved still further by higher expression levels of the ZFPs and/or by the maintenance of expression over longer time-periods.

In conclusion, since reducing mutant huntingtin protein levels improves motor and neuropathological abnormalities, and also prolongs longevity in HD mouse models (Rodriguez-Lebron et al. (2005) *Mol. Ther.* 12(4): 618-633; Harper et al. (2005) *Proc. Natl. Acad. Sci. USA* 102(16): 5820-5825; Wang et al. (2005) *Neurosci. Res.* 53(3): 241-249; and Harper (2009) *Arch. Neurol.* 66(8): 933-938), the zinc finger proteins developed here hold great promise for treating polyglutamine-based diseases; as well as other genetic disorders associated with repeat sequences, e.g. trinucleotide repeats having at least 10 repeats.

The invention claimed is:

1. A polynucleotide which encodes a zinc finger peptide comprising the sequence:

N'-[(Formula 2)-$X_6$]$n_0$-{[(Formula 2)-$X_5$-(Formula 2)-$X_6$]$_{n1}$-[(Formula 2)-$X_5$-(Formula 2)-$X_L$]}$_{n2}$-[(Formula 2)-$X_5$-(Formula 2)-$X_6$]$_{n3}$-[(Formula 2)-$X_5$-(Formula 2)]-[$X_6$-(Formula 2)]$_{n4}$—C', wherein $n_0$ is 0 or 1, $n_1$ is from 1 to 4, $n_2$ is 1 or 2, $n_3$ is from 1 to 4, $n_4$ is 0 or 1, $X_5$ is a linker sequence of 5 amino acids, $X_6$ is a linker sequence of 6 or 7 amino acids, and $X_L$ is a linker sequence of at least 8 amino acids, and Formula 2 is a zinc finger domain of the sequence-$X_{0\text{-}2}$ C $X_{1\text{-}5}$ C $X_{2\text{-}7}$ $X^{-1}$ $X^{+1}$ $X^{+2}$ $X^{+3}$ $X^{+4}$ $X^{+5}$ $X^{+6}$ H $X_{3\text{-}6}$ $^H/_C$—, wherein X is any amino acid, the numbers in subscript indicate the possible numbers of residues represented by X at that position, and the number in superscript indicates the position of the amino acid in the recognition sequence of the zinc finger domain;

wherein the zinc finger peptide comprises from 8 to 32 zinc finger domains, comprises at least the sequence of SEQ ID NO: 6, SEQ ID NO: 8, SEQ ID NO: 10, SEQ ID NO: 12, SEQ ID NO: 14 or SEQ ID NO: 108, or a sequence having at least 90% identity thereto, and wherein at least one zinc finger domain has a $X^{-1}$ $X_{+1}$ $X^{+2}$ $X^{+3}$ $X^{+4}$ $X^{+5}$ $X^{+6}$ recognition sequence according to SEQ ID NO: 101.

2. The polynucleotide of claim 1, wherein the encoded zinc finger peptide comprises the sequence:

N'-[(Formula 6)-L3]$_{n0}$-{[(Formula 6)-L2-(Formula 6)-L3]$_{n1}$-[(Formula 6)-L2-(Formula 6)-$X_L$]}$_{n2}$-[(Formula 6)-L2-(Formula 6)-L3]$_{n3}$-[(Formula 6)-L2-(Formula 6)]-[L3-(Formula 6)-]$_{n4}$—C', wherein $n_0$ is 0 1, $n_1$ is 1 or 2, $n_2$ is 1 or 2, $n_3$ is 2, $n_4$ is 0, $X_L$ is 11 to 40 amino acids, L2 has the sequence TG$^E/_Q$$^K/_R$P—, L3 has the sequence TG$^G/_S$$^E/_Q$$^K/_R$P—, and Formula 6 has the sequence-$X_2$ C $X_2$ C $X_5$ $X^{-1}$ $X^{+1}$ $X^{+2}$ $X^{+3}$ $X_{+4}$ $X^{+5}$ $X^{+6}$H $X_3$ H -(SEQ ID NO: 113), wherein X is any amino acid.

3. The polynucleotide of claim 1, wherein the encoded zinc finger peptide comprises at least 8 zinc finger domains of SEQ ID NO: 113, wherein each $X^{-1}$ $X^{+1}$ $X^{+2}$ $X^{+3}$ $X^{+4}$ $X^{+5}$ $X^{+6}$ is selected from the group consisting of: SEQ ID NO: 1, SEQ ID NO: 101, SEQ ID NO: 102, SEQ ID NO: 103, SEQ ID NO: 104, SEQ ID NO: 105, SEQ ID NO: 106, and SEQ ID NO: 107 or combinations thereof.

4. The polynucleotide of claim 1, wherein the encoded zinc finger peptide comprises 10, 11, 12 or 18 zinc finger domains.

5. The polynucleotide of claim 1, wherein each $X^{-1}$ $X^{+1}$ $X^{+2}$ $X^{+3}$ $X^{+4}$ $X^{+5}$ $X^{+6}$ sequence of the encoded zinc finger peptide is identical to QRATLQR (SEQ ID NO: 1) at 4, 5, 6 or 7 positions.

6. The polynucleotide of claim 1, wherein at least 1, at least 4, at least 6, at least 8, at least 10, at least 11, at least 12, or at least 18 $X^{-1}$ $X^{+1}$ $X^{+2}$ $X^{+3}$ $X^{+4}$ $X^{+5}$ $X^{+6}$ sequences of the encoded zinc finger peptide are the sequence QRATLQR (SEQ ID NO: 1).

7. The polynucleotide of claim 1, wherein the encoded zinc finger peptide comprises the sequence of SEQ ID NO: 6, SEQ ID NO: 8, SEQ ID NO: 10, SEQ ID NO: 12, SEQ ID NO: 14 or SEQ ID NO: 108, or a sequence having at least 95% sequence identity thereto.

8. A polynucleotide encoding a zinc finger peptide having at least 90% sequence identity to a sequence selected from the group consisting of: SEQ ID NO: 6, SEQ ID NO: 8, SEQ ID NO: 10, SEQ ID NO: 12, SEQ ID NO: 14 and SEQ ID NO: 108.

9. The polynucleotide of claim 1, wherein the encoded zinc finger peptide is a fusion protein comprising the zinc finger peptide and at least one effector domain, selected from transcriptional repressor domains, transcriptional activator domains, transcriptional insulator domains, chromatin remodelling, condensation or decondensation domains, nucleic acid or protein cleavage domains, dimerisation or multimerization domains, enzymatic domains, signalling / targeting sequences or domains.

10. The polynucleotide of claim 9, wherein the at least one effector domain of the encoded zinc finger peptide comprises a Kox-1 transcription repressor domain.

11. The polynucleotide of claim 1, which comprises a nucleic acid sequence selected from SEQ ID NO: 7, SEQ ID NO: 9, SEQ ID NO: 11, SEQ ID NO: 13, SEQ ID NO: 15 or SEQ ID NO: 109.

12. A vector comprising the polynucleotide of claim 1.

13. A nucleic acid expression construct comprising the polynucleotide of claim 1 operably linked to a transcriptional promoter sequence.

14. A vector comprising the nucleic acid expression construct of claim 13.

15. The vector of claim 14, which is a viral vector or a non-viral vector, wherein the viral vector is selected from the group consisting of retroviruses adenoviruses; adeno-associated viruses (AAV); herpes simplex virus (HSV); and chimeric viruses; or a non-viral vector.

16. An adeno-associated virus (AAV) vector comprising the nucleic acid expression construct of claim 13.

17. The vector of claim 15, wherein the retroviral vector is selected from influenza, SIV, HIV, lentivirus and Moloney murine leukaemia.

18. The adeno-associated virus vector of claim 16, wherein the adeno-associated virus vector is AAV subtype 2/1.

\* \* \* \* \*

SEQUENCE LISTING

<160> NUMBER OF SEQ ID NOS: 120

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Arg Ala Thr Leu Gln Arg
1               5

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6
<211> LENGTH: 108
<212> TYPE: PRT
<213> ORGANISM: Artificial Sequence
<220> FEATURE:
<223> OTHER INFORMATION: Description of Artificial Sequence: Synthetic
      zinc finger polypeptide

<400> SEQUENCE: 6

Phe Gln Cys Arg Ile Cys Met Arg Asn Phe Ser Gln Arg Ala Thr Leu
1               5                   10                  15

Gln Arg His Ile Arg Thr His Thr Gly Glu Lys Pro Phe Ala Cys Asp
            20                  25                  30

Ile Cys Gly Arg Lys Phe Ala Gln Arg Ala Thr Leu Gln Arg His Thr
        35                  40                  45

Lys Ile His Thr Gly Ser Glu Arg Pro Phe Gln Cys Arg Ile Cys Met
    50                  55                  60

Arg Asn Phe Ser Gln Arg Ala Thr Leu Gln Arg His Ile Arg Thr His
65                  70                  75                  80

Thr Gly Glu Lys Pro Phe Ala Cys Asp Ile Cys Gly Arg Lys Phe Ala
                85                  90                  95

Gln Arg Ala Thr Leu Gln Arg His Thr Lys Ile His
            100                 105

<210> SEQ ID NO 7
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide encoding synthetic zinc finger peptide

<400> SEQUENCE: 7

```
ttccagtgcc gcatttgtat gcgcaacttt agccagcgcg cgaccctgca gcgtcatatt      60
cgcacccata ccggtgaaaa accgtttgcg tgcgatattt gcggtcgtaa atttgcgcag     120
cgtgcgaccc tgcagcgcca taccaaaatt cacaccggat ccgaacggcc gtttcagtgc     180
aggatttgca tgcgtaattt ttcccagcgc gcgaccctgc agcgccatat tcgcacccat     240
actggtgaaa aaccgtttgc ctgcgatatt tgcggtcgta aatttgcgca gcgtgctacc     300
ttacagcgcc ataccaaaat tcat                                            324
```

<210> SEQ ID NO 8
<211> LENGTH: 165
<212> TYPE: PRT
<213> ORGANISM: Artificial Sequence
<220> FEATURE:
<223> OTHER INFORMATION: Description of Artificial Sequence: Synthetic
      zinc finger polypeptide

<400> SEQUENCE: 8

```
Phe Gln Cys Arg Ile Cys Met Arg Asn Phe Ser Gln Arg Ala Thr Leu
1               5                   10                  15

Gln Arg His Ile Arg Thr His Thr Gly Glu Lys Pro Phe Ala Cys Asp
            20                  25                  30

Ile Cys Gly Arg Lys Phe Ala Gln Arg Ala Thr Leu Gln Arg His Thr
        35                  40                  45

Lys Ile His Thr Gly Ser Glu Arg Pro Phe Gln Cys Arg Ile Cys Met
    50                  55                  60

Arg Asn Phe Ser Gln Arg Ala Thr Leu Gln Arg His Ile Arg Thr His
65                  70                  75                  80

Thr Gly Glu Lys Pro Phe Ala Cys Asp Ile Cys Gly Arg Lys Phe Ala
                85                  90                  95

Gln Arg Ala Thr Leu Gln Arg His Thr Lys Ile His Thr Gly Ser Glu
            100                 105                 110

Arg Pro Phe Gln Cys Arg Ile Cys Met Arg Asn Phe Ser Gln Arg Ala
        115                 120                 125

Thr Leu Gln Arg His Ile Arg Thr His Thr Gly Glu Lys Pro Phe Ala
    130                 135                 140

Cys Asp Ile Cys Gly Arg Lys Phe Ala Gln Arg Ala Thr Leu Gln Arg
145                 150                 155                 160

His Thr Lys Ile His
                165
```

<210> SEQ ID NO 9
<211> LENGTH: 495
<212> TYPE: DNA
<213> ORGANISM: Artificial Sequence
<220> FEATURE:
<223> OTHER INFORMATION: Description of Artificial Sequence: Synthetic
      polynucleotide encoding synthetic zinc finger peptide

```
<400> SEQUENCE: 9
ttccagtgcc gcatttgtat gcgcaacttt agccagcgcg cgaccctgca gcgtcatatt      60
cgcacccata ccggtgaaaa accgtttgcg tgcgatattt gcggtcgtaa atttgcgcag     120
cgtgcgaccc tgcagcgcca taccaaaatt cacaccggat ccgaacggcc gtttcagtgc     180
cgtatttgca tgcgtaattt tagccagcgt gcgaccctgc agcgccatat tcgtacccat     240
accggtgaaa aaccgtttgc ctgcgatatt tgtggccgta aatttgccca gcgcgcgacc     300
ctgcagcgcc ataccaaaat tcataccggt tctgaacggc cgtttcagtg caggatttgc     360
atgcgtaatt tttcccagcg cgcgaccctg cagcgccata ttcgcaccca tactggtgaa     420
aaaccgtttg cctgcgatat ttgcggtcgt aaatttgcgc agcgtgctac cttacagcgc     480
cataccaaaa ttcat                                                      495

<210> SEQ ID NO 10
<211> LENGTH: 331
<212> TYPE: PRT
<213> ORGANISM: Artificial Sequence
<220> FEATURE:
<223> OTHER INFORMATION: Description of Artificial Sequence: Synthetic
      zinc finger polypeptide

<400> SEQUENCE: 10

Phe Gln Cys Arg Ile Cys Met Arg Asn Phe Ser Gln Arg Ala Thr Leu
1               5                   10                  15

Gln Arg His Thr Lys Ile His Thr Gly Ser Glu Arg Pro Phe Gln Cys
            20                  25                  30

Arg Ile Cys Met Arg Asn Phe Ser Gln Arg Ala Thr Leu Gln Arg His
        35                  40                  45

Ile Arg Thr His Thr Gly Glu Lys Pro Phe Ala Cys Asp Ile Cys Gly
    50                  55                  60

Arg Lys Phe Ala Gln Arg Ala Thr Leu Gln Arg His Thr Lys Ile His
65                  70                  75                  80

Thr Gly Ser Glu Arg Pro Phe Gln Cys Arg Ile Cys Met Arg Asn Phe
                85                  90                  95

Ser Gln Arg Ala Thr Leu Gln Arg His Ile Arg Thr His Thr Gly Glu
            100                 105                 110

Lys Pro Phe Ala Cys Asp Ile Cys Gly Arg Lys Phe Ala Gln Arg Ala
        115                 120                 125

Thr Leu Gln Arg His Thr Lys Ile His Leu Arg Gln Lys Asp Gly Gly
    130                 135                 140

Gly Gly Ser Gly Gly Gly Gly Ser Gly Gly Gly Gly Ser Gln Leu Val
145                 150                 155                 160

Gly Thr Ala Glu Arg Pro Phe Gln Cys Arg Ile Cys Met Arg Asn Phe
                165                 170                 175

Ser Gln Arg Ala Thr Leu Gln Arg His Ile Arg Thr His Thr Gly Glu
            180                 185                 190

Lys Pro Phe Ala Cys Asp Ile Cys Gly Arg Lys Phe Ala Gln Arg Ala
        195                 200                 205

Thr Leu Gln Arg His Thr Lys Ile His Thr Gly Ser Glu Arg Pro Phe
    210                 215                 220

Gln Cys Arg Ile Cys Met Arg Asn Phe Ser Gln Arg Ala Thr Leu Gln
225                 230                 235                 240

Arg His Ile Arg Thr His Thr Gly Glu Lys Pro Phe Ala Cys Asp Ile
                245                 250                 255
```

```
Cys Gly Arg Lys Phe Ala Gln Arg Ala Thr Leu Gln Arg His Thr Lys
                260                 265                 270

Ile His Thr Gly Ser Glu Arg Pro Phe Gln Cys Arg Ile Cys Met Arg
            275                 280                 285

Asn Phe Ser Gln Arg Ala Thr Leu Gln Arg His Ile Arg Thr His Thr
        290                 295                 300

Gly Glu Lys Pro Phe Ala Cys Asp Ile Cys Gly Arg Lys Phe Ala Gln
305                 310                 315                 320

Arg Ala Thr Leu Gln Arg His Thr Lys Ile His
                325                 330
```

<210> SEQ ID NO 11
<211> LENGTH: 993
<212> TYPE: DNA
<213> ORGANISM: Artificial Sequence
<220> FEATURE:
<223> OTHER INFORMATION: Description of Artificial Sequence: Synthetic
      polynucleotide encoding synthetic zinc finger peptide

<400> SEQUENCE: 11

```
ttccagtgcc gcatttgtat gcgcaacttt agccagcgcg cgacccctgca gcgccatacc     60
aaaattcaca ccggatccga acggccgttt cagtgccgta tttgcatgcg taattttagc    120
cagcgtgcga ccctgcagcg ccatattcgt acccataccg gtgaaaaacc gtttgcctgc    180
gatatttgtg gccgtaaatt tgcccagcgc gcgaccctgc agcgccatac aaaattcat     240
accggttctg aacggccgtt tcagtgcagg atttgcatgc gtaattttc ccagcgcgcg     300
accctgcagc gccatattcg cacccatact ggtgaaaaac cgtttgcctg cgatatttgc    360
ggtcgtaaat tgcgcagcg tgctacctta cagcgccata ccaaaattca tctgcgccag    420
aaagatggtg gcgcggctc aggtggcggc ggtagtggtg gcggcggctc acaactagtc    480
ggtaccgccg agcgccccctt ccagtgccgc atttgtatgc gcaactttag ccagcgcgcg    540
accctgcagc gtcatattcg cacccatacc ggtgaaaaac cgtttgcgtg cgatatttgc    600
ggtcgtaaat tgcgcagcg tgcgaccctg cagcgccata ccaaaattca caccggatcc    660
gaacggccgt tcagtgccg tatttgcatg cgtaattta gccagcgtgc gaccctgcag    720
cgccatattc gtacccatac cggtgaaaaa ccgtttgcct gcgatatttg tggccgtaaa    780
tttgcccagc gcgcgaccct gcagcgccat accaaaattc ataccggttc tgaacggccg    840
tttcagtgca ggatttgcat gcgtaatttt cccagcgcg cgaccctgca gcgccatatt    900
cgcacccata ctggtgaaaa accgtttgcc tgcgatattt gcggtcgtaa atttgcgcag    960
cgtgctacct tacagcgcca taccaaaatt cat                                  993
```

<210> SEQ ID NO 12
<211> LENGTH: 359
<212> TYPE: PRT
<213> ORGANISM: Artificial Sequence
<220> FEATURE:
<223> OTHER INFORMATION: Description of Artificial Sequence: Synthetic
      zinc finger polypeptide

<400> SEQUENCE: 12

```
Phe Gln Cys Arg Ile Cys Met Arg Asn Phe Ser Gln Arg Ala Thr Leu
1               5                   10                  15

Gln Arg His Ile Arg Thr His Thr Gly Glu Lys Pro Phe Ala Cys Asp
            20                  25                  30

Ile Cys Gly Arg Lys Phe Ala Gln Arg Ala Thr Leu Gln Arg His Thr
        35                  40                  45
```

Lys Ile His Thr Gly Ser Glu Arg Pro Phe Gln Cys Arg Ile Cys Met
                50                  55                  60

Arg Asn Phe Ser Gln Arg Ala Thr Leu Gln Arg His Ile Arg Thr His
 65                  70                  75                  80

Thr Gly Glu Lys Pro Phe Ala Cys Asp Ile Cys Gly Arg Lys Phe Ala
                 85                  90                  95

Gln Arg Ala Thr Leu Gln Arg His Thr Lys Ile His Thr Gly Ser Glu
                100                 105                 110

Arg Pro Phe Gln Cys Arg Ile Cys Met Arg Asn Phe Ser Gln Arg Ala
                115                 120                 125

Thr Leu Gln Arg His Ile Arg Thr His Thr Gly Glu Lys Pro Phe Ala
130                 135                 140

Cys Asp Ile Cys Gly Arg Lys Phe Ala Gln Arg Ala Thr Leu Gln Arg
145                 150                 155                 160

His Thr Lys Ile His Leu Arg Gln Lys Asp Gly Gly Gly Ser Gly
                165                 170                 175

Gly Gly Gly Ser Gly Gly Gly Gly Ser Gln Leu Val Gly Thr Ala Glu
                180                 185                 190

Arg Pro Phe Gln Cys Arg Ile Cys Met Arg Asn Phe Ser Gln Arg Ala
                195                 200                 205

Thr Leu Gln Arg His Ile Arg Thr His Thr Gly Glu Lys Pro Phe Ala
210                 215                 220

Cys Asp Ile Cys Gly Arg Lys Phe Ala Gln Arg Ala Thr Leu Gln Arg
225                 230                 235                 240

His Thr Lys Ile His Thr Gly Ser Glu Arg Pro Phe Gln Cys Arg Ile
                245                 250                 255

Cys Met Arg Asn Phe Ser Gln Arg Ala Thr Leu Gln Arg His Ile Arg
                260                 265                 270

Thr His Thr Gly Glu Lys Pro Phe Ala Cys Asp Ile Cys Gly Arg Lys
            275                 280                 285

Phe Ala Gln Arg Ala Thr Leu Gln Arg His Thr Lys Ile His Thr Gly
290                 295                 300

Ser Glu Arg Pro Phe Gln Cys Arg Ile Cys Met Arg Asn Phe Ser Gln
305                 310                 315                 320

Arg Ala Thr Leu Gln Arg His Ile Arg Thr His Thr Gly Glu Lys Pro
                325                 330                 335

Phe Ala Cys Asp Ile Cys Gly Arg Lys Phe Ala Gln Arg Ala Thr Leu
                340                 345                 350

Gln Arg His Thr Lys Ile His
        355

```
<210> SEQ ID NO 13
<211> LENGTH: 1077
<212> TYPE: DNA
<213> ORGANISM: Artificial Sequence
<220> FEATURE:
<223> OTHER INFORMATION: Description of Artificial Sequence: Synthetic
      polynucleotide encoding synthetic zinc finger peptide

<400> SEQUENCE: 13
ttccagtgcc gcatttgtat gcgcaacttt agccagcgcg cgaccctgca gcgtcatatt      60
cgcacccata ccggtgaaaa accgtttgcg tgcgatattt gcggtcgtaa atttgcgcag     120
cgtgcgaccc tgcagcgcca taccaaaatt cacaccggat ccgaacggcc gtttcagtgc     180
cgtatttgca tgcgtaattt tagccagcgt gcgaccctgc agcgccatat tcgtacccat     240
```

```
accggtgaaa aaccgtttgc ctgcgatatt tgtggccgta aatttgccca gcgcgcgacc    300
ctgcagcgcc ataccaaaat tcataccggt tctgaacggc cgtttcagtg caggatttgc    360
atgcgtaatt tttcccagcg cgcgaccctg cagcgccata ttcgcaccca tactggtgaa    420
aaaccgtttg cctgcgatat ttgcggtcgt aaatttgcgc agcgtgctac cttacagcgc    480
cataccaaaa ttcatctgcg ccagaaagat ggtggcggcg gctcaggtgg cggcggtagt    540
ggtggcggcg gctcacaact agtcggtacc gccgagcgcc ccttccagtg ccgcatttgt    600
atgcgcaact ttagccagcg cgcgaccctg cagcgtcata ttcgcaccca taccggtgaa    660
aaaccgtttg cgtgcgatat ttgcggtcgt aaatttgcgc agcgtgcgac cctgcagcgc    720
cataccaaaa ttcacaccgg atccgaacgg ccgtttcagt gccgtatttg catgcgtaat    780
tttagccagc gtgcgaccct gcagcgccat attcgtaccc ataccggtga aaaaccgttt    840
gcctgcgata tttgtggccg taaatttgcc cagcgcgcga ccctgcagcg ccataccaaa    900
attcataccg gttctgaacg gccgtttcag tgcaggattt gcatgcgtaa tttttcccag    960
cgcgcgaccc tgcagcgcca tattcgcacc catactggtg aaaaaccgtt tgcctgcgat   1020
atttgcggtc gtaaatttgc gcagcgtgct accttacagc gccataccaa aattcat     1077
```

<210> SEQ ID NO 14
<211> LENGTH: 528
<212> TYPE: PRT
<213> ORGANISM: Artificial Sequence
<220> FEATURE:
<223> OTHER INFORMATION: Description of Artificial Sequence: Synthetic zinc finger polypeptide

<400> SEQUENCE: 14

```
Phe Gln Cys Arg Ile Cys Met Arg Asn Phe Ser Gln Arg Ala Thr Leu
1               5                   10                  15

Gln Arg His Ile Arg Thr His Thr Gly Glu Lys Pro Phe Ala Cys Asp
            20                  25                  30

Ile Cys Gly Arg Lys Phe Ala Gln Arg Ala Thr Leu Gln Arg His Thr
        35                  40                  45

Lys Ile His Thr Gly Ser Glu Arg Pro Phe Gln Cys Arg Ile Cys Met
    50                  55                  60

Arg Asn Phe Ser Gln Arg Ala Thr Leu Gln Arg His Ile Arg Thr His
65                  70                  75                  80

Thr Gly Glu Lys Pro Phe Ala Cys Asp Ile Cys Gly Arg Lys Phe Ala
                85                  90                  95

Gln Arg Ala Thr Leu Gln Arg His Thr Lys Ile His Thr Gly Ser Glu
            100                 105                 110

Arg Pro Phe Gln Cys Arg Ile Cys Met Arg Asn Phe Ser Gln Arg Ala
        115                 120                 125

Thr Leu Gln Arg His Ile Arg Thr His Thr Gly Glu Lys Pro Phe Ala
    130                 135                 140

Cys Asp Ile Cys Gly Arg Lys Phe Ala Gln Arg Ala Thr Leu Gln Arg
145                 150                 155                 160

His Thr Lys Ile His Leu Arg Gln Lys Asp Gly Gly Gly Ser Gln Leu
                165                 170                 175

Val Gly Thr Ala Glu Arg Pro Phe Gln Cys Arg Ile Cys Met Arg Asn
            180                 185                 190

Phe Ser Gln Arg Ala Thr Leu Gln Arg His Ile Arg Thr His Thr Gly
        195                 200                 205
```

Glu Lys Pro Phe Ala Cys Asp Ile Cys Gly Arg Lys Phe Ala Gln Arg
    210                 215                 220

Ala Thr Leu Gln Arg His Thr Lys Ile His Thr Gly Ser Glu Arg Pro
225                 230                 235                 240

Phe Gln Cys Arg Ile Cys Met Arg Asn Phe Ser Gln Arg Ala Thr Leu
                245                 250                 255

Gln Arg His Ile Arg Thr His Thr Gly Glu Lys Pro Phe Ala Cys Asp
            260                 265                 270

Ile Cys Gly Arg Lys Phe Ala Gln Arg Ala Thr Leu Gln Arg His Thr
        275                 280                 285

Lys Ile His Thr Gly Ser Glu Arg Pro Phe Gln Cys Arg Ile Cys Met
290                 295                 300

Arg Asn Phe Ser Gln Arg Ala Thr Leu Gln Arg His Ile Arg Thr His
305                 310                 315                 320

Thr Gly Glu Lys Pro Phe Ala Cys Asp Ile Cys Gly Arg Lys Phe Ala
                325                 330                 335

Gln Arg Ala Thr Leu Gln Arg His Thr Lys Ile His Leu Arg Gln Lys
            340                 345                 350

Asp Gly Gly Gly Ser Gly Thr Ala Glu Arg Pro Phe Gln Cys Arg Ile
        355                 360                 365

Cys Met Arg Asn Phe Ser Gln Arg Ala Thr Leu Gln Arg His Ile Arg
    370                 375                 380

Thr His Thr Gly Glu Lys Pro Phe Ala Cys Asp Ile Cys Gly Arg Lys
385                 390                 395                 400

Phe Ala Gln Arg Ala Thr Leu Gln Arg His Thr Lys Ile His Thr Gly
                405                 410                 415

Ser Glu Arg Pro Phe Gln Cys Arg Ile Cys Met Arg Asn Phe Ser Gln
            420                 425                 430

Arg Ala Thr Leu Gln Arg His Ile Arg Thr His Thr Gly Glu Lys Pro
        435                 440                 445

Phe Ala Cys Asp Ile Cys Gly Arg Lys Phe Ala Gln Arg Ala Thr Leu
    450                 455                 460

Gln Arg His Thr Lys Ile His Thr Gly Ser Glu Arg Pro Phe Gln Cys
465                 470                 475                 480

Arg Ile Cys Met Arg Asn Phe Ser Gln Arg Ala Thr Leu Gln Arg His
                485                 490                 495

Ile Arg Thr His Thr Gly Glu Lys Pro Phe Ala Cys Asp Ile Cys Gly
            500                 505                 510

Arg Lys Phe Ala Gln Arg Ala Thr Leu Gln Arg His Thr Lys Ile His
        515                 520                 525

<210> SEQ ID NO 15
<211> LENGTH: 1584
<212> TYPE: DNA
<213> ORGANISM: Artificial Sequence
<220> FEATURE:
<223> OTHER INFORMATION: Description of Artificial Sequence: Synthetic
      polynucleotide encoding synthetic zinc finger peptide

<400> SEQUENCE: 15
ttccagtgcc gcatttgtat gcgcaacttt agccagcgcg cgaccctgca gcgtcatatt      60
cgcacccata ccggtgaaaa accgtttgcg tgcgatattt gcggtcgtaa atttgcgcag     120
cgtgcgaccc tgcagcgcca taccaaaatt cacaccggat ccgaacggcc gtttcagtgc     180
cgtatttgca tgcgtaattt tagccagcgt gcgaccctgc agcgccatat tcgtacccat     240

```
accggtgaaa aaccgtttgc ctgcgatatt tgtggccgta aatttgccca gcgcgcgacc    300
ctgcagcgcc ataccaaaat tcataccggt tctgaacggc cgtttcagtg caggatttgc    360
atgcgtaatt tttcccagcg cgcgaccctg cagcgccata ttcgcaccca tactggtgaa    420
aaaccgtttg cctgcgatat ttgcggtcgt aaatttgcgc agcgtgctac cttacagcgc    480
cataccaaaa ttcatctgcg ccagaaagat ggtggcggct cacaactagt cggtaccgcc    540
gagcgcccct ccagtgccg catttgtatg cgcaacttta gccagcgcgc gaccctgcag    600
cgtcatattc gcacccatac cggtgaaaaa ccgtttgcgt gcgatatttg cggtcgtaaa    660
tttgcgcagc gtgcgaccct gcagcgccat accaaaattc acaccggatc cgaacggccg    720
tttcagtgcc gtatttgcat gcgtaatttt agccagcgtg cgaccctgca gcgccatatt    780
cgtacccata ccggtgaaaa accgtttgcc tgcgatattt gtggccgtaa atttgcccag    840
cgcgcgaccc tgcagcgcca taccaaaatt cataccggtt ctgaacggcc gtttcagtgc    900
aggatttgca tgcgtaattt ttcccagcgc gcgaccctgc agcgccatat tcgcacccat    960
actggtgaaa aaccgtttgc ctgcgatatt tgcggtcgta aatttgcgca gcgtgctacc   1020
ttacagcgcc ataccaaaat tcatctgcgc cagaaagatg gtggcggctc aggtaccgcc   1080
gagcgcccct ccagtgccg catttgtatg cgcaacttta gccagcgcgc gaccctgcag   1140
cgtcatattc gcacccatac cggtgaaaaa ccgtttgcgt gcgatatttg cggtcgtaaa   1200
tttgcgcagc gtgcgaccct gcagcgccat accaaaattc acaccggatc cgaacggccg   1260
tttcagtgcc gtatttgcat gcgtaatttt agccagcgtg cgaccctgca gcgccatatt   1320
cgtacccata ccggtgaaaa accgtttgcc tgcgatattt gtggccgtaa atttgcccag   1380
cgcgcgaccc tgcagcgcca taccaaaatt cataccggtt ctgaacggcc gtttcagtgc   1440
aggatttgca tgcgtaattt ttcccagcgc gcgaccctgc agcgccatat tcgcacccat   1500
actggtgaaa aaccgtttgc ctgcgatatt tgcggtcgta aatttgcgca gcgtgctacc   1560
ttacagcgcc ataccaaaat tcat                                           1584
```

<210> SEQ ID NO 16
<211> LENGTH: 118
<212> TYPE: PRT
<213> ORGANISM: Homo sapiens

<400> SEQUENCE: 16

```
Ser Ser Leu Ser Pro Gln His Ser Ala Val Thr Gln Gly Ser Ile Ile
1               5                   10                  15

Lys Asn Lys Glu Gly Met Asp Ala Lys Ser Leu Thr Ala Trp Ser Arg
            20                  25                  30

Thr Leu Val Thr Phe Lys Asp Val Phe Val Asp Phe Thr Arg Glu Glu
        35                  40                  45

Trp Lys Leu Leu Asp Thr Ala Gln Gln Ile Val Tyr Arg Asn Val Met
    50                  55                  60

Leu Glu Asn Tyr Lys Asn Leu Val Ser Leu Gly Tyr Gln Leu Thr Lys
65                  70                  75                  80

Pro Asp Val Ile Leu Arg Leu Glu Lys Gly Glu Glu Pro Trp Leu Val
                85                  90                  95

Glu Arg Glu Ile His Gln Glu Thr His Pro Asp Ser Glu Thr Ala Phe
            100                 105                 110

Glu Ile Lys Ser Ser Val
        115
```

```
<210> SEQ ID NO 17
<211> LENGTH: 354
<212> TYPE: DNA
<213> ORGANISM: Homo sapiens

<400> SEQUENCE: 17
tctagtttgt ctcctcagca ctctgctgtc actcaaggaa gtatcatcaa gaacaaggag      60
ggcatggatg ctaagtcact aactgcctgg tcccggacac tggtgacctt caaggatgta     120
tttgtggact tcaccaggga ggagtggaag ctgctggaca ctgctcagca gatcgtgtac     180
agaaatgtga tgctggagaa ctataagaac ctggtttcct tgggttatca gcttactaag     240
ccagatgtga tcctccggtt ggagaaggga gaagagccct ggctggtgga gagagaaatt     300
caccaagaga cccatcctga ttcagagact gcatttgaaa tcaaatcatc agtt          354

<210> SEQ ID NO 18
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Arg Gln Lys Asp Gly Gly Gly Ser Gly Gly Gly Ser Gly
1               5                   10                  15

Gly Gly Ser Gln Leu Val
            20

<210> SEQ ID NO 19
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide encoding synthetic peptide

<400> SEQUENCE: 19
ctgcgccaga agatggtgg cggcggctca ggtggcggcg gtagtggtgg cggcggctca       60
caactagtc                                                             69

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 20

Thr Gly Glu Lys Pro
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide
<220> FEATURE:
<221> NAME/KEY: MOD_RES
<222> LOCATION: (3)..(3)
<223> OTHER INFORMATION: Glu or Gln
<220> FEATURE:
<221> NAME/KEY: MOD_RES
```

```
<222> LOCATION: (4)..(4)
<223> OTHER INFORMATION: Lys or Arg

<400> SEQUENCE: 21

Thr Gly Xaa Xaa Pro
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      linker peptide
<220> FEATURE:
<221> NAME/KEY: MOD_RES
<222> LOCATION: (3)..(3)
<223> OTHER INFORMATION: Gly or Ser
<220> FEATURE:
<221> NAME/KEY: MOD_RES
<222> LOCATION: (4)..(4)
<223> OTHER INFORMATION: Glu or Gln
<220> FEATURE:
<221> NAME/KEY: MOD_RES
<222> LOCATION: (5)..(5)
<223> OTHER INFORMATION: Lys or Arg

<400> SEQUENCE: 22

Thr Gly Xaa Xaa Xaa Pro
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 23

Thr Gly Gly Glu Arg Pro
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 24

Thr Gly Ser Glu Arg Pro
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 25

Thr Gly Gly Gln Arg Pro
1               5

<210> SEQ ID NO 26
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 26

Thr Gly Ser Gln Arg Pro
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 27

Thr Gly Gly Glu Lys Pro
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 28

Thr Gly Ser Glu Lys Pro
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 29

Thr Gly Gly Gln Lys Pro
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 30

Thr Gly Ser Gln Lys Pro
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      linker peptide
<220> FEATURE:
<221> NAME/KEY: MOD_RES
<222> LOCATION: (3)..(5)
<223> OTHER INFORMATION: Gly or Ser
```

```
<220> FEATURE:
<221> NAME/KEY: MOD_RES
<222> LOCATION: (6)..(6)
<223> OTHER INFORMATION: Glu or Gln
<220> FEATURE:
<221> NAME/KEY: MOD_RES
<222> LOCATION: (7)..(7)
<223> OTHER INFORMATION: Lys or Arg

<400> SEQUENCE: 31

Thr Gly Xaa Xaa Xaa Xaa Xaa Pro
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      linker peptide
<220> FEATURE:
<221> NAME/KEY: MOD_RES
<222> LOCATION: (2)..(4)
<223> OTHER INFORMATION: Gly or Ser
<220> FEATURE:
<221> NAME/KEY: MOD_RES
<222> LOCATION: (6)..(6)
<223> OTHER INFORMATION: Glu or Gln
<220> FEATURE:
<221> NAME/KEY: MOD_RES
<222> LOCATION: (7)..(7)
<223> OTHER INFORMATION: Lys or Arg

<400> SEQUENCE: 32

Thr Xaa Xaa Xaa Gly Xaa Xaa Pro
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      linker peptide
<220> FEATURE:
<221> NAME/KEY: MOD_RES
<222> LOCATION: (3)..(4)
<223> OTHER INFORMATION: Gly or Ser
<220> FEATURE:
<221> NAME/KEY: MOD_RES
<222> LOCATION: (5)..(5)
<223> OTHER INFORMATION: Glu or Gln
<220> FEATURE:
<221> NAME/KEY: MOD_RES
<222> LOCATION: (6)..(6)
<223> OTHER INFORMATION: Lys or Arg

<400> SEQUENCE: 33

Thr Gly Xaa Xaa Xaa Xaa Pro
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      linker peptide
<220> FEATURE:
<221> NAME/KEY: MOD_RES
<222> LOCATION: (2)..(3)
<223> OTHER INFORMATION: Gly or Ser
<220> FEATURE:
```

```
<221> NAME/KEY: MOD_RES
<222> LOCATION: (5)..(5)
<223> OTHER INFORMATION: Glu or Gln
<220> FEATURE:
<221> NAME/KEY: MOD_RES
<222> LOCATION: (6)..(6)
<223> OTHER INFORMATION: Lys or Arg

<400> SEQUENCE: 34

Thr Xaa Xaa Gly Xaa Xaa Pro
1               5

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 35

Leu Arg Gln Lys Asp Gly Gly Gly Gly Ser Gln Leu Val Gly Thr Ala
1               5                   10                  15

Glu Arg Pro

<210> SEQ ID NO 36
<211> LENGTH: 24
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 36

Leu Arg Gln Lys Asp Gly Gly Gly Gly Ser Gly Gly Gly Gly Ser Gln
1               5                   10                  15

Leu Val Gly Thr Ala Glu Arg Pro
            20

<210> SEQ ID NO 37
<211> LENGTH: 29
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 37

Leu Arg Gln Lys Asp Gly Gly Gly Gly Ser Gly Gly Gly Gly Ser Gly
1               5                   10                  15

Gly Gly Gly Ser Gln Leu Val Gly Thr Ala Glu Arg Pro
            20                  25

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 38

Leu Arg Gln Lys Asp Gly Gly Gly Ser Gln Leu Val Gly Thr Ala Glu
1               5                   10                  15

Arg Pro
```

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 39

Leu Arg Gln Lys Asp Gly Gly Gly Ser Gly Thr Ala Glu Arg Pro
1               5                   10                  15

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      targeting peptide

<400> SEQUENCE: 40

Pro Lys Lys Lys Arg Lys Val
1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      leader peptide

<400> SEQUENCE: 41

Met Ala Glu Arg Pro
1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      leader peptide

<400> SEQUENCE: 42

Met Ala Glu Glu Arg Pro
1               5

<210> SEQ ID NO 43
<211> LENGTH: 12
<212> TYPE: DNA
<213> ORGANISM: Homo sapiens
<220> FEATURE:
<221> NAME/KEY: misc_feature
<222> LOCATION: (1)..(12)
<223> OTHER INFORMATION: Repeat unit

<400> SEQUENCE: 43
ccccgccccg cg                                                          12

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      recognition peptide

```
<400> SEQUENCE: 44

Gln Ala Ala Thr Leu Gln Arg
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      recognition peptide

<400> SEQUENCE: 45

Gln Ala Gln Thr Leu Gln Arg
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      recognition peptide

<400> SEQUENCE: 46

Gln Arg Ala Ser Arg Lys Arg
1               5

<210> SEQ ID NO 47
<211> LENGTH: 22
<212> TYPE: PRT
<213> ORGANISM: Artificial Sequence
<220> FEATURE:
<223> OTHER INFORMATION: Description of Artificial Sequence: Synthetic
      flag peptide

<400> SEQUENCE: 47

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 48

Gly Gly Gly Gly Ser
1               5

<210> SEQ ID NO 49
<211> LENGTH: 29
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (9)..(11)
<223> OTHER INFORMATION: 'cag' repeat unit

<400> SEQUENCE: 49
```
acgtaccagt cacagtcagt ccacacgtc        29

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cctgaagttc atctgcacca        20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
aagtcgtgct gcttcatgtg        20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
agatgctgcg gaagaagaag        20

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggtaccgtcg actgcagaa        19

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ctttgctttc cttggtcagg        20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tatccaacac ttcgtggggt        20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
gtctccctcc gatctggata        20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
cacacttcca gggctgtaga        20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
ccagcaccgt agagaggatt        20

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
agccctgtcc aaacacaaa        19

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
gacgcagctg agcaagttag        20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
gaaggaacgt gggttgaact        20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
agagcttcgg aagagacgag					20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
actcccaagt gctcctgaac					20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
aactgtgtgg ctcactctgg					20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
tgggaagatg ttaccgttga					20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
gggaactaca ccctcctgaa					20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
cgctgcttct tcttcctctt					20

```
<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
acgccgaata taatcccaag                                              20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cttcactctt ggctcctgtg                                              20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
cagatgtcag aatggtggct                                              20

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gccttggaag attagaatcc a                                            21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cacctgcctc cacctcatgg c                                            21

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
atgctccttg ggggccctgg                                              20

<210> SEQ ID NO 74
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
tgtggagaga atcgaggaga                                                 20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cagccctgtc caaatacaaa                                                 20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
atcccaatgc aaaggagttc                                                 20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ctgctgatga cccaccatag                                                 20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
acctcgcact attcttggct                                                 20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tgcatctgtt ggaccttgat                                                 20

<210> SEQ ID NO 80
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tgcccgtgtt cctcaccgga                                                   20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gcgcggagac agtggttgct                                                   20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cactggcaat agcaaaggaa                                                   20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ttcttgagcg agttcaccac                                                   20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
acttcgtgca agaaatgctg                                                   20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gctcatagct cttggctcct                                                   20

<210> SEQ ID NO 86
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 86
tcctggcttt gaggagccga                                                    20

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ccacagcaca gctctgcagc at                                                 22

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gggggctcaa gcaggcatgg                                                    20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gggagccagc ctccgagtca                                                    20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
cagatgtcag aatggtggct                                                    20

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gccttggaag attagaatcc a                                                  21

<210> SEQ ID NO 92
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 92
ggttaagcag tacagcccca                                                 20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
agaggtcctt ttcaccagca                                                 20

<210> SEQ ID NO 94
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gtaaaacgac ggccag                                                     16

<210> SEQ ID NO 95
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
caggaaacag ctatgac                                                    17

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      recognition peptide

<400> SEQUENCE: 96

Gln Ser Ser Asp Leu Thr Arg
1               5

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      recognition peptide

<400> SEQUENCE: 97

Gln Ser Gly Asp Leu Thr Arg
1               5

<210> SEQ ID NO 98
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 98
gcagcagcag cagcagca                                                   18

<210> SEQ ID NO 99
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 99
gcagctgcag ctgcagct                                                   18

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 100
cagcagcagc agcagcagca g                                               21

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      generic CAG-recognition peptide
<220> FEATURE:
<221> NAME/KEY: MOD_RES
<222> LOCATION: (2)..(2)
<223> OTHER INFORMATION: Arg, Leu or Ser
<220> FEATURE:
<221> NAME/KEY: MOD_RES
<222> LOCATION: (3)..(3)
<223> OTHER INFORMATION: Ala or Ser
<220> FEATURE:
<221> NAME/KEY: MOD_RES
<222> LOCATION: (4)..(4)
<223> OTHER INFORMATION: Thr, Val, Asp or Glu
<220> FEATURE:
<221> NAME/KEY: MOD_RES
<222> LOCATION: (6)..(6)
<223> OTHER INFORMATION: Gln, Thr or Ser

<400> SEQUENCE: 101

Gln Xaa Xaa Xaa Leu Xaa Arg
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      CAG-recognition peptide

<400> SEQUENCE: 102

Gln Arg Ala Thr Leu Thr Arg
1               5
```

```
<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      CAG-recognition peptide

<400> SEQUENCE: 103

Gln Arg Ala Thr Leu Ser Arg
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      CAG-recognition peptide

<400> SEQUENCE: 104

Gln Leu Ala Thr Leu Gln Arg
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      CAG-recognition peptide

<400> SEQUENCE: 105

Gln Ser Ser Val Leu Gln Arg
1               5

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      CAG-recognition peptide

<400> SEQUENCE: 106

Gln Ser Ala Asp Leu Thr Arg
1               5

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      CAG-recognition peptide

<400> SEQUENCE: 107

Gln Ser Ser Glu Leu Gln Arg
1               5

<210> SEQ ID NO 108
<211> LENGTH: 292
<212> TYPE: PRT
<213> ORGANISM: Artificial Sequence
<220> FEATURE:
<223> OTHER INFORMATION: Description of Artificial Sequence: Synthetic
      ZF10xHunt polypeptide
```

<400> SEQUENCE: 108

Tyr Ala Cys Pro Val Glu Ser Cys Asp Arg Arg Phe Ser Gln Arg Ala
1               5                   10                  15

Thr Leu Thr Arg His Ile Arg Ile His Thr Gly Gln Lys Pro Phe Gln
            20                  25                  30

Cys Arg Ile Cys Met Arg Asn Phe Ser Gln Arg Ala Thr Leu Ser Arg
        35                  40                  45

His Ile Arg Thr His Gln Asn Lys Lys Gly Ser His Ile Cys His Ile
    50                  55                  60

Gln Gly Cys Gly Lys Val Tyr Gly Gln Arg Ala Thr Leu Gln Arg His
65              70                  75                  80

Leu Arg Trp His Thr Gly Glu Arg Pro Phe Met Cys Thr Trp Ser Tyr
                85                  90                  95

Cys Gly Lys Arg Phe Thr Gln Arg Ala Thr Leu Gln Arg His Lys Arg
            100                 105                 110

Thr His Leu Arg Gln Lys Asp Gly Glu Arg Pro Tyr Ala Cys Pro Val
        115                 120                 125

Glu Ser Cys Asp Arg Arg Phe Ser Gln Arg Ala Thr Leu Ser Arg His
    130                 135                 140

Ile Arg Ile His Thr Gly Glu Lys Pro Tyr Lys Cys Pro Glu Cys Gly
145                 150                 155                 160

Lys Ser Phe Ser Gln Arg Ala Thr Leu Gln Arg His Gln Arg Thr His
                165                 170                 175

Thr Gly Ser Glu Arg Pro Phe Met Cys Asn Trp Ser Tyr Cys Gly Lys
            180                 185                 190

Arg Phe Thr Gln Arg Ala Thr Leu Thr Arg His Lys Arg Thr His Thr
        195                 200                 205

Gly Glu Lys Pro Phe Ala Cys Pro Glu Cys Pro Lys Arg Phe Met Gln
    210                 215                 220

Arg Ala Thr Leu Gln Arg His Ile Lys Thr His Thr Gly Ser Glu Lys
225                 230                 235                 240

Pro Phe Gln Cys Arg Ile Cys Met Arg Asn Phe Ser Gln Arg Ala Thr
                245                 250                 255

Leu Gln Arg His Ile Arg Thr His Thr Gly Glu Arg Pro Phe Ala Cys
            260                 265                 270

Asp Ile Cys Gly Arg Lys Phe Ala Gln Arg Ala Thr Leu Gln Arg His
        275                 280                 285

Thr Lys Ile His
    290

<210> SEQ ID NO 109
<211> LENGTH: 876
<212> TYPE: DNA
<213> ORGANISM: Artificial Sequence
<220> FEATURE:
<223> OTHER INFORMATION: Description of Artificial Sequence: Synthetic
      polynucleotide encoding ZF10xHunt peptide

<400> SEQUENCE: 109
tacgcctgcc ctgtggagtc ctgcgataga agatttttccc agagagcaac cctgaccaga      60
catattcgga ttcacaccgg ccagaagcca ttccagtgca gaatctgtat gcggaacttt     120
tcccagagag ccacactgtc tcggcacatt cgcactcatc agaataagaa agggtctcac     180
atctgccata ttcaggggtg tggcaaagtg tatggacagc gagccaccct gcagcgacac     240
ctgaggtggc ataccggaga gaggcccttc atgtgcacat ggagttactg tggcaagagg     300

```
ttcacccagc gagctacact gcagagacac aaacggacac atctgcgaca gaaggacgga      360
gagcgaccat atgcatgccc agtcgaaagt tgtgatagga gattctcaca gcgcgctact      420
ctgagccgcc acatccgaat tcataccggc gagaaacctt acaagtgccc agaatgtgga      480
aagagctttt cccagagagc aactctgcag aggcaccaga gaacccatac aggcagtgag      540
cggcccttca tgtgcaactg gtcatattgt ggaaaaaggt ttacccagag agctactctg      600
acccggcaca aacgcacaca tactggcgag aagcctttcg cttgccccga atgtcctaag      660
cggtttatgc agcgcgcaac actgcagcgg cacatcaaaa cccatacagg aagcgagaag      720
cctttccagt gccgaatttg tatgaggaat ttttcccaga gggcaactct gcagcgacac      780
atcaggactc ataccgggga acggccattc gcctgcgaca tttgtggcag aaaatttgca      840
cagcgagcta ctctgcagcg acacaccaaa atccac                                876
```

<210> SEQ ID NO 110
<211> LENGTH: 132
<212> TYPE: PRT
<213> ORGANISM: Artificial Sequence
<220> FEATURE:
<223> OTHER INFORMATION: Description of Artificial Sequence: Synthetic
    ZF10xHunt C-terminal linker and kox-1 repressor polypeptide

<400> SEQUENCE: 110

```
Leu Arg Gln Lys Asp Ala Pro Lys Lys Arg Lys Val Gly Gly Ser
1               5                   10                  15

Leu Ser Pro Gln His Ser Ala Val Thr Gln Gly Ser Ile Ile Lys Asn
            20                  25                  30

Lys Glu Gly Met Asp Ala Lys Ser Leu Thr Ala Trp Ser Arg Thr Leu
        35                  40                  45

Val Thr Phe Lys Asp Val Phe Val Asp Phe Thr Arg Glu Glu Trp Lys
    50                  55                  60

Leu Leu Asp Thr Ala Gln Gln Ile Val Tyr Arg Asn Val Met Leu Glu
65                  70                  75                  80

Asn Tyr Lys Asn Leu Val Ser Leu Gly Tyr Gln Leu Thr Lys Pro Asp
                85                  90                  95

Val Ile Leu Arg Leu Glu Lys Gly Glu Glu Pro Trp Leu Val Glu Arg
            100                 105                 110

Glu Ile His Gln Glu Thr His Pro Asp Ser Thr Ala Phe Glu Ile
        115                 120                 125

Lys Ser Ser Val
    130
```

<210> SEQ ID NO 111
<211> LENGTH: 396
<212> TYPE: DNA
<213> ORGANISM: Artificial Sequence
<220> FEATURE:
<223> OTHER INFORMATION: Description of Artificial Sequence: Synthetic
    polynucleotide encoding ZF10xHunt C-terminal linker
    and kox-1 repressor

<400> SEQUENCE: 111

```
ctgcgccaga aggatgctcc caagaaaaag aggaaagtgg gcggatctct gagtcctcag      60
cactccgcag tcacccaggg atctatcatc aagaacaagg aggggatgga cgcaaagtca      120
ctgacagcct ggagccgcac actggtgact ttcaaagacg tgttcgtcga cttcaccagg      180
gaggaatgga agctgctgga cactgcccag cagatcgtgt acaggaatgt catgctggaa      240
```

```
aactataaga atctggtgag cctgggatac cagctgacca aaccagatgt cattctgaga    300
ctggagaagg gggaggaacc ctggctggtg gaacgggaga ttcatcagga aacccaccca    360
gattcagaga cagcatttga gattaagtca tccgtc                              396
```

```
<210> SEQ ID NO 112
<211> LENGTH: 27
<212> TYPE: PRT
<213> ORGANISM: Artificial Sequence
<220> FEATURE:
<223> OTHER INFORMATION: Description of Artificial Sequence: Synthetic
      formula 4 zinc finger domain framework peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(7)
<223> OTHER INFORMATION: Any amino acid
<220> FEATURE:
<221> NAME/KEY: misc_feature
<222> LOCATION: (4)..(7)
<223> OTHER INFORMATION: This region may encompass 2 or 4 residues
<220> FEATURE:
<221> NAME/KEY: MOD_RES
<222> LOCATION: (9)..(20)
<223> OTHER INFORMATION: Any amino acid
<220> FEATURE:
<221> NAME/KEY: misc_feature
<222> LOCATION: (14)..(20)
<223> OTHER INFORMATION: Recognition sequence
<220> FEATURE:
<221> NAME/KEY: MOD_RES
<222> LOCATION: (22)..(27)
<223> OTHER INFORMATION: Any amino acid
<220> FEATURE:
<221> NAME/KEY: misc_feature
<222> LOCATION: (22)..(27)
<223> OTHER INFORMATION: This region may encompass 3, 4 or 5 residues
<220> FEATURE:
<223> OTHER INFORMATION: see specification as filed for detailed
      description of substitutions and preferred embodiments

<400> SEQUENCE: 112

Xaa Xaa Cys Xaa Xaa Xaa Xaa Cys Xaa Xaa Xaa Xaa Xaa Xaa Xaa Xaa
1               5                   10                  15

Xaa Xaa Xaa Xaa His Xaa Xaa Xaa Xaa Xaa Xaa
            20                  25

<210> SEQ ID NO 113
<211> LENGTH: 23
<212> TYPE: PRT
<213> ORGANISM: Artificial Sequence
<220> FEATURE:
<223> OTHER INFORMATION: Description of Artificial Sequence: Synthetic
      formula 6 zinc finger domain framework peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (7)..(18)
<223> OTHER INFORMATION: Any amino acid
<220> FEATURE:
<221> NAME/KEY: misc_feature
<222> LOCATION: (12)..(18)
<223> OTHER INFORMATION: Recognition sequence
<220> FEATURE:
```

```
<221> NAME/KEY: MOD_RES
<222> LOCATION: (20)..(22)
<223> OTHER INFORMATION: Any amino acid
<220> FEATURE:
<223> OTHER INFORMATION: see specification as filed for detailed
      description of substitutions and preferred embodiments

<400> SEQUENCE: 113

Xaa Xaa Cys Xaa Xaa Cys Xaa Xaa Xaa Xaa Xaa Xaa Xaa Xaa Xaa
1               5                   10                  15

Xaa Xaa His Xaa Xaa Xaa His
            20

<210> SEQ ID NO 114
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
agcagcagca gcagcagcag cagcagcagc agcagc                                 36

<210> SEQ ID NO 115
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
cagcagcagc agcag                                                        15

<210> SEQ ID NO 116
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
cagcagcagc agcagcagca gcagcagcag cagcagcag                              39

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gcagctgcag ctgcagct                                                     18

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
dagdagdagd agdagdagda g                                                 21
```

```
<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
csgcsgcsgc sgcsgcsgcs g                                           21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
cahcahcahc ahcahcahca h                                           21
```